United States Patent
Beadle et al.

(10) Patent No.: US 11,173,186 B2
(45) Date of Patent: Nov. 16, 2021

(54) DOSING REGIME AND FORMULATIONS FOR TYPE B ADENOVIRUS

(71) Applicant: PSIOXUS THERAPEUTICS LIMITED, Abingdon (GB)

(72) Inventors: John William Beadle, Abingdon (GB); Kerry Fisher, Abingdon (GB); Christine Wilkinson Blanc, Abingdon (GB)

(73) Assignee: PSIOXUS THERAPEUTICS LIMITED, Abingdon (GB)

( * ) Notice: Subject to any disclaimer, the term of this patent is extended or adjusted under 35 U.S.C. 154(b) by 5 days.

(21) Appl. No.: 14/896,294

(22) PCT Filed: Jun. 12, 2014

(86) PCT No.: PCT/EP2014/062284
§ 371 (c)(1),
(2) Date: Dec. 4, 2015

(87) PCT Pub. No.: WO2014/198852
PCT Pub. Date: Dec. 18, 2014

(65) Prior Publication Data
US 2016/0120922 A1    May 5, 2016

(30) Foreign Application Priority Data

Jun. 14, 2013  (GB) ................................ 1310698
Mar. 22, 2014  (GB) ................................ 1405140
Apr. 10, 2014  (GB) ................................ 1406509

(51) Int. Cl.
| | | |
|---|---|---|
| A61K 35/761 | (2015.01) | |
| A61K 38/20 | (2006.01) | |
| A61K 38/19 | (2006.01) | |
| A61K 38/21 | (2006.01) | |
| A61K 45/06 | (2006.01) | |
| A61K 33/243 | (2019.01) | |
| A61K 9/00 | (2006.01) | |
| A61K 31/337 | (2006.01) | |
| C12N 7/00 | (2006.01) | |

(52) U.S. Cl.
CPC .......... *A61K 35/761* (2013.01); *A61K 9/0019* (2013.01); *A61K 31/337* (2013.01); *A61K 33/243* (2019.01); *A61K 38/19* (2013.01); *A61K 38/2013* (2013.01); *A61K 38/212* (2013.01); *A61K 38/217* (2013.01); *A61K 45/06* (2013.01); *C12N 7/00* (2013.01); *C12N 2710/10021* (2013.01); *C12N 2710/10032* (2013.01); *C12N 2710/10071* (2013.01); *C12N 2710/10332* (2013.01)

(58) Field of Classification Search
None
See application file for complete search history.

(56) References Cited

U.S. PATENT DOCUMENTS

| | | | |
|---|---|---|---|
| 7,510,868 B2 * | 3/2009 | Harden ................ | C12N 7/00 435/320.1 |
| 8,052,965 B2 | 11/2011 | Van Beusechem et al. | |
| 2003/0044384 A1 * | 3/2003 | Roberts ................ | A61K 38/21 424/93.2 |
| 2006/0140909 A1 * | 6/2006 | Wickham ............... | C12N 15/86 424/93.2 |
| 2016/0331793 A1 | 11/2016 | Champion et al. | |

FOREIGN PATENT DOCUMENTS

| | | |
|---|---|---|
| CN | 101381742 A | 3/2009 |
| JP | 2002531133 | 9/2002 |
| JP | 2009505680 A | 2/2009 |
| WO | WO 98/19710 | 5/1998 |
| WO | 00/34494 | 6/2000 |
| WO | WO 00/74722 | 12/2000 |
| WO | WO 2005/010149 | 2/2005 |
| WO | 2005/040220 A1 | 5/2005 |
| WO | WO 2005/118825 | 12/2005 |
| WO | WO 2006/008513 | 1/2006 |
| WO | 2006060314 A2 | 6/2006 |

(Continued)

OTHER PUBLICATIONS

Kwon et al. Therapeutic Targeting of Chitosan-PEG-Folate-Complexed Oncolytic Adenovirus for Active and Systemic Cancer Gene Therapy. Journal of Controlled Release, 2013: 169:257-265, available online Apr. 4, 2013.*
Vellinga et al. The Adenovirus Capsid: Major Progress in Minor Proteins. Review. Journal of Virology, 2005. 86:1581-1588.*
Kuhn, et al., "Directed evolution generates a novel oncolytic virus for the treatment of colon cancer", PLOS ONE, 3: e2409/1-e2409/11 (2009).
Illingworth, et al., "ColoAd1 a group B oncolytic adenovirus: pre-clinical assessment of potency, safety and selectivity", Human Gene Therapy, 23:A19 (2012).
Di, et al, "Activity of group B oncolytic adenovirus (ColoAd1) in whole human blood", Gene Therapy, 21:440-443 (2014).
"Unique anti-cancer agent ColoAd1 enters the clinic", Human Vaccines and Immunotherapeutics, 8:1551 (2012).

(Continued)

*Primary Examiner* — Christopher M Babic
*Assistant Examiner* — Kimberly A Aron
(74) *Attorney, Agent, or Firm* — Debora Plehn-Dujowich; Eckert Seamans Cherin & Mellott, LLC

(57) ABSTRACT

A method of treating a human patient comprising systemically administering multiple doses of a parenteral formulation of a replication capable oncolytic adenovirus of subgroup B in a single treatment cycle, wherein the total dose given in each dose is in the range of $1 \times 10^{10}$ to $1 \times 10^{14}$ viral particles, and wherein each dose of virus is administered over a period of 1 to 90 minutes, for example at a rate of viral particle delivery in the range of $2 \times 10^{10}$ particles per minute to $2 \times 10^{12}$ particles per minute. Also provided are formulations of the oncolytic adenoviruses and combination therapies of the viruses and formulations with other therapeutic agents.

19 Claims, 25 Drawing Sheets

Specification includes a Sequence Listing.

(56) References Cited

FOREIGN PATENT DOCUMENTS

| WO | 2007027860 A2 | 3/2007 |
| --- | --- | --- |
| WO | WO 2008/08003 | 7/2008 |
| WO | 2009143610 A1 | 12/2009 |
| WO | WO 2010/38086 | 4/2010 |
| WO | WO 2010/067041 | 6/2010 |
| WO | WO 2010/067081 | 6/2010 |
| WO | WO 2011/048111 | 4/2011 |
| WO | 2013074507 A2 | 5/2013 |
| WO | 2016/030489 A1 | 3/2016 |

OTHER PUBLICATIONS

Raki, et al., "Oncolytic adenovirus ad5/3-Delta24 and chemotherapy for treatment of orthotopic ovarian cancer", Gynecologic Oncology, 108:166-172 (2007).
Small, et al., "A phase I Trial of Intravenous CG7870, a Replication-Selective, Prostate-Specific Antigen-Targeted Oncolytic Adenovirus, for the Treatment of Hormone-Refractory, Metastatic Prostate Cancer", Molecular Therapy, 14:107-117 (2006).
Russell, et al., "Concolytic virotherapy", Nature Biotechnology, 30:658-670 (2012).
Demers, et al., "Pharmacologic Indicators of Antitumor Efficacy for Oncolytic Virotherapy", Cancer Research, 63:4003-4008 (2003).
Liu, J., et al., "Complexity of coupled human and natural systems," Science 317(5844): 1513-16 (2007).
Liu, C., et al., "A Cloud and precipitation feature database from nine years of TRMM observations," J Appl Meteorol Climatol 47, 2712-28 (2008).
Bischoff, et al., "An adenovirus Mutant That Replicates Selectively in p53-Deficient Human Tumor Cells", Science 274:373-376 (1996).
Aghi, M., et al., "Oncolytic viral therapies—the clinical experience," Oncogene 24(52): 7802-16 (2005).
Carlise, et al., "Human erythrocytes bind and inactivate type 5 adenovirus by presenting Coxsackie virus-adenovirus receptor and complement receptor 1", Blood, 113:1909-1918 (2009).
Ries, et al., "ONYX-015: mechanisms of action and clinical potential of a replication-selective adenovirus", 86:5-11 (2002).
Ferguson, M. S., et al., "Systemic delivery of oncolytic viruses: hopes and hurdles," Adv Virol 2012: 805629 (2012).
Ferguson, N. D., et al., "The Berlin definition of ARDS: an expanded rationale, justification, and supplementary material," Intensive Care Med 38(10): 1573-82 (2012).
"Reolysin in Patients With Previously Treated Advanced or Metastatic, Non Small Cell Lung Cancer Receiving Standard Salvage Therapy," In: ClinicalTrials.gov [Internet]. Available from: http://clinicaltrials.gov/ct2/show/study/NCT01708993 ClinicalTrials.gov Identifier: N NCT01708993 (last updated May 4, 2016; results first received Oct. 15, 2012; cited Jun. 4, 2016).
"Safety Study of Recombinant Vaccinia Virus Administered Intravenously in Patients with Metastatic, Refractory Colorectal Carcinoma," In: ClinicalTrials.gov [Internet], Available from: http://clinicaltrials.gov/ct2/show/study/NCT01380600 ClinicalTrials.gov Identifier: NCT01380600 (last updated Jan. 6, 2016; results first received Jun. 22, 2011; cited Jun. 4, 2016).
"Recombinant Vaccinia Virus Administered Intravenously in Patients with Metastatic, Refractory Colorectal Carcinoma," In: ClinicalTrials.gov [Internet], Available from http://clinicaltrials.gov/ct2/show/study/NCT01394939 ClinicalTrials.gov Identifier: NCT01394939 (last updated Jan. 6, 2016; results first received Jul. 13, 2011; cited Jun. 4, 2016).
"Efficacy and Safety Study of Talimogene Laherparepvec Compared to Granulocyte Macrophage Colony Stimulating Factor (GM-CSF) in Melanoma," In: ClinicalTrials.gov [Internet], Available from: http://clinicaltrials.gov/ct2/show/study/NCT00769704 ClinicalTrials.gov Identifier: NCT00769704 (last updated Nov. 12, 2015; results first received Oct. 7, 2008; cited Jun. 4, 2016).
"An Extended Use Study of Safety and Efficacy of Talimogene Laherparepvec in Melanoma," In: ClinicalTrials.gov [Internet]. Available from: http://clinicaltrials.gov/ct2/show/study/NCT01368276 ClinicalTrials.gov Identifier: NCT01368276 (last updated Nov. 12, 2015; results first received Apr. 20, 2011; cited Jun. 4, 2016).
Zhang, H., et al. "Organosulfates as Tracers for Secondary Organic Aerosol (SOA)Formation from 2-Methyl-3-Buten-2-ol (MBO) in the Atmosphere," Environ Sci Technol 46 (17), 9437-46 (2012).
Shashkova, E. V., et al., "Characterization of human adenovirus serotypes 5, 6, 11, and 35 as anticancer agents," Virology 394(2): 311-20 (2009).
Greig, J. A., et al., "Influence of coagulation factor x on in vitro and in vivo gene delivery by adenovirus (Ad) 5, Ad35, and chimeric Ad5/Ad35 vectors," Mol Ther 17(10): 1683-91 (Oct. 2009).
Vogels, R., et al., "Replication-deficient human adenovirus type 35 vectors for gene transfer and vaccination: efficient human cell infection and bypass of preexisting adenovirus immunity." J Virol 77(15): 8263-71 (Aug. 2003).
Stone, D., et al., "Development and assessment of human adenovirus type 11 as a gene transfer vector," J Virol 79(8): 5090-104 (2005).
Lorence, et al., "Phase 1 Clinical Experience Using Intravenous Administration of PV701, an Oncolytic Newcastle Disease Virus", Current Cancer Drug Targets, 7:157-167 (2007).
Yu, et al., "Induced Pluripotent Stem Cell Lines Derived From Human Somatic Cells," 318:1917-1920 (2007).
Conrad, et al. "Anselm Struss and sociological study of chronic illness a reflection and appreciation", Sociology of Health & Illness, 19:373-376 (1997).
Genbank Accession No. AF532578, Publication Date: Jul. 23, 2008.
Kim, et al., "Clinical research results with dl1520 (Onyx-015), a replication-selective adenovirus for the treatment of cancer: what have we learned?" Gene Therapy, 8:89-98 (2001).
Green, et al., "Extended plasma circulation time and decreased toxicity of polymer-coated adenovirus", Gene Therapy, 11:1256-1263 (2004).
Reid, R. J., et al., "Efficient PCR-based gene disruption in *Saccharomyces* strains using intergenic primers." Yeast 19(4): 319-28 (2002).
Varela, J. C., et al., "Upregulated expression of complement inhibitory proteins on bladder cancer cells and anti-MUC1 antibody immune selection," Int J Cancer 123(6): 1357-63 (2008).
Meisner, H., et al., "Interactions of *Drosophila* Cbl with epidermal growth factor receptors and role of Cbl in R7 photoreceptor cell development," Mol Cell Biol 17(4): 2217-25 (1997).
Mei, et al., "Probe selection for high-density oligonucleotide arrays", PNAS 100:11237-11242 (2003).
Calvo, et al. "A first-in-class, first-in-human phase I study of enadenotucirev, an oncolytic Ad11/Ad3 chimeric group B adenovirus, administered intravenously in patients with metastatic epithelial tumors", Abstract #3103 (2014).
Teigler, et al., "Vaccination with Adenovirus Serotypes 35, 26, and 48 Elicits Higher Levels of Innate Cytokine Responses than Adenovirus Serotype 5 in Rhesus Monkeys", Journal of Virology, 86:9590-9598 (2012).
Calvo et al., "A phase I study of enadenotucirev, an oncolytic Ad11/Ad3 chimeric group B adenovirus, administered intravenously in patients with metastatic epithelial tumors" ASCO Annual Meeting Abstract (2014).
Lyons, et al., "Adenovirus Type 5 Interactions with Human Blood Cells May Compromise Systemic Delivery", Molecular Therapy, 14:118-128 (2006.
Non-Final Office Action for U.S. Appl. No. 15/231,422 dated Jan. 16, 2018.
Kuhn, et al., Accession No. EF011630 , 2006.
Unique anti-cancer agent ColoAd1 enters the clinic, Human Vaccines & Immunotherapeutics 8(11) , 2012 , 1551.
Small, et al., A Phase I Trial of Intravenous CG7870, a Replication-Selective, Prostate-Specific Antigen-Targeted Oncolytic Adenovirus, for the Treatment of Hormone-Refractory, Metastatic Prostate Cancer, Molecular Therapy 14 (1) , 2006 , 107-117.
Calvo, et al., A first-in-class, first-in-human phase I study of enadenotucirev, an oncolytic Ad11/Ad3 chimeric group B adenovirus, administered intravenously in patients with metastatic epithelial tumors., J Clin Oncol 32:5s, 2014 (suppl; abstr 3103) (Correspond-

(56) References Cited

OTHER PUBLICATIONS ing Poster for Abstract 3103 is entitled: "A Phase I study of enadenotucirev, an oncolytic Ad11/Ad3 chimeric group B adenovirus, administered intravenously in patients with metastatic epithelial tumors.").

Hoffmann, et al., Efficient generation of double heterologous promoter controlled oncolytic adenovirus vectors by a single homologous recombination step in *Escherichia coli*, BMC Biotechnol. Aug. 6, 2006, 36.

Janssen, et al., Development of an AdEasy-based system to produce first- and second-generation adenoviral vectors with tropism for CAR- or CD46-positive cells, J Gene Med. 15(1), Jan. 2013, 1-11.

Li, et al., A one-step ligation system for rapid generation of armed, conditionally-replicating adenoviruses, Biotechnol Lett. 35, 2013, 1215-1221.

Boni et al, A Phase 1 Mechanism of Action Study of Intra-Tumoural (IT) or Intravenous (IV) Administration of Enadenotucirev, an Oncolytic AD11/AD3 Chimeric Group B Adenovirus in Colon Cancer Patients Undergoing Resection of Primary Tumour, Annals of Oncology 25 (supplement 4): iv361-iv372, 2014.

FUERER and IGGO, 5-Fluorocytosine increases the toxicity of Wnt-targeting replicating adenoviruses that express cytosine deaminase as a late gene, Gene Therapy (2004), 11, 142-151.

Nemunaitis, J., et al., Intravenous infusion of a replication-selective adenovirus (ONYX-015) in cancer patients: safety, feasibility and biological activity, Gene Therapy (2001) 8, 746-759.

\* cited by examiner

Figure 2  Biodistribution of 1e11 (1x10¹¹) particles of ColoAd1 in normal BalbC mice 24 hours post injection Figure 4  Clearance kinetics of ColoAd1 from primary organs liver, spleen and lungs in CD46-expressing mice followed for 65 days

* Below limit of detection

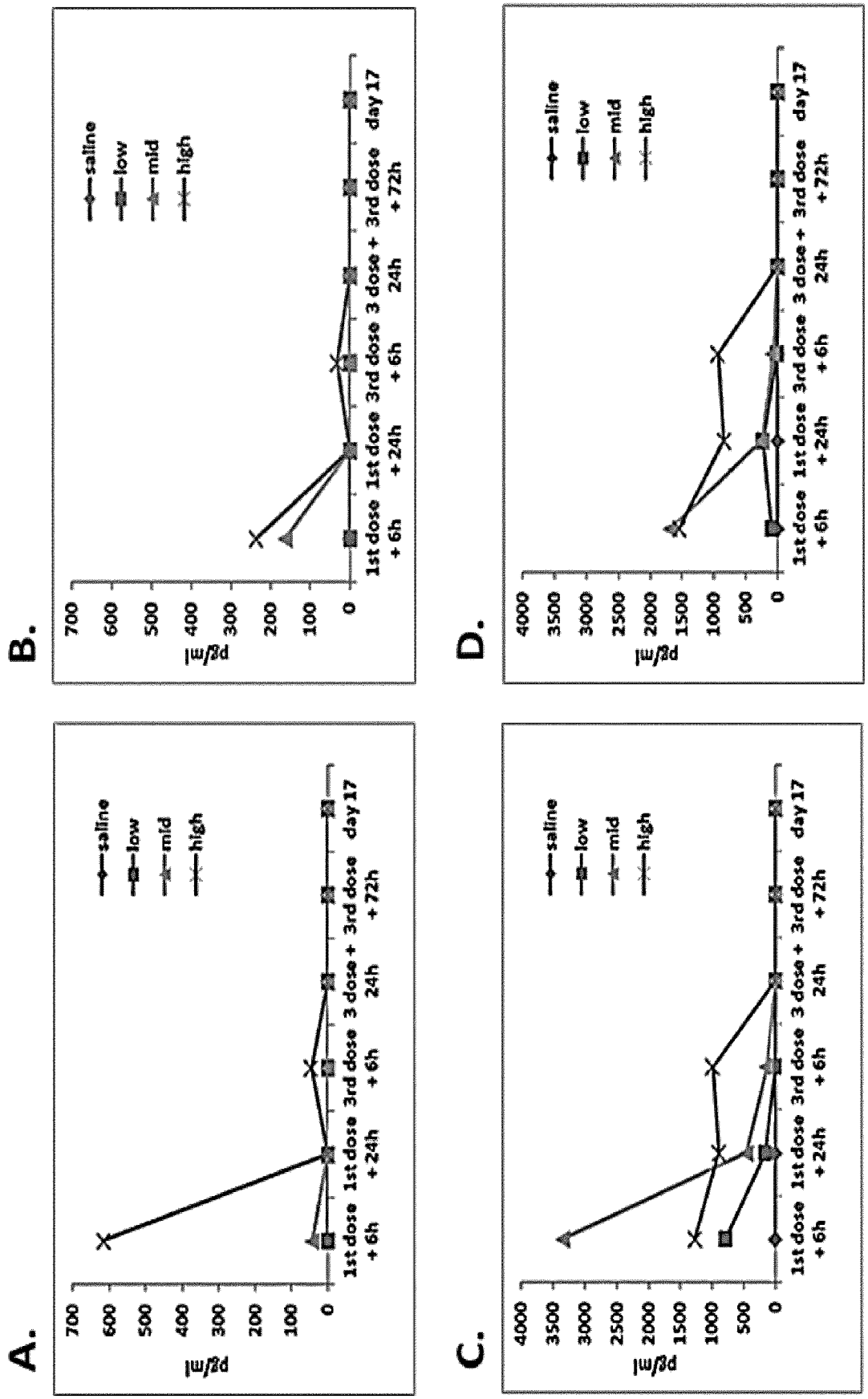
Figure 6  Cytokine levels after the first and subsequent equal therapeutic doses in a pre-clinical toxicology study in CD-1 mice:

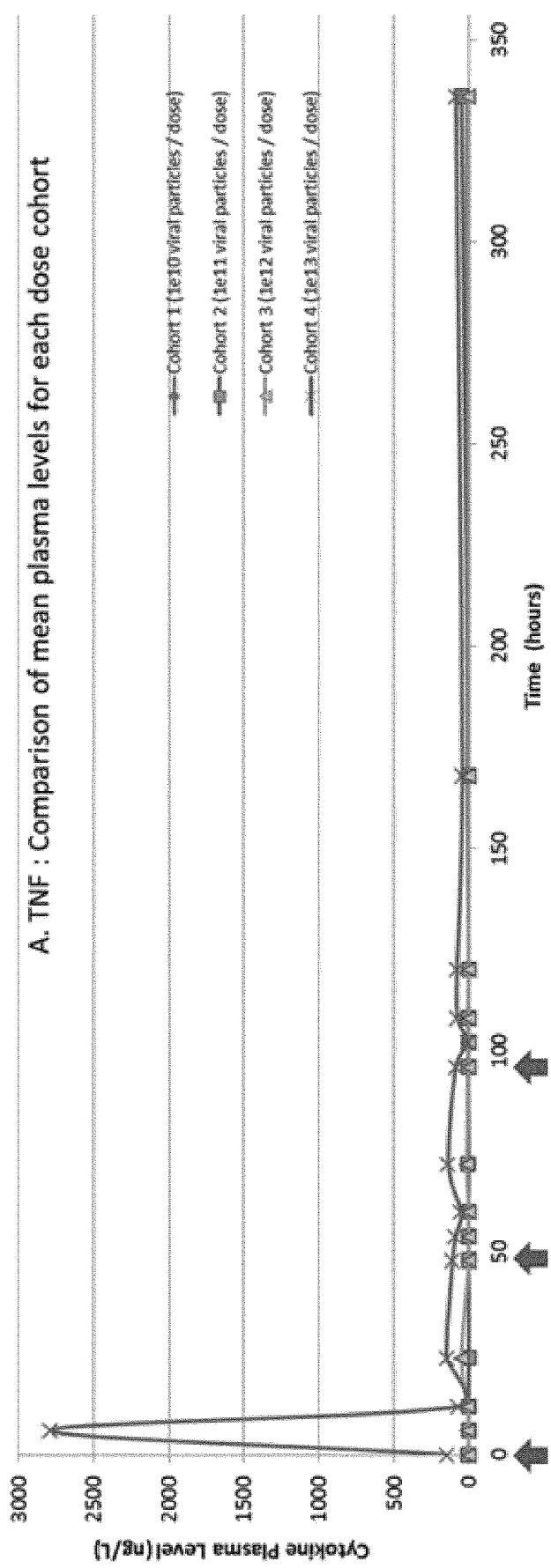
Figure 7A TNF (A) Cytokine levels (ng/L) over time in human cancer patients with metastatic solid epithelial tumours after intravenous doses of ColoAd1.

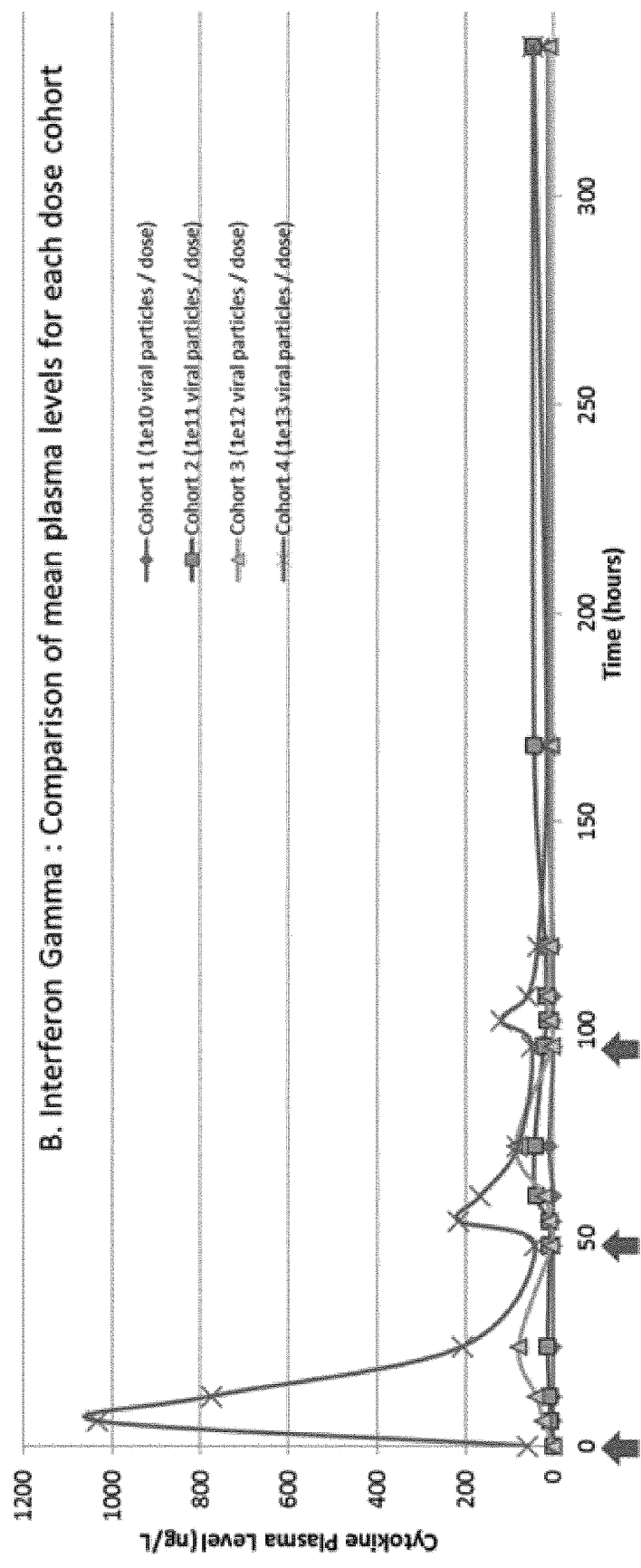
Figure 7B Ggamma interferon Cytokine levels (ng/L) over time in human cancer patients with metastatic solid epithelial tumours after intravenous doses of ColoAd1.

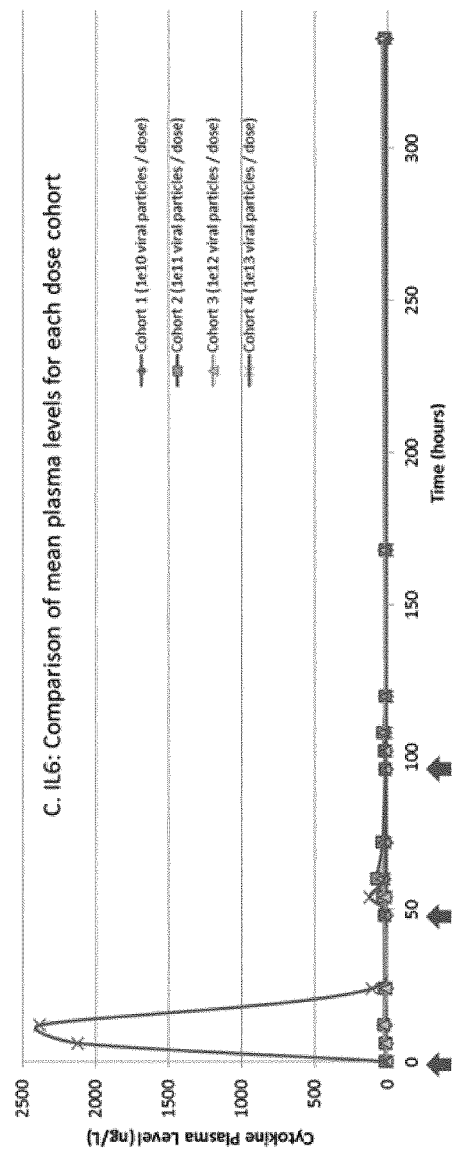
Figure 7C IL6 Cytokine levels (ng/L) over time in human cancer patients with metastatic solid epithelial tumours after intravenous doses of ColoAd1.

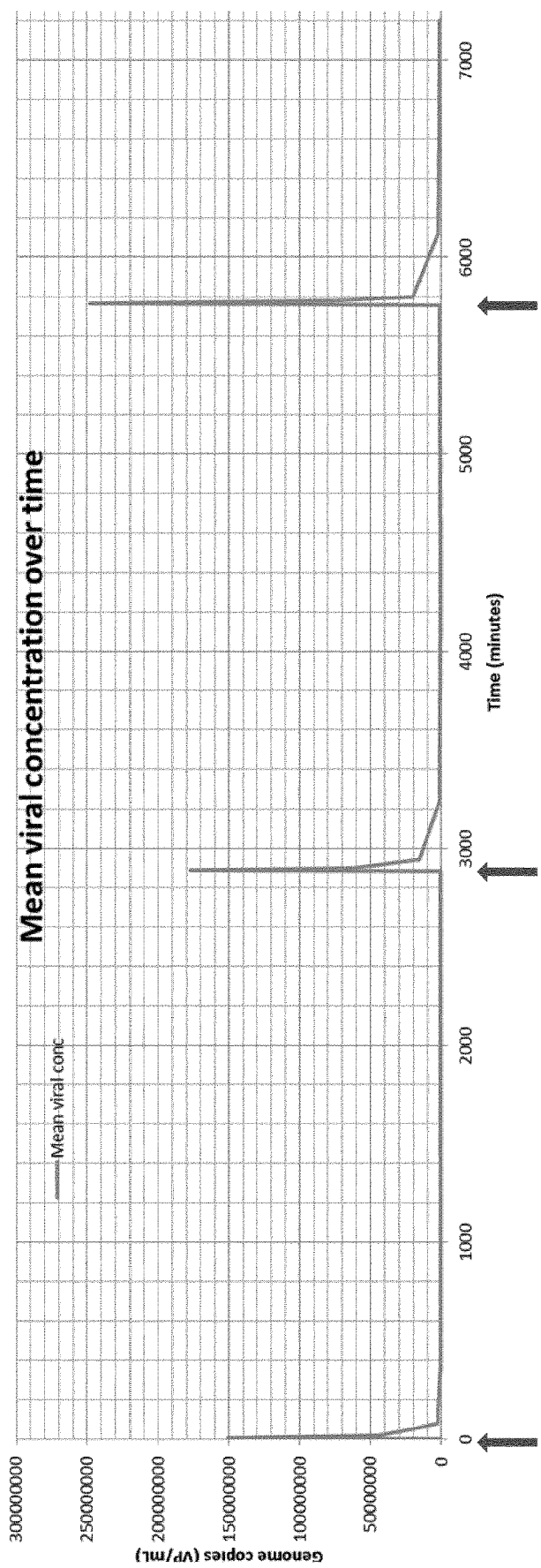
Figure 8A  Systemic pharmacokinetics of ColoAd1 (mean DNA copies per mL of blood) in 3 human cancer patients with metastatic solid epithelial tumours. Patients were dosed with 1x10$^{12}$ viral particles per dose administered at 2x10$^{11}$ viral particles/min on Days 1, 3 and 5

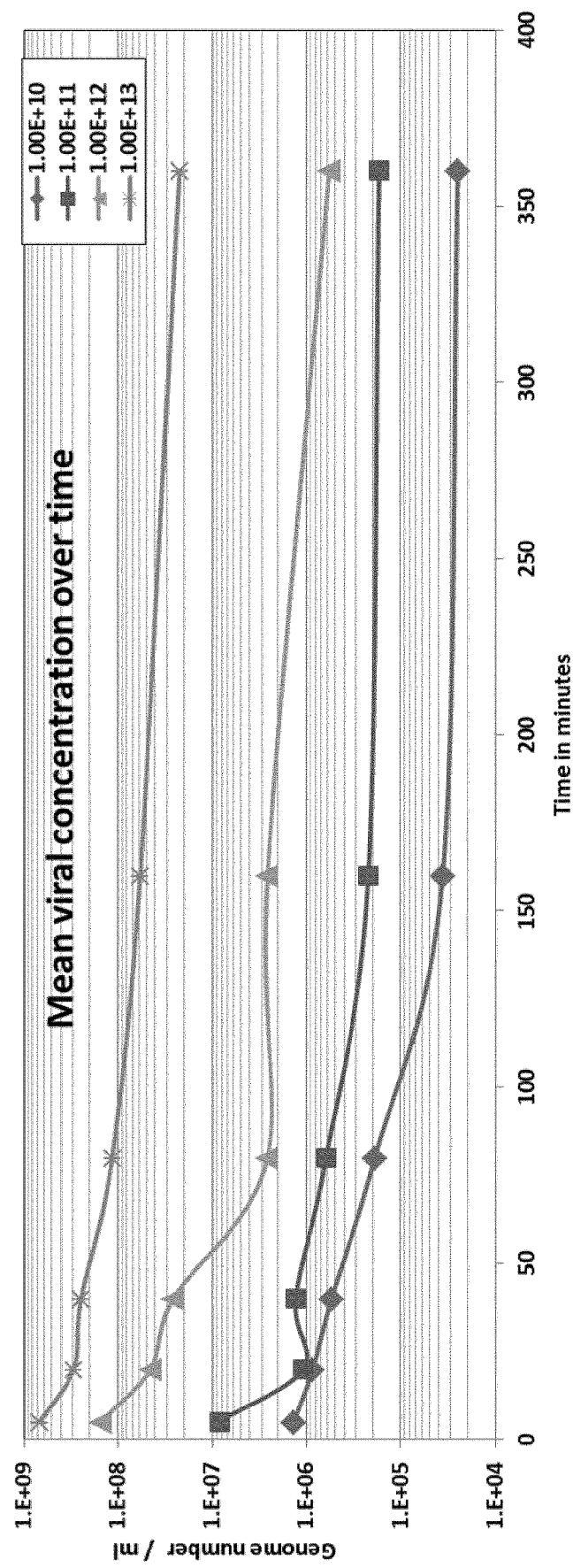

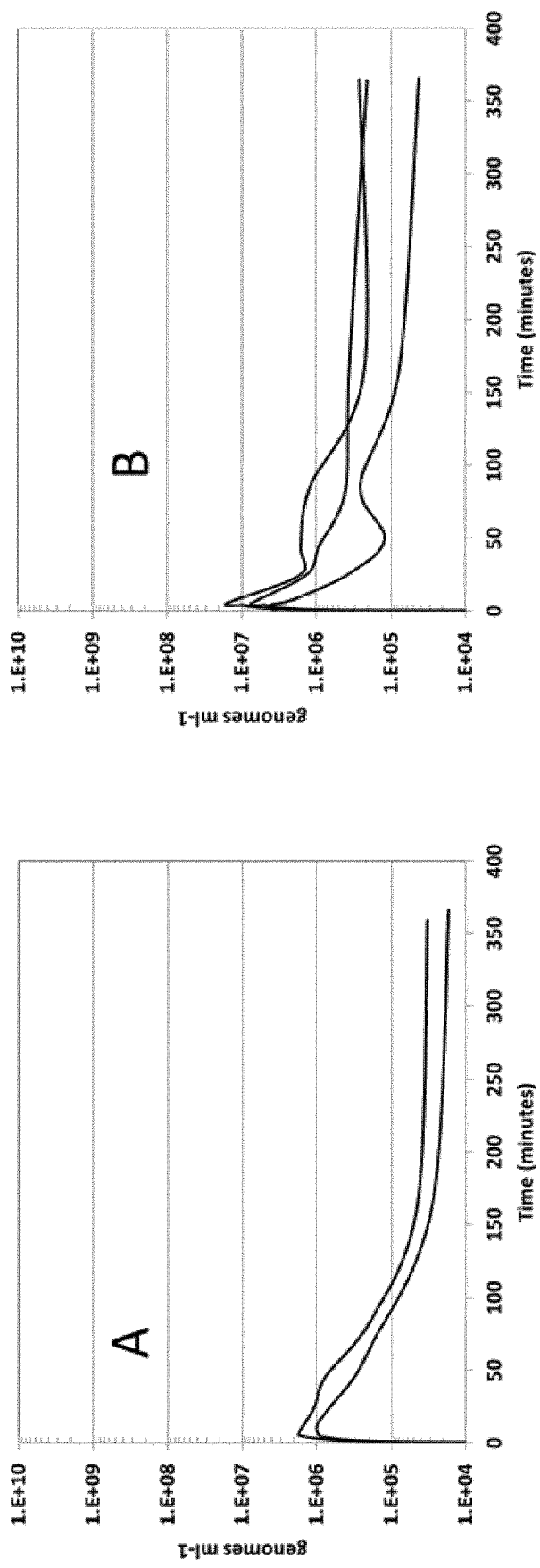
Figure 9A-B  Systemic pharmacokinetics of ColoAd1 (Genome copies per mL of blood) in human cancer patients administered with 1e10 (1x10$^{10}$) (A) and 1e11 (1x10$^{11}$) (B) ColoAd1 viral particles over 5 minutes.

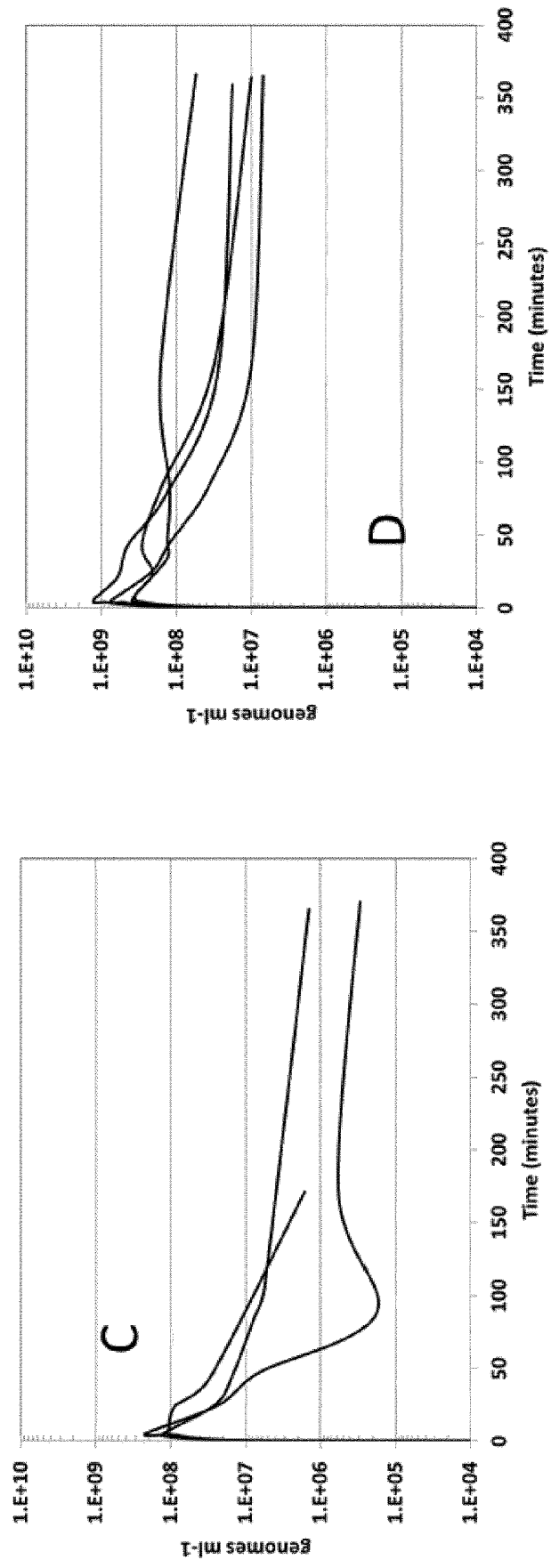
Figure 9C-D   Systemic pharmacokinetics of ColoAd1 (Genome copies per mL of blood) in human cancer patients administered with 1e12 (1x10$^{12}$) (C) and 1e13 (1x10$^{13}$) (D) ColoAd1 viral particles over 5 minutes.

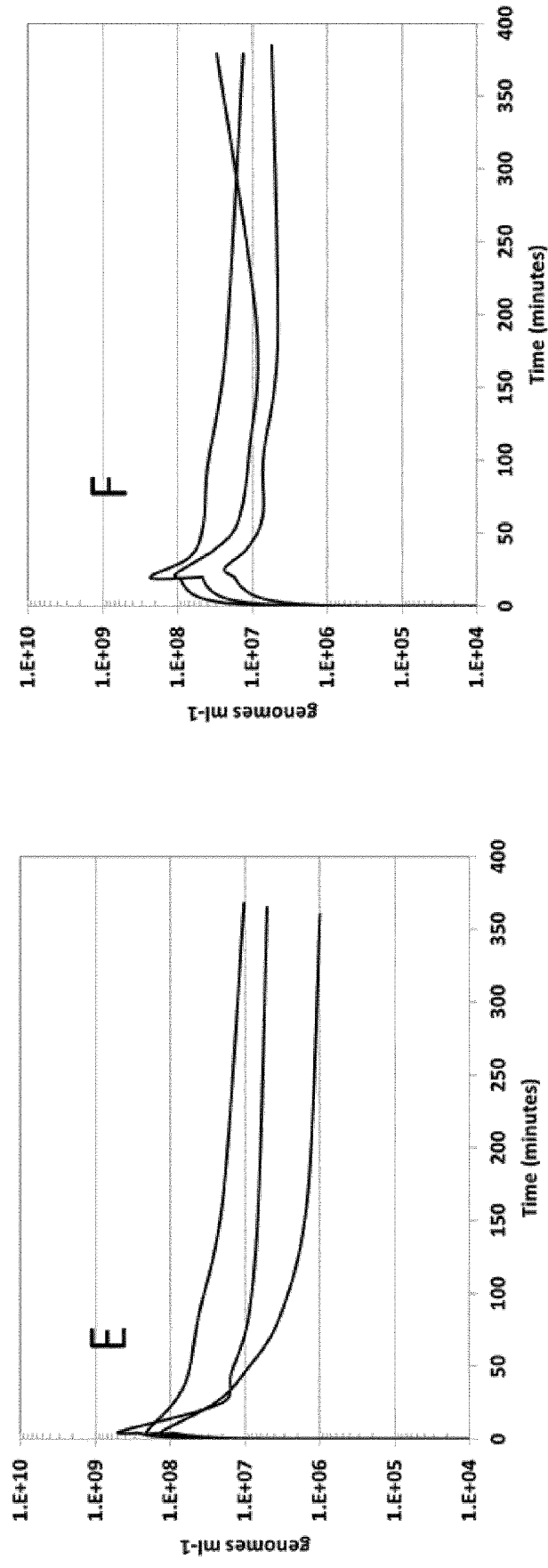
Figure 9E-F    Systemic pharmacokinetics of ColoAd1 (Genome copies per mL of blood) in human cancer patients administered with 3e12 ($3 \times 10^{12}$) (E) viral particles over 5 minutes and 3e12 ($3 \times 10^{12}$) (F) ColoAd1 viral particles over 20 minutes.

Figure 9G    Systemic pharmacokinetics of ColoAd1 (Genome copies per mL of blood) in human cancer patients administered with 6e12 ($6 \times 10^{12}$) ColoAd1 viral particles over 40 minutes.
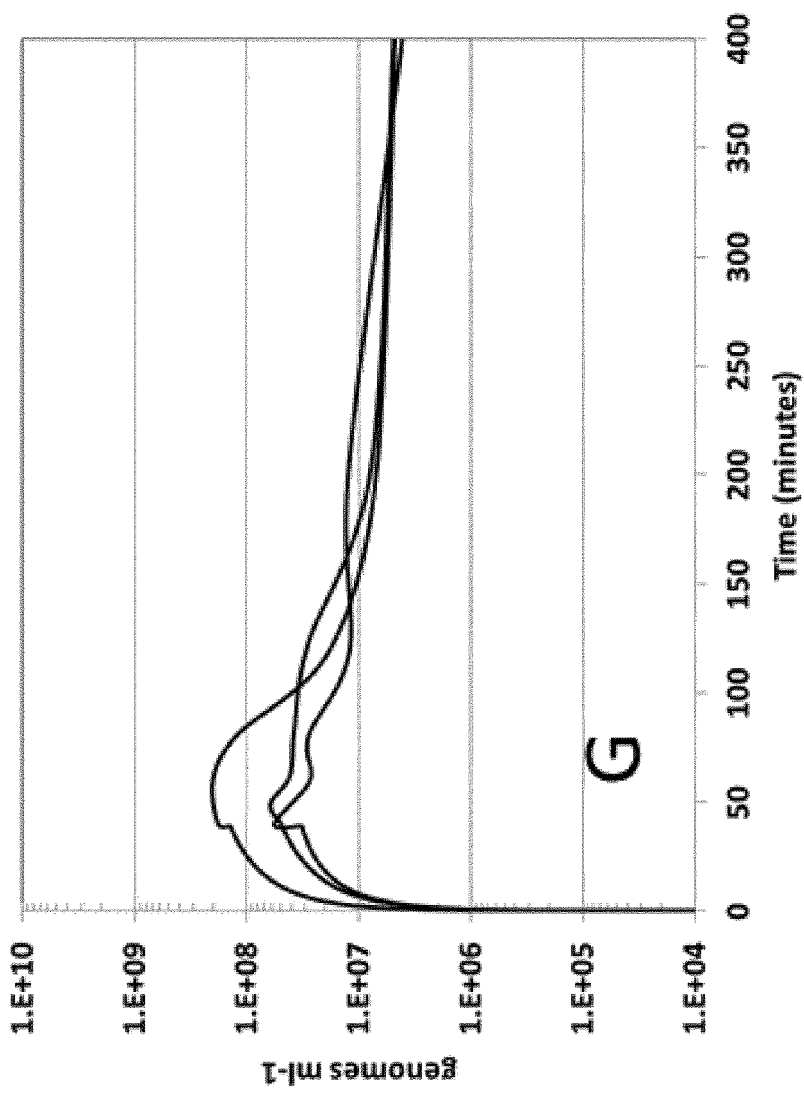

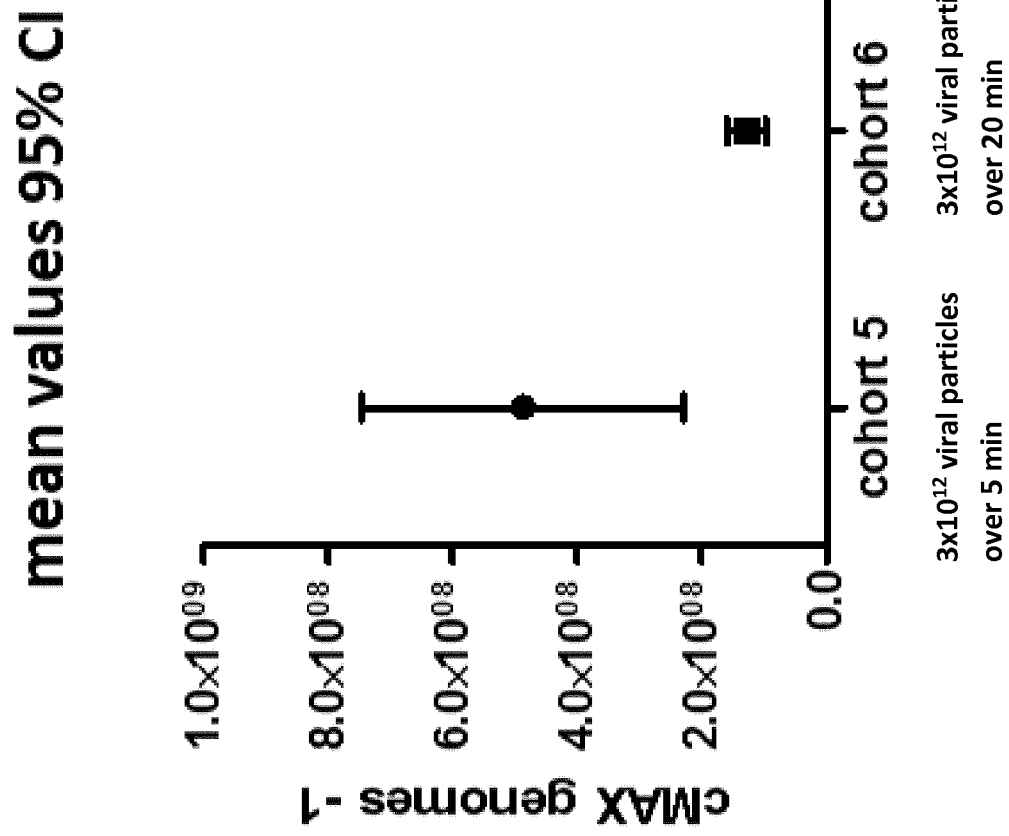
Figure 10  Slower infusion of the same dose lowers the cMax level at the end of infusion (cohort 5 vs 6)

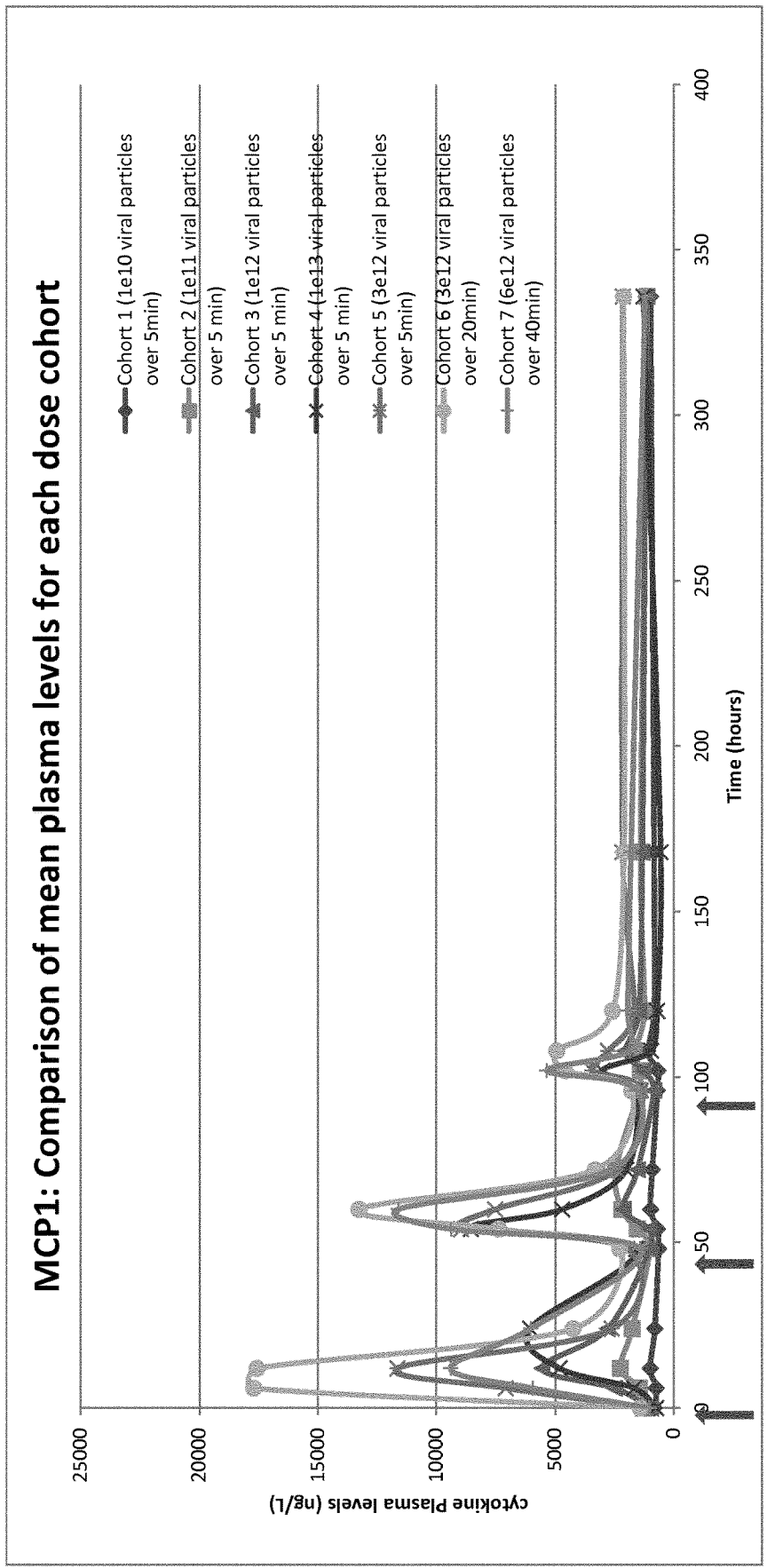
Figure 11 – Comparison of mean plasma levels of MCP1 for each dose cohort

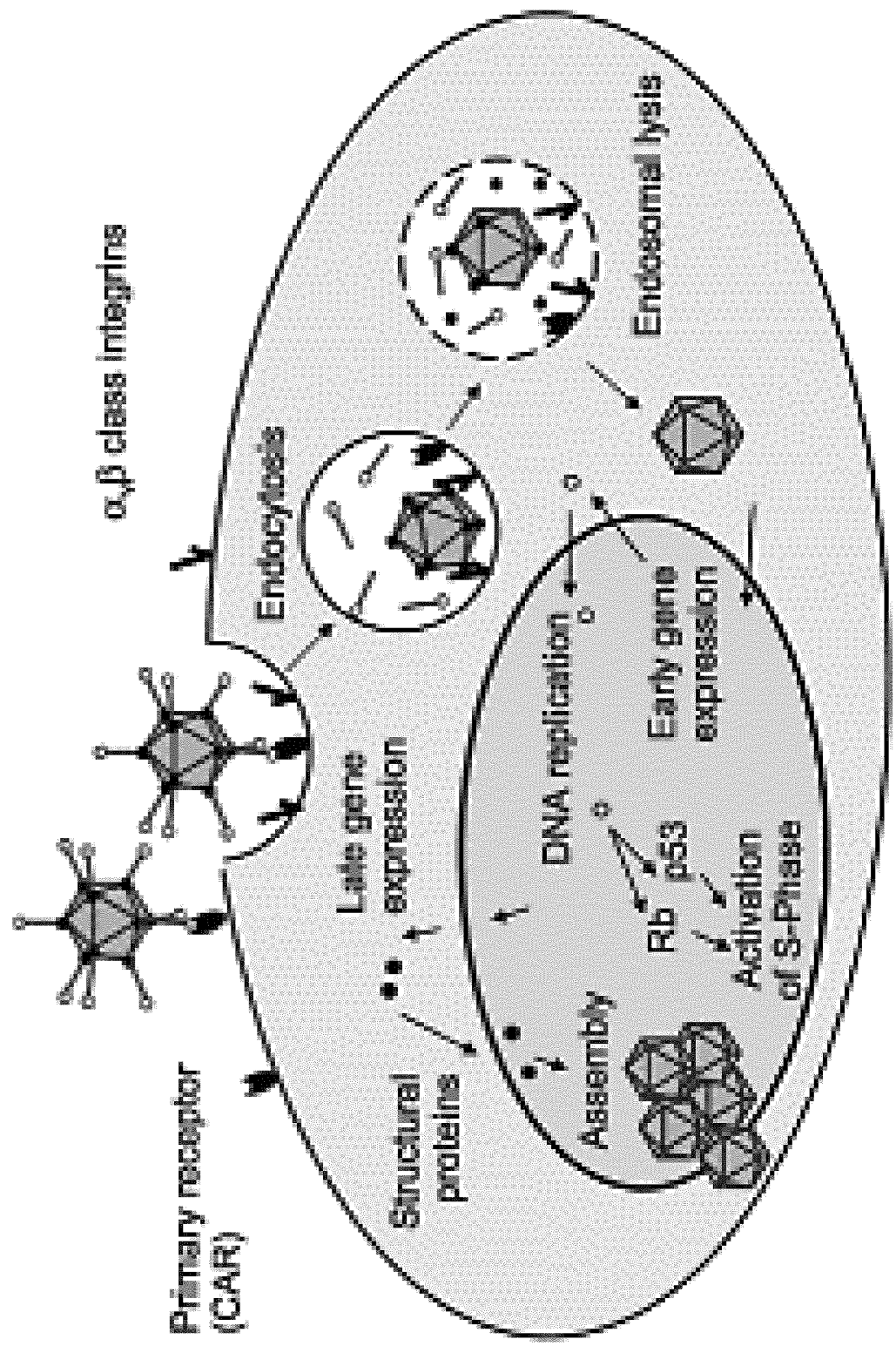
Figure 12 – ColoAd1 replication cycle

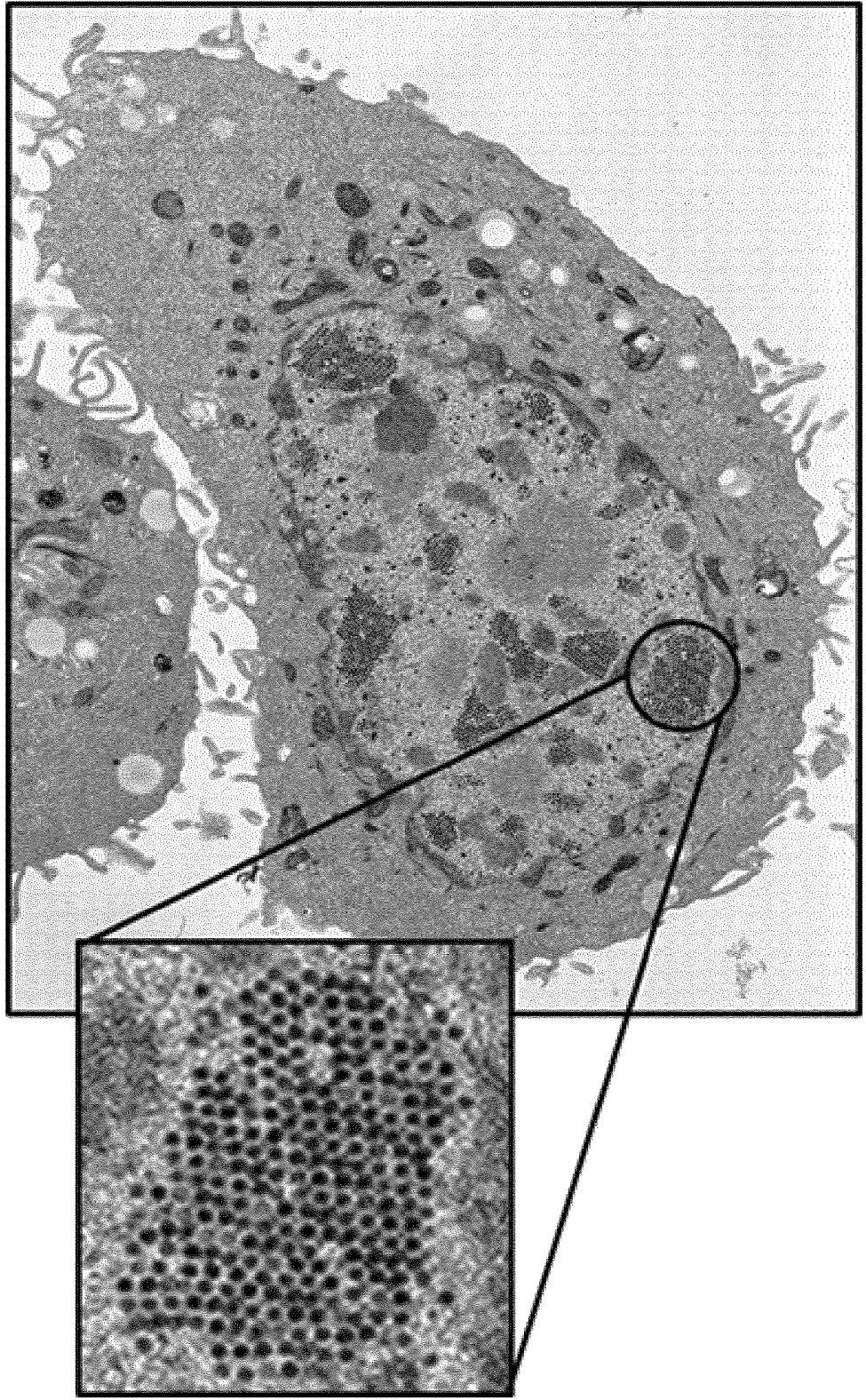
Figure 13 ColoAd1 infection of cancer cells shown as nuclear staining in a colorectal cancer cell line following in vitro infection with the virus

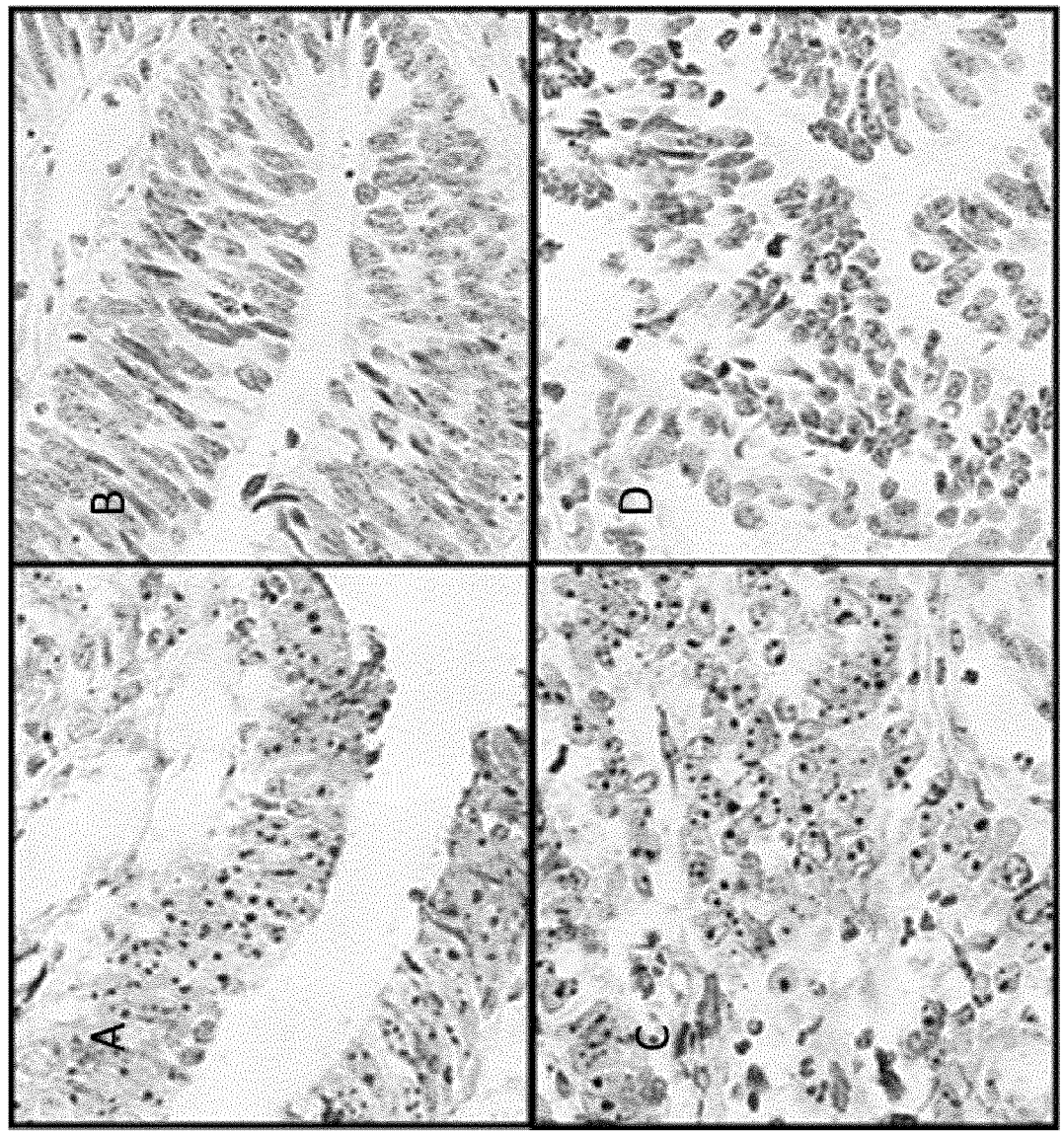
Figure 14 A-D. ColoAd1 IT administration, hexon (A) and isotype control (B) staining; ColoAd1 IV administration hexon (C) and isotype control (D) staining respectively

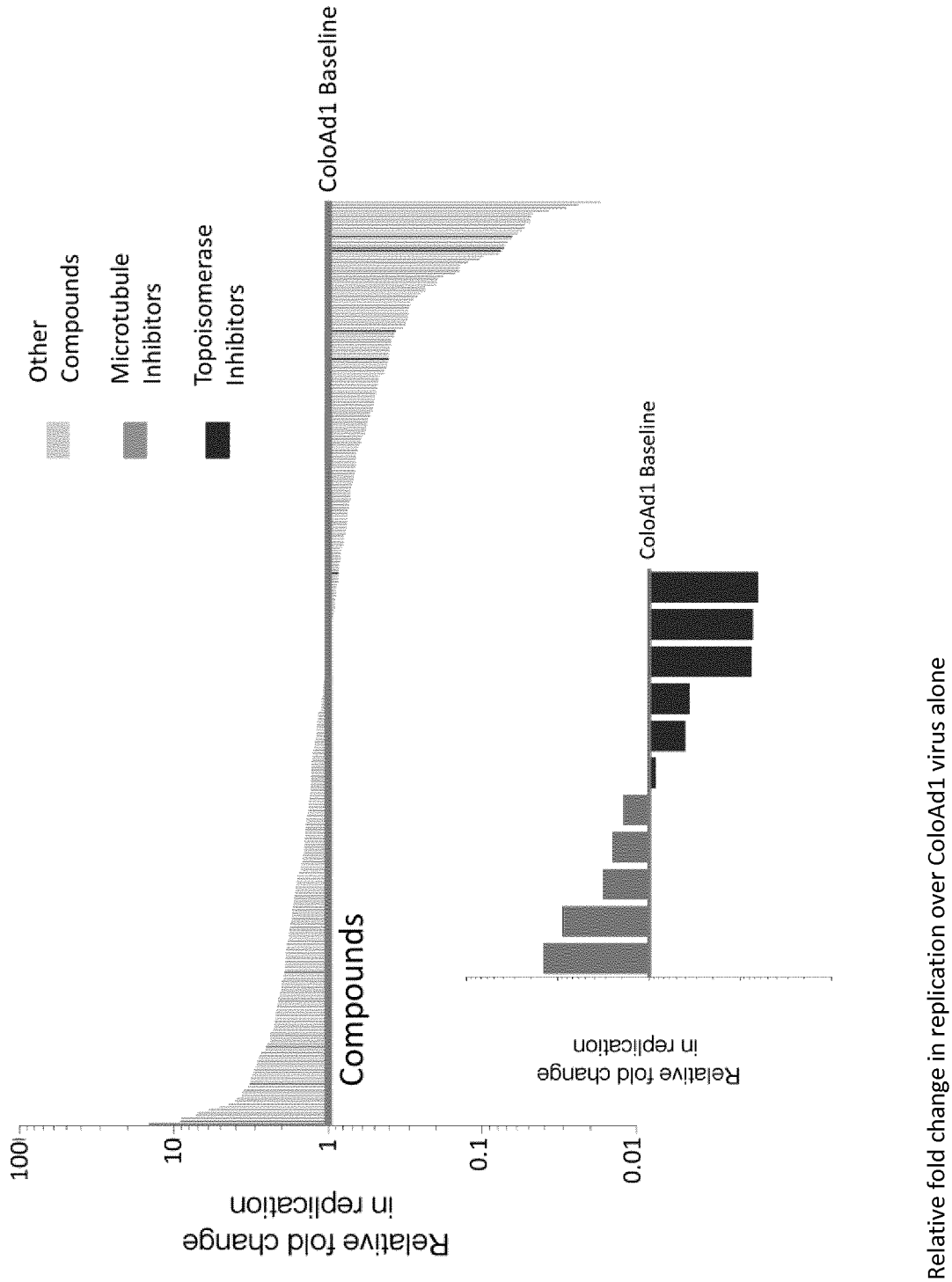
Figure 15   320 clinically approved or developed compounds were analysed for their impact on virus replication Figure 16 *In vivo* Model – Paclitaxel / ColoAd1 combination therapy (Day 33)
A - PBS
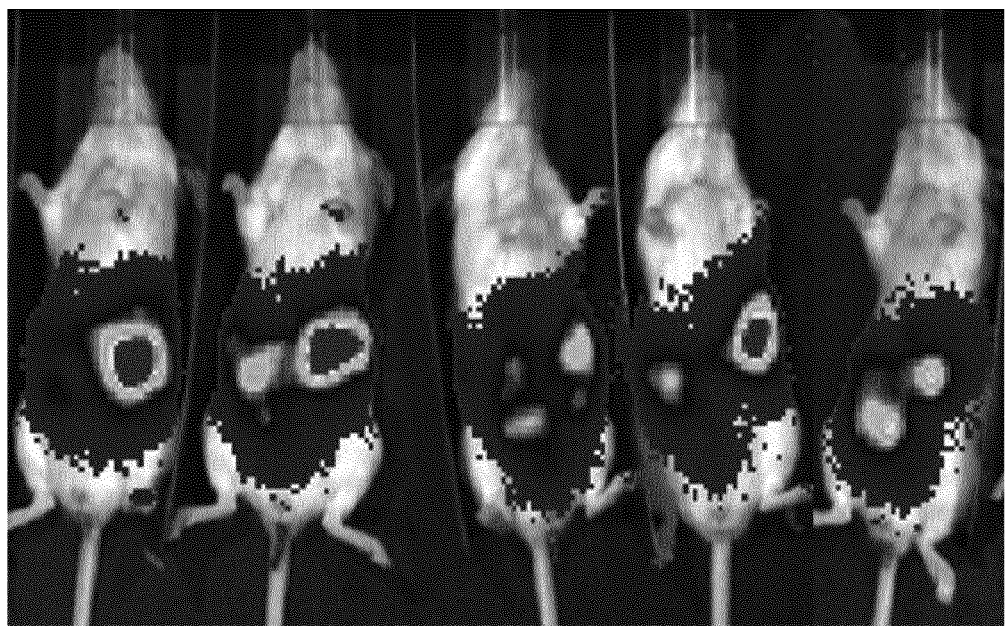
B - Paclitaxel
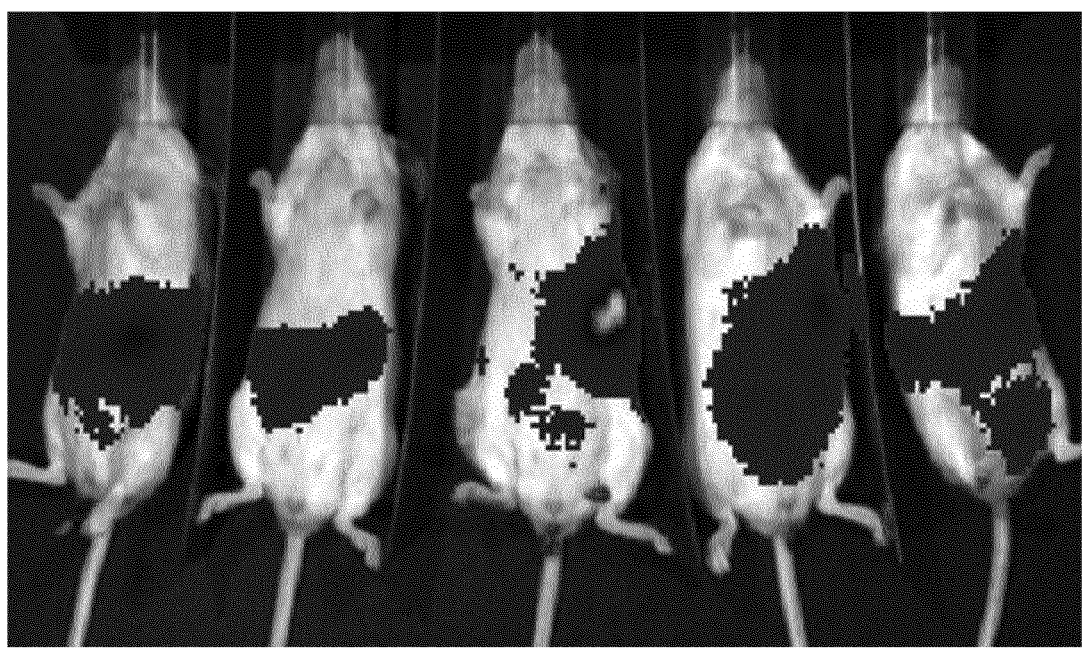

Figure 16 continued
C - ColoAd1
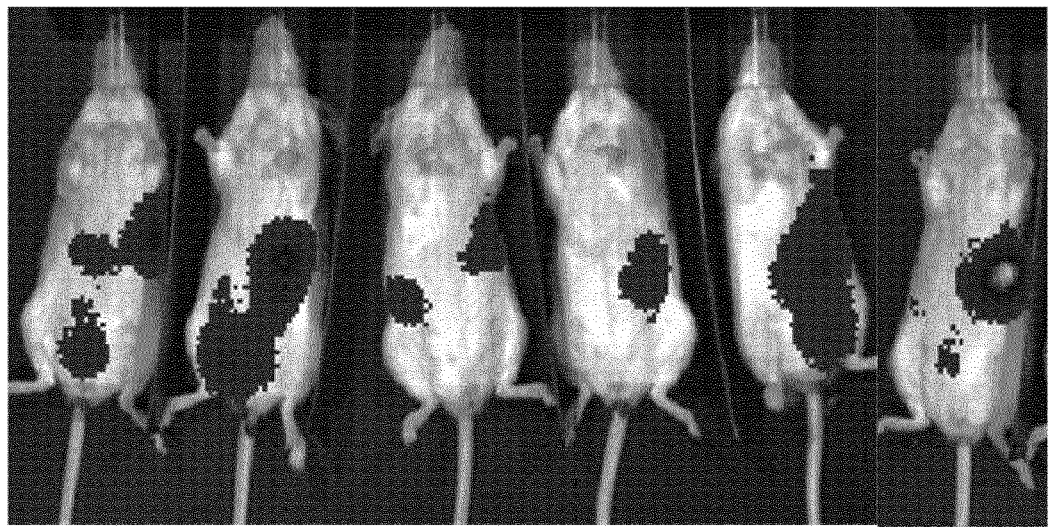
D ColoAd1 + Paclitaxel
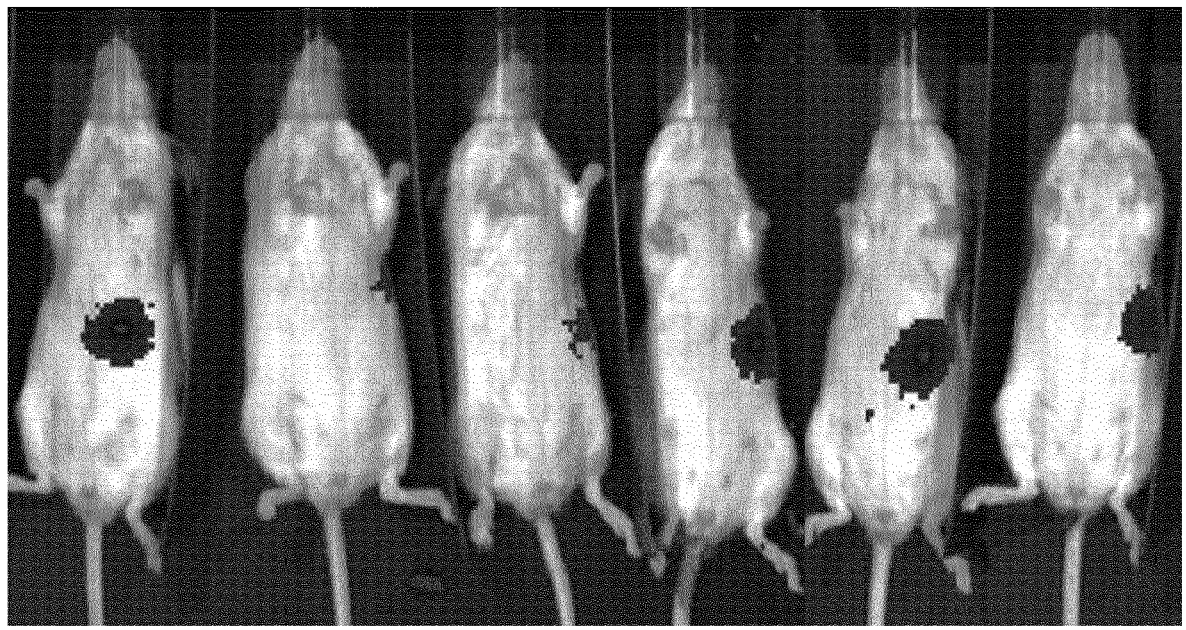

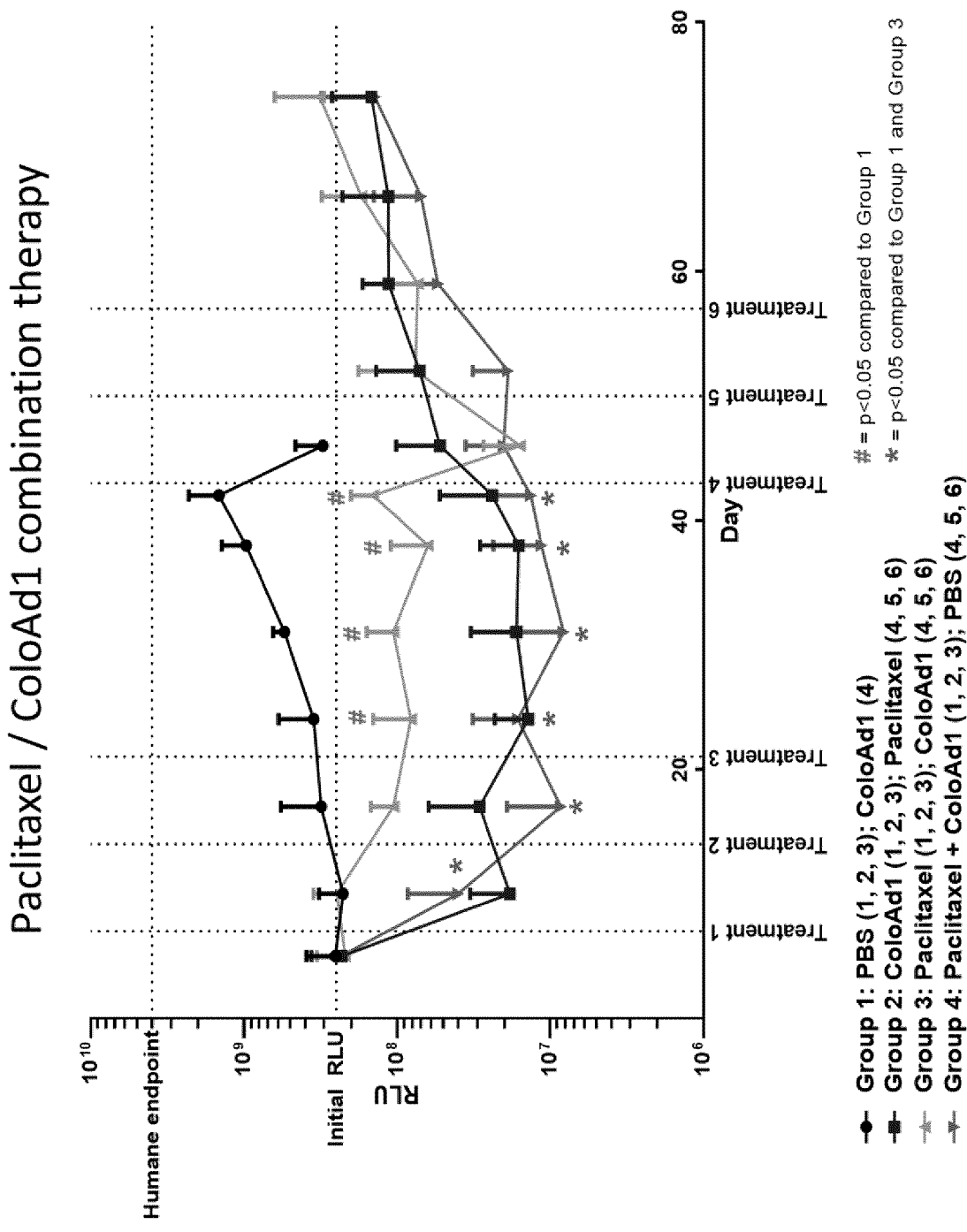
Figure 17 *In vivo* ColoAd1 / chemotherapy combination studies

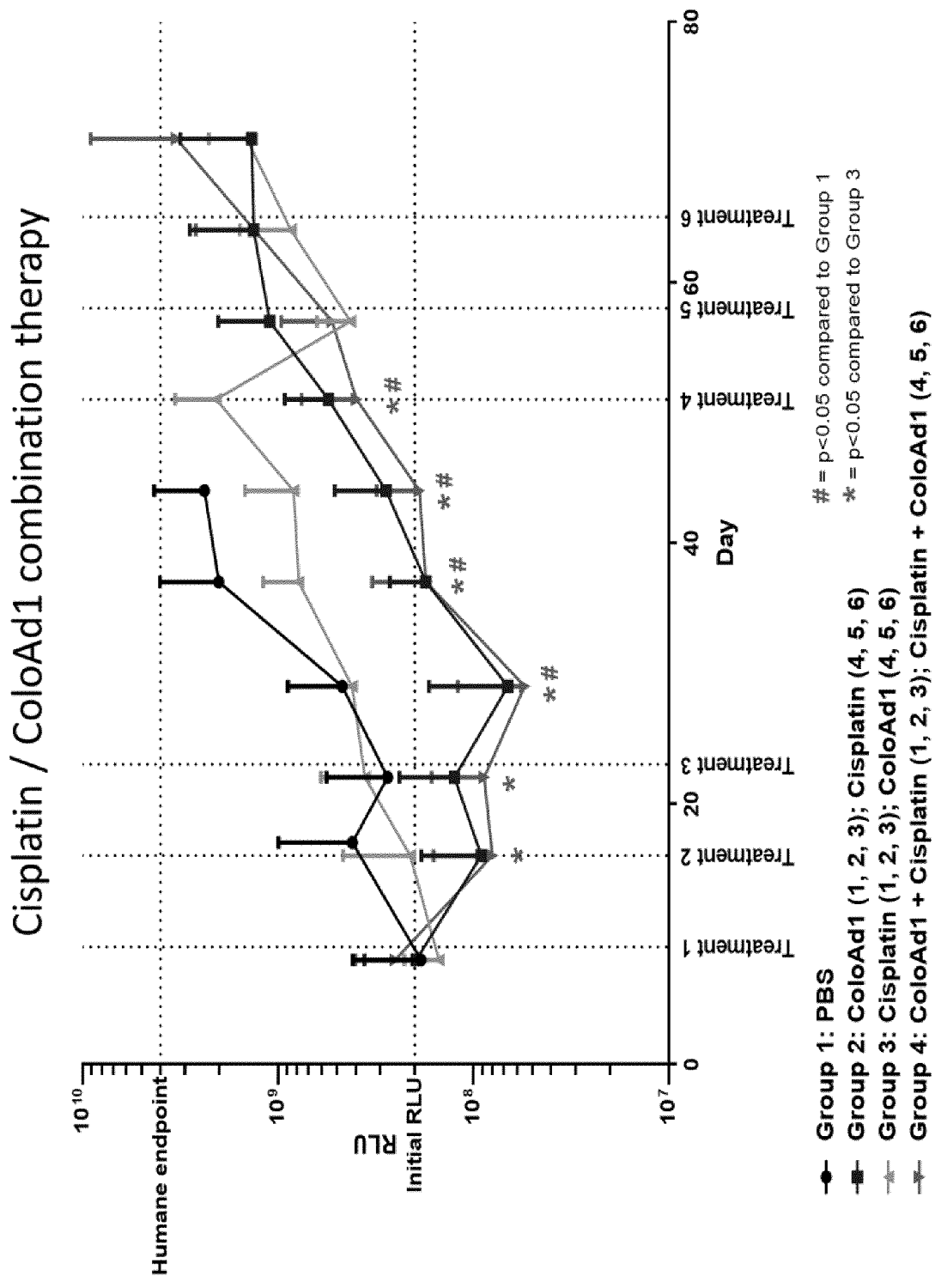
Figure 18 *In vivo* ColoAd1 / chemotherapy combination studies

SEQUENCE LISTING

```
<160> NUMBER OF SEQ ID NOS: 2

<210> SEQ ID NO 1
<211> LENGTH: 32326
<212> TYPE: DNA
<213> ORGANISM: Artificial Sequence
<220> FEATURE:
<223> OTHER INFORMATION: ColoAd1

<400> SEQUENCE: 1
tctatctata taatatacct tatagatgga atggtgccaa tatgtaaatg aggtgatttt      60
aaaaagtgtg gatcgtgtgg tgattggctg tggggttaac ggctaaaagg ggcggtgcga     120
```

```
ccgtgggaaa atgacgtttt gtggggtgg agttttttg caagttgtcg cgggaaatgt      180
gacgcataaa aaggctttt tctcacggaa ctacttagtt ttcccacggt atttaacagg     240
aaatgaggta gttttgaccg gatgcaagtg aaaattgttg attttcgcgc gaaaactgaa    300
tgaggaagtg ttttctgaa taatgtggta tttatggcag ggtggagtat ttgttcaggg     360
ccaggtagac tttgacccat tacgtggagg tttcgattac cgtgtttttt acctgaatt    420
ccgcgtaccg tgtcaaagtc ttctgttttt acgtaggtgt cagctgatcg ctagggtatt   480
tatacctcag ggtttgtgtc aagaggccac tcttgagtgc cagcgagaag agttttctcc   540
tctgcgccgg cagtttaata ataaaaaaat gagagatttg cgatttctgc ctcaggaaat   600
aatctctgct gagactggaa atgaaatatt ggagcttgtg gtgcacgccc tgatgggaga   660
cgatccggag ccacctgtgc agcttttga gcctcctacg cttcaggaac tgtatgattt    720
agaggtagag ggatcggagg attctaatga ggaagctgta aatggctttt ttaccgattc   780
tatgctttta gctgctaatg aagggttaga attagatccg cctttggaca cttttgatac   840
tccagggta attgtggaaa gcggtacagg tgtaagaaaa ttacctgatt tgagttccgt    900
ggactgtgat ttgcactgct atgaagacgg gtttcctccg agtgatgagg aggaccatga   960
aaaggagcag tccatgcaga ctgcagcggg tgagggagtg aaggctgcca atgttggttt  1020
tcagttggat tgcccggagc ttcctggaca tggctgtaag tcttgtgaat tcacaggaa   1080
aaatactgga gtaaaggaac tgttatgttc gctttgttat atgagaacgc actgccactt  1140
tatttacagt aagtgtgttt aagttaaaat ttaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gaccttttgga cttgagtaca cggaaacgtc caagacaata  1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga cttttttgaag  1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc agggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg aagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
```

```
ggctgaggtg gtaatagata ctcaagacaa ggcagttatt agatgctgca tgatggatat    2580
gtggcctggg gtagtcggta tggaagcagt aacttttgta aatgttaagt ttaggggaga    2640
tggttataat ggaatagtgt ttatggccaa taccaaactt atattgcatg gttgtagctt    2700
ttttggtttc aacaatacct gtgtagatgc ctggggacag gttagtgtac ggggatgtag    2760
tttctatgcg tgttggattg ccacagctgg cagaaccaag agtcaattgt ctctgaagaa    2820
atgcatattt caaagatgta acctgggcat tctgaatgaa ggcgaagcaa gggtccgcca    2880
ctgcgcttct acagatactg gatgttttat tttgattaag ggaaatgcca gcgtaaagca    2940
taacatgatt tgcggtgctt ccgatgagag gccttatcaa atgctcactt gtgctggtgg    3000
gcattgtaat atgctggcta ctgtgcatat tgtttcccat caacgcaaaa aatggcctgt    3060
ttttgatcac aatgtgatga cgaagtgtac catgcatgca ggtgggcgta gaggaatgtt    3120
tatgccttac cagtgtaaca tgaatcatgt gaaagtgttg ttggaaccag atgccttttc    3180
cagaatgagc ctaacaggaa tttttgacat gaacatgcaa atctggaaga tcctgaggta    3240
tgatgatacg agatcgaggg tacgcgcatg cgaatgcgga ggcaagcatg ccaggttcca    3300
gccggtgtgt gtagatgtga ctgaagatct cagaccggga catttggtta ttgcccgcac    3360
tggagcagag ttcggatcca gtggagaaga aactgactaa ggtgagtatt gggaaaactt    3420
tggggtggga ttttcagatg gacagattga gtaaaaattt gttttttctg tcttgcagct    3480
gtcatgagtg gaaacgcttc ttttaagggg ggagtcttca gcccttatct gacagggcgt    3540
ctcccatcct gggcaggagt tcgtcagaat gttatgggat ctactgtgga tggaagaccc    3600
gtccaacccg ccaattcttc aacgctgacc tatgctactt taagttcttc accttttggac   3660 gcagctgcag ctgccgccgc cgcttctgtt gccgctaaca ctgtgcttgg aatgggttac    3720
tatggaagca tcatggctaa ttccacttcc tctaataacc cttctaccct gactcaggac    3780
aagttacttg tccttttggc ccagctggag gctttgaccc aacgtctggg tgaacttttct   3840 cagcaggtgg tcgagttgcg agtacaaact gagtctgctg tcggcacggc aaagtctaaa    3900
taaaaaaatc ccagaatcaa tgaataaata aacaagcttg ttgttgattt aaaatcaagt    3960
gtttttattt cattttcgc gcacggtatg ccctagacca ccgatctcta tcattgagaa     4020
ctcggtggat ttttccagg atcctataga ggtgggattg aatgtttaga tacatgggca     4080
ttaggccgtc tttggggtgg agatagctcc attgaaggga ttcatgctcc ggggtagtgt    4140
tgtaaatcac ccagtcataa caaggtcgca gtgcatggtg ttgcacaata tcttttagaa    4200
gtaggctgat tgccacagat aagcccttgg tgtaggtgtt tacaaaccgg ttgagctggg    4260
atgggtgcat tcggggtgaa attatgtgca ttttggattg gattttttaag ttggcaatat   4320 tgccgccaag atcccgtctt gggttcatgt tatgaaggac caccaagacg gtgtatccgg    4380
tacatttagg aaatttatcg tgcagcttgg atggaaaagc gtggaaaaat ttggagacac    4440
ccttgtgtcc tccaagattt tccatgcact catccatgat aatagcaatg gggccgtggg    4500
cagcggcgcg ggcaaacacg ttccgtgggt ctgacacatc atagttatgt tcctgagtta    4560
aatcatcata agccatttta atgaatttgg ggcggagagt accagattgg ggtatgaatg    4620
ttccttcggg ccccggagca tagttcccct cacagatttg catttcccaa gctttcagtt    4680
ccgagggtgg aatcatgtcc acctgggggg ctatgaaaaa caccgtttct ggggcggggg    4740
tgattaattg tgatgatagc aaatttctga gcaattgaga tttgccacat ccggtggggc    4800
cataaatgat tccgattacg ggttgcaggt ggtagtttag ggaacggcaa ctgccgtctt    4860
```

-continued

```
ctcgaagcaa gggggccacc tcgttcatca tttcccttac atgcatattt tcccgcacca    4920
aatccattag gaggcgctct cctcctagtg atagaagttc ttgtagtgag gaaaagtttt    4980
tcagcggttt cagaccgtca gccatgggca ttttggagag agtttgctgc aaaagttcta    5040
gtctgttcca cagttcagtg atgtgttcta tggcatctcg atccagcaga cctcctcgtt    5100
tcgcgggttt ggacggctcc tggaataggg tatgagacga tgggcgtcca gcgctgccag    5160
ggttcggtcc ttccagggtc tcagtgttcg agtcagggtt gtttccgtca cagtgaaggg    5220
gtgtgcgcct gcttgggcgc ttgccagggt gcgcttcaga ctcatcctgc tggtcgaaaa    5280
cttctgtcgc ttggcgccct gtatgtcggc caagtagcag tttaccatga gttcgtagtt    5340
gagcgcctcg gctgcgtggc ctttggcgcg agcttacct ttggaagttt tcttgcatac     5400
cgggcagtat aggcatttca gcgcatacaa cttgggcgca aggaaaacgg attctgggga    5460
gtatgcatct gcgccgcagg aggcgcaaac agtttcacat tccaccagcc aggttaaatc    5520
cggttcattg gggtcaaaaa caagttttcc gccatatttt ttgatgcgtt tcttaccttt    5580
ggtctccatg agttcgtgtc ctcgttgagt gacaaacagg ctgtccgtgt ccccgtagac    5640
tgattttaca ggcctcttct ccagtggagt gcctcggtct tcttcgtaca ggaactctga    5700
ccactctgat acaaaggcgc gcgtccaggc cagcacaaag gaggctatgt gggagggta     5760
gcgatcgttg tcaaccaggg ggtccacctt ttccaaagta tgcaaacaca tgtcaccctc    5820
ttcaacatcc aggaatgtga ttggcttgta ggtgtatttc acgtgacctg ggtccccgc     5880
tgggggggta taaaaggggg cggttctttg ctcttcctca ctgtcttccg gatcgctgtc    5940
caggaacgtc agctgttggg gtaggtattc cctctcgaag gcgggcatga cctctgcact    6000
caggttgtca gtttctaaga acgaggagga tttgatattg acagtgccgg ttgagatgcc    6060
tttcatgagg ttttcgtcca tctggtcaga aaacacaatt tttttattgt caagtttggt    6120
ggcaaatgat ccatacaggg cgttggataa agtttggca atggatcgca tggtttggtt     6180
ctttccttg tccgcgcgct ctttggcggc gatgttgagt tggacatact cgcgtgccag     6240
gcacttccat tcggggaaga tagttgttaa ttcatctggc acgattctca cttgccaccc    6300
tcgattatgc aagtaatta aatccacact ggtggccacc tcgcctcgaa ggggttcatt     6360
ggtccaacag agcctacctc ctttcctaga acagaaaggg ggaagtgggt ctagcataag    6420
ttcatcggga gggtctgcat ccatggtaaa gattcccgga agtaaatcct tatcaaaata    6480
gctgatggga gtggggtcat ctaaggccat ttgccattct cgagctgcca gtgcgcgctc    6540
atatgggtta aggggactgc cccatggcat gggatgggtg agtgcagagg catacatgcc    6600
acagatgtca tagacgtaga tgggatcctc aaagatgcct atgtaggttg atagcatcg     6660
ccccctctg atacttgctc gcacatagtc atatagttca tgtgatggcg ctagcagccc     6720
cggacccaag ttggtgcgat tgggtttttc tgttctgtag acgatctggc gaaagatggc    6780
gtgagaattg gaagagatgg tgggtctttg aaaaatgttg aaatgggcat gaggtagacc    6840
tacagagtct ctgacaaagt gggcataaga ttcttgaagc ttggttacca gttcggcggt    6900
gacaagtacg tctagggcgc agtagtcaag tgtttcttga atgatgtcat aacctggttg    6960
gttttctttt tccacagtt cgcggttgag aaggtattct tcgcgatcct tccagtactc     7020
ttctagcgga aacccgtctt tgtctgcacg gtaagatcct agcatgtaga actgattaac    7080
tgccttgtaa gggcagcagc ccttctctac gggtagagag tatgcttgag cagcttttcg    7140
tagcgaagcg tgagtaaggg caaaggtgtc tctgaccatg actttgagga attggtattt    7200
gaagtcgatg tcgtcacagg ctccctgttc ccagagttgg aagtctaccc gtttcttgta    7260
```

```
ggcggggttg ggcaaagcga aagtaacatc attgaagaga atcttgccgg ccctgggcat    7320
gaaattgcga gtgatgcgaa aaggctgtgg tacttccgct cggttattga taacctgggc    7380
agctaggacg atctcgtcga aaccgttgat gttgtgtcct acgatgtata attctatgaa    7440
acgcggcgtg cctctgacgt gaggtagctt actgagctca tcaaaggtta ggtctgtggg    7500
gtcagataag gcgtagtgtt cgagagccca ttcgtgcagg tgaggattcg ctttaaggaa    7560
ggaggaccag aggtccactg ccagtgctgt ttgtaactgg tcccggtact gacgaaaatg    7620
ccgtccgact gccatttttt ctggggtgac gcaatagaag gtttgggggt cctgccgcca    7680
gcgatcccac ttgagtttta tggcgaggtc ataggcgatg ttgacgagcc gctggtctcc    7740
agagagtttc atgaccagca tgaaggggat tagctgcttg ccaaaggacc ccatccaggt    7800
gtaggtttcc acatcgtagg tgagaaagag cctttctgtg cgaggatgag agccaatcgg    7860
gaagaactgg atctcctgcc accagttgga ggaatggctg ttgatgtgat ggaagtagaa    7920
ctccctgcga cgcgccgagc attcatgctt gtgcttgtac agacggccgc agtagtcgca    7980
gcgttgcacg ggttgtatct cgtgaatgag ttgtacctgg cttcccttga cgagaaattt    8040
cagtgggaag ccgaggcctg gcgattgtat ctcgtgcttt actatgttgt ctgcatcggc    8100
ctgttcatct tctgtctcga tggtggtcat gctgacgagc cctcgcggga ggcaagtcca    8160
gacctcggcg cggcagggc ggagctcgag gacgagagcg cgcaggctgg agctgtccag    8220
ggtcctgaga cgctgcggac tcaggttagt aggcagtgtc aggagattaa cttgcatgat    8280
cttttggagg gcgtgcggga ggttcagata gtacttgatc tcaacgggtc cgttggtgga    8340
gatgtcgatg gcttgcaggg ttccgtgtcc cttgggcgct accaccgtgc ccttgttttt    8400
cattttggac ggcggtggct ctgttgcttc ttgcatgttt agaagcggtg tcgagggcgc    8460
gcaccgggcg gcagggcgg ctcggacccc ggcggcatgg ctggcagtgg tacgtcggcg    8520
ccgcgcgcgg gtaggttctg gtactgcgcc ctgagaagac tcgcatgcgc gacgacgcgg    8580
cggttgacat cctggatctg acgcctctgg gtgaaagcta ccggcccgt gagcttgaac     8640 ctgaaagaga gttcaacaga atcaatctcg gtatcgttga cggcggcttg cctaaggatt    8700
tcttgcacgt caccagagtt gtcctggtag gcgatctccg ccatgaactg ctcgatctct    8760
tcctcttgaa gatctccgcg gcccgctctc tcgacggtgg ccgcgaggtc gttggagatg    8820
cgcccaatga gttgagagaa tgcattcatg cccgcctcgt tccagacgcg gctgtagacc    8880 acggcccca cgggatctct cgcgcgcatg accacctggg cgaggttgag ctccacgtgg    8940
cgggtgaaga ccgcatagtt gcataggcgc tggaaaaggt agttgagtgt ggtggcgatg    9000
tgctcggtga cgaagaaata catgatccat cgtctcagcg gcatctcgct gacatcgccc    9060
agagcttcca agcgctccat ggcctcgtag aagtccacgc caaaattaaa aaactgggag    9120
tttcgcgcgg acacggtcaa ctcctcttcc agaagacgga taagttcggc gatggtggtg    9180
cgcacctcgc gctcgaaagc ccctgggatt tcttcctcaa tctcttcttc ttccactaac    9240
atctcttcct cttcaggtgg ggctgcagga ggaggggaa cgcggcgacg ccggcggcgc    9300
acgggcagac ggtcgatgaa tctttcaatg acctctccgc ggcggcggcg catggtttca    9360
gtgacggcgc ggccgttctc gcgcggtcgc agagtaaaaa caccgccgcg catctcctta    9420
aagtggtgac tgggaggttc tccgtttggg agggagaggg cgctgattat acattttatt    9480
aattggcccg tagggactgc acgcagagat ctgatcgtgt caagatccac gggatctgaa    9540 aaccttcga cgaaagcgtc taaccagtca cagtcacaag gtaggctgag tacggcttct    9600
```

```
tgtgggcggg ggtggttatg tgttcggtct gggtcttctg tttcttcttc atctcgggaa    9660
ggtgagacga tgctgctggt gatgaaatta aagtaggcag ttctaagacg gcggatggtg    9720
gcgaggagca ccaggtcttt gggtccggct tgctggatac gcaggcgatt ggccattccc    9780
caagcattat cctgacatct agcaagatct ttgtagtagt cttgcatgag ccgttctacg    9840
ggcacttctt cctcacccgt tctgccatgc atacgtgtga gtccaaatcc gcgcattggt    9900
tgtaccagtg ccaagtcagc tacgactctt cggcgagga tggcttgctg tacttgggta     9960
agggtggctt gaaagtcatc aaaatccaca aagcggtggt aagctcctgt attaatggtg   10020
taagcacagt tggccatgac tgaccagtta actgtctggt gaccagggcg cacgagctcg   10080
gtgtatttaa ggcgcgaata ggcgcgggtg tcaaagatgt aatcgttgca ggtgcgcacc   10140
agatactggt accctataag aaaatgcggc ggtggttggc ggtagagagg ccatcgttct   10200
gtagctggag cgccaggggc gaggtcttcc aacataaggc ggtgatagcc gtagatgtac   10260
ctggacatcc aggtgattcc tgcggcggta gtagaagccc gaggaaactc gcgtacgcgg   10320
ttccaaatgt tgcgtagcgg catgaagtag ttcattgtag gcacggtttg accagtgagg   10380
cgcgcgcagt cattgatgct ctatagacac ggagaaaatg aaagcgttca gcgactcgac   10440
tccgtagcct ggaggaacgt gaacggggttg ggtcgcggtg taccccggtt cgagacttgt   10500
actcgagccg gccggagccg cggctaacgt ggtattggca ctcccgtctc gacccagcct   10560
acaaaaatcc aggatacgga atcgagtcgt tttgctggtt tccgaatggc agggaagtga   10620
gtcctatttt tttttttgc cgctcagatg catcccgtgc tgcgacagat gcgcccccaa   10680
caacagcccc cctcgcagca gcagcagcag caatcacaaa aggctgtccc tgcaactact   10740
gcaactgccg ccgtgagcgg tgcgggacag cccgcctatg atctggactt ggaagagggc   10800
gaaggactgg cacgtctagg tgcgccttca cccgagcggc atccgcgagt tcaactgaaa   10860
aaagattctc gcgaggcgta tgtgccccaa cagaacctat ttagagacag aagcggcgag   10920
gagccggagg agatgcgagc ttcccgcttt aacgcgggtc gtgagctgcg tcacggtttg   10980
gaccgaagac gagtgttgcg ggacgaggat ttcgaagttg atgaaatgac agggatcagt   11040
cctgccaggg cacacgtggc tgcagccaac cttgtatcgg cttacgagca gacagtaaag   11100
gaagagcgta acttccaaaa gtcttttaat aatcatgtgc gaaccctgat tgcccgcgaa   11160
gaagttaccc ttggtttgat gcatttgtgg gatttgatgg aagctatcat tcagaaccct   11220
actagcaaac ctctgaccgc ccagctgttt ctggtggtgc aacacagcag agacaatgag   11280
gctttcagag aggcgctgct gaacatcacc gaacccgagg ggagatggtt gtatgatctt   11340
atcaacattc tacagagtat catagtgcag gagcggagcc tgggcctggc cgagaaggtg   11400
gctgccatca attactcggt tttgagcttg ggaaaatatt acgctcgcaa aatctacaag   11460
actccatacg ttcccatagacaaggaggtg aagatagatg ggttctacat gcgcatgacg   11520
ctcaaggtct tgaccctgag cgatgatctt ggggtgtatc gcaatgacag aatgcatcgc   11580
gcggttagcg ccagcaggag gcgcgagtta agcgacaggg aactgatgca cagttttgcaa   11640
agagctctga ctggagctgg aaccgagggt gagaattact tcgacatggg agctgacttg   11700
cagtggcagc ctagtcgcag ggctctgagc gccgcgacgg caggatgtga gcttccttac   11760
atagaagagg cggatgaagg cgaggaggaa gagggcgagt acttggaaga ctgatggcac   11820
aacccgtgtt ttttgctaga tggaacagca agcaccggat cccgcaatgc gggcggcgct   11880
gcagagccag ccgtccggca ttaactcctc ggacgattgg acccaggcca tgcaacgtat   11940
catggcgttg acgactcgca accccgaagc ctttagacag caaccccagg ccaaccgtct   12000
```

```
atcggccatc atggaagctg tagtgccttc ccgctctaat cccactcatg agaaggtcct   12060
ggccatcgtg aacgcgttgg tggagaacaa agctattcgt ccagatgagg ccggactggt   12120
atacaacgct ctcttagaac gcgtggctcg ctacaacagt agcaatgtgc aaaccaattt   12180
ggaccgtatg ataacagatg tacgcgaagc cgtgtctcag cgcgaaaggt ccagcgtga    12240 tgccaacctg ggttcgctgg tggcgttaaa tgctttcttg agtactcagc ctgctaatgt   12300
gccgcgtggt caacaggatt atactaactt tttaagtgct ttgagactga tggtatcaga   12360
agtacctcag agcgaagtgt atcagtccgg tcctgattac ttctttcaga ctagcagaca   12420
gggcttgcag acggtaaatc tgagccagc ttttaaaaac cttaaaggtt tgtggggagt    12480
gcatgccccg gtaggagaaa gagcaaccgt gtctagcttg ttaactccga actcccgcct   12540
attattactg ttggtagctc ctttcaccga cagcggtagc atcgaccgta attcctattt   12600
gggttaccta ctaaacctgt atcgcgaagc catagggcaa agtcaggtgg acgagcagac   12660
ctatcaagaa attacccaag tcagtcgcgc tttgggacag gaagacactg gcagtttgga   12720
agccactctg aacttcttgc ttaccaatcg gtctcaaaag atccctcctc aatatgctct   12780
tactgcggag gaggagagga tccttagata tgtgcagcag agcgtgggat tgtttctgat   12840
gcaagagggg gcaactccga ctgcagcact ggacatgaca gcgcgaaata tggagcccag   12900
catgtatgcc agtaaccgac cttttcattaa caaactgctg gactacttgc acagagctgc   12960
cgctatgaac tctgattatt tcaccaatgc catcttaaac ccgcactggc tgccccacc    13020 tggtttctac acgggcgaat atgacatgcc cgaccctaat gacggatttc tgtgggacga   13080
cgtggacagc gatgttttt cacctctttc tgatcatcgc acgtggaaaa aggaaggcgg    13140
cgatagaatg cattcttctg catcgctgtc cggggtcatg ggtgctaccg cggctgagcc   13200
cgagtctgca agtccttttc ctagtctacc cttttctcta cacagtgtac gtagcagcga   13260
agtgggtaga ataagtcgcc cgagtttaat gggcgaagag gagtatctaa acgattcctt   13320
gctcagaccg gcaagagaaa aaaatttccc aaacaatgga atagaaagtt tggtggataa   13380
aatgagtaga tggaagactt atgctcagga tcacagagac gagcctggga tcatggggat   13440
tacaagtaga gcgagccgta gacgccagcg ccatgacaga cagaggggtc ttgtgtggga   13500
cgatgaggat tcggccgatg atagcagcgt gctggacttg ggtgggagag aaggggcaa    13560 cccgtttgct catttgcgcc ctcgcttggg tggtatgttg taaaaaaaaa taaaaaaaa    13620 actcaccaag gccatggcga cgagcgtacg ttcgttcttc tttattatct gtgtctagta   13680
taatgaggcg agtcgtgcta ggcggagcgg tggtgtatcc ggagggtcct cctccttcgt   13740
acgagagcgt gatgcagcag cagcaggcga cggcggtgat gcaatcccca ctggaggctc   13800
cctttgtgcc tccgcgatac ctggcaccta cggaggcag aaacagcatt cgttattcgg    13860
aactggcacc tcagtacgat accaccaggt tgtatctggt ggacaacaag tcggcggaca   13920
ttgcttctct gaactatcag aatgaccaca gcaacttctt gaccacgtg gtgcaaaaca    13980 atgactttac ccctacggaa gccagcaccc agaccattaa ctttgatgaa cgatcgcggt   14040
ggggcggtca gctaaagacc atcatgcata ctaacatgcc aaacgtgaac gagtatatgt   14100
ttagtaacaa gttcaaagcg cgtgtgatgg tgtccagaaa acctcccgac ggtgctgcag   14160
ttggggatac ttatgatcac aagcaggata ttttgaaata tgagtggttc gagtttactt   14220
tgccagaagg caacttttca gttactatga ctattgattt tgatgaacaat gccatcatag   14280 ataattactt gaaagtgggt agacagaatg gagtgcttga aagtgacatt ggtgttaagt   14340
```

```
tcgacaccag gaacttcaag ctgggatggg atcccgaaac caagttgatc atgcctggag   14400
tgtatacgta tgaagccttc catcctgaca ttgtcttact gcctggctgc ggagtggatt   14460
ttaccgagag tcgtttgagc aaccttcttg gtatcagaaa aaaacagcca tttcaagagg   14520
gttttaagat tttgtatgaa gatttagaag gtggtaatat tccggccctc ttggatgtag   14580
atgcctatga gaacagtaag aaagaacaaa aagccaaaat agaagctgct acagctgctg   14640
cagaagctaa ggcaaacata gttgccagcg actctacaag ggttgctaac gctggagagg   14700
tcagaggaga caattttgcg ccaacacctg ttccgactgc agaatcatta ttggccgatg   14760
tgtctgaagg aacggacgtg aaactcacta ttcaacctgt agaaaaagat agtaagaata   14820
gaagctataa tgtgttggaa gacaaaatca acacagccta tcgcagttgg tatctttcgt   14880
acaattatgg cgatcccgaa aaaggagtgc gttcctggac attgctcacc acctcagatg   14940
tcacctgcgg agcagagcag gtctactggt cgcttccaga catgatgaag gatcctgtca   15000 cttttccgctc cactagacaa gtcagtaact accctgtggt gggtgcagag cttatgcccg   15060
tcttctcaaa gagcttctac aacgaacaag ctgtgtactc ccagcagctc cgccagtcca   15120
cctcgcttac gcacgtcttc aaccgctttc ctgagaacca gatttttaatc cgtccgccgg   15180 cgcccaccat taccaccgtc agtgaaaacg ttcctgctct cacagatcac gggaccctgc   15240
cgttgcgcag cagtatccgg ggagtccaac gtgtgaccgt tactgacgcc agacgccgca   15300
cctgtcccta cgtgtacaag gcactgggca tagtcgcacc gcgcgtcctt tcaagccgca   15360 cttttctaaaa aaaaaaaaaa tgtccattct tatctcgccc agtaataaca ccggttgggg   15420
tctgcgcgct ccaagcaaga tgtacggagg cgcacgcaaa cgttctaccc aacatcctgt   15480
ccgtgttcgc ggacattttc gcgctccatg gggcgccctc aagggccgca ctcgcgttcg   15540
aaccaccgtc gatgatgtaa tcgatcaggt ggttgccgac gcccgtaatt atactcctac   15600
tgcgcctaca tctactgtgg atgcagttat tgacagtgta gtggctgacg ctcgcaacta   15660
tgctcgacgt aagagccggc gaaggcgcat tgccagacgc caccgagcta ccactgccat   15720
gcgagccgca agagctctgc tacgaagagc tagacgcgtg gggcgaagag ccatgcttag   15780
ggcggccaga cgtgcagctt cgggcgccag cgccggcagg tcccgcaggc aagcagccgc   15840
tgtcgcagcg gcgactattg ccgacatggc ccaatcgcga agaggcaatg tatactgggt   15900
gcgtgacgct gccaccggtc aacgtgtacc cgtgcgcacc cgtccccctc gcacttagaa   15960
gatactgagc agtctccgat gttgtgtccc agcggcgagg atgtccaagc gcaaatacaa   16020
ggaagaaatg ctgcaggtta tcgcacctga agtctacggc caaccgttga aggatgaaaa   16080
aaaaccccgc aaaatcaagc gggttaaaaa ggacaaaaaa gaagaggaag atggcgatga   16140
tgggctggcg gagtttgtgc gcgagtttgc cccacggcga cgcgtgcaat ggcgtgggcg   16200
caaagttcga catgtgttga gacctggaac ttcggtggtc tttacacccg gcgagcgttc   16260
aagcgctact tttaagcgtt cctatgatga ggtgtacggg gatgatgata ttcttgagca   16320
ggcggctgac cgattaggcg agtttgctta tgcaagcgt agtagaataa cttccaagga   16380
tgagacagtg tcgatacccct tggatcatgg aaatcccacc cctagtctta aaccggtcac   16440
tttgcagcaa gtgttacccg taactccgcg aacaggtgtt aaacgcgaag gtgaagatttt   16500 gtatcccact atgcaactga tggtacccaa acgccagaag ttggaggacg ttttggagaa   16560
agtaaaagtg gatccagata ttcaacctga ggttaaagtg agaccattaa gcaggtagc   16620 gcctggtctg ggggtacaaa ctgtagacat taagattccc actgaaagta tggaagtgca   16680
aactgaaccc gcaaagccta ctgccacctc cactgaagtg caaacggatc catggatgcc   16740
```

```
catgcctatt acaactgacg ccgccggtcc cactcgaaga tcccgacgaa agtacggtcc    16800
agcaagtctg ttgatgccca attatgttgt acacccatct attattccta ctcctggtta    16860
ccgaggcact cgctactatc gcagccgaaa cagtacctcc cgccgtcgcc gcaagacacc    16920
tgcaaatcgc agtcgtcgcc gtagacgcac aagcaaaccg actcccggcg ccctggtgcg    16980
gcaagtgtac cgcaatggta gtgcggaacc tttgacactg ccgcgtgcgc gttaccatcc    17040
gagtatcatc acttaatcaa tgttgccgct gcctccttgc agatatggcc ctcacttgtc    17100
gccttcgcgt tcccatcact ggttaccgag gaagaaactc gcgccgtaga gagggatgt     17160 tgggacgcgg aatgcgacgc tacaggcgac ggcgtgctat ccgcaagcaa ttgcggggtg    17220
gttttttacc agccttaatt ccaattatcg ctgctgcaat tggcgcgata ccaggcatag    17280
cttccgtggc ggttcaggcc tcgcaacgac attgacattg gaaaaaaacg tataaataaa    17340 aaaaaaaaa tacaatggac tctgacactc ctggtcctgt gactatgttt tcttagagat    17400 ggaagcatc aatttttcat ccttggctcc gcgacacggc acgaagccgt acatgggcac    17460
ctggagcgac atcggcacga gccaactgaa cgggggcgcc ttcaattgga gcagtatctg    17520
gagcgggctt aaaaattttg gctcaaccat aaaaacatac gggaacaaag cttggaacag    17580
cagtacagga caggcgctta gaaataaact taaagaccag aacttccaac aaaaagtagt    17640
cgatgggata gcttccggca tcaatggagt ggtagatttg gctaaccagg ctgtgcagaa    17700
aaagataaac agtcgtttgg acccgccgcc agcaacccca ggtgaaatgc aagtggagga    17760
agaaattcct ccgccagaaa acgaggcga caagcgtccg cgtccgatt tggaagagac      17820 gctggtgacg cgcgtagatg aaccgccttc ttatgaggaa gcaacgaagc ttggaatgcc    17880
caccactaga ccgatagccc caatggccac cggggtgatg aaaccttctc agttgcatcg    17940
acccgtcacc ttggatttgc cccctccccc tgctgctact gctgtacccg cttctaagcc    18000
tgtcgctgcc ccgaaaccag tcgccgtagc caggtcacgt cccggggggcg ctcctcgtcc   18060 aaatgcgcac tggcaaaata tctctgaacag catcgtgggt ctaggcgtgc aaagtgtaaa   18120
acgccgtcgc tgcttttaat taaatatgga gtagcgctta acttgcctat ctgtgtatat    18180
gtgtcattac acgccgtcac agcagcagag gaaaaaagga agaggtcgtg cgtcgacgct    18240
gagttacttt caagatggcc accccatcga tgctgcccca atgggcatac atgcacatcg    18300
ccggacagga tgcttcggag tacctgagtc cgggtctggt gcagttcgcc cgcgccacag    18360
acacctactt caatctggga aataagttta gaaatcccac cgtagcgccg acccacgatg    18420
tgaccaccga ccgtagccag cggctcatgt tgcgcttcgt gcccgttgac cgggaggaca    18480
atacatactc ttacaaagtg cggtacaccc tggccgtggg cgacaacaga gtgctggata    18540
tggccagcac gttctttgac attagggggtg tgttggacag aggtcccagt ttcaaaccct    18600
attctggtac ggcttacaac tccctggctc ctaaaggcgc tccaaataca tctcagtgga    18660
ttgcagaagg tgtaaaaaat acaactggtg aggaacacg aacagaagag gaaaccaata    18720
ctactactta cactttggc aatgctcctg taaaagctga agctgaaatt acaaaagaag     18780
gactcccagt aggtttggaa gtttcagatg aagaaagtaa accgattat gctgataaaa     18840 catatcagcc agaacctcag ctgggagatg aaacttggac tgaccttgat ggaaaaaccg    18900
aaaagtatgg aggcagggct ctcaaacccg atactaagat gaaaccatgc tacgggtcct    18960
ttgccaaacc tactaatgtg aaaggcggtc aggcaaaaca aaaacaacg gagcagccaa     19020 atcagaaagt cgaatatgat atcgacatgg agttttttga tgcggcatcg cagaaaacaa    19080
```

```
acttaagtcc taaaattgtc atgtatgcag aaaatgtaaa tttggaaact ccagacactc   19140
atgtagtgta caaacctgga acagaagaca caagttccga agctaatttg ggacaacaat   19200
ctatgcccaa cagacccaac tacattggct tcagagataa ctttattgga cttatgtact   19260
ataacagtac tggtaacatg ggggtgctgg ctggtcaagc gtctcagtta aatgcagtgg   19320
ttgacttgca ggacagaaac acagaacttt cttaccaact cttgcttgac tctctgggcg   19380
acagaaccag atactttagc atgtggaatc aggctgtgga cagttatgat cctgatgtac   19440
gtgttattga aaatcatggt gtggaagatg aacttcccaa ctactgtttt ccactggacg   19500
gcataggtgt tccaacaacc agttacaaat caatagttcc aaatggagac aatgcgccta   19560
attggaagga acctgaagta aatggaacaa gtgagatcgg acagggtaat ttgtttgcca   19620
tggaaattaa ccttcaagcc aatctatggc gaagtttcct ttattccaat gtggctctat   19680
atctcccaga ctcgtacaaa tacaccccgt ccaatgtcac tcttccagaa aacaaaaaca   19740
cctacgacta catgaacggg cgggtggtgc cgccatctct agtagacacc tatgtgaaca   19800
ttggtgccag gtggtctctg gatgccatgg acaatgtcaa cccattcaac caccaccgta   19860
acgctggctt gcgttaccga tccatgcttc tgggtaacgg acgttatgtg cctttccaca   19920
tacaagtgcc tcaaaaattc ttcgctgtta aaaacctgct gcttctccca ggctcctaca   19980
cttatgagtg aactttagg aaggatgtga acatggttct acagagttcc ctcggtaacg   20040
acctgcgggt agatggcgcc agcatcagtt tcacgagcat caacctctat gctacttttt   20100
tccccatggc tcacaacacc gcttccaccc ttgaagccat gctgcggaat gacaccaatg   20160
atcagtcatt caacgactac ctatctgcag ctaacatgct ctaccccatt cctgccaatg   20220
caaccaatat tcccatttcc attccttctc gcaactgggc ggctttcaga ggctggtcat   20280
ttaccagact gaaaaccaaa gaaactccct ctttggggtc tggatttgac ccctactttg   20340
tctattctgg ttctattccc tacctggatg gtaccttcta cctgaaccac acttttaaga   20400
aggtttccat catgtttgac tcttcagtga gctggcctgg aaatgacagg ttactatctc   20460
ctaacgaatt tgaaataaag cgcactgtgg atggcgaagg ctacaacgta gcccaatgca   20520
acatgaccaa agactggttc ttggtacaga tgctcgccaa ctacaacatc ggctatcagg   20580
gcttctacat tccagaagga tacaaagatc gcatgtattc atttttcaga aacttccagc   20640
ccatgagcag gcaggtggtt gatgaggtca attacaaaga cttcaaggcc gtcgccatac   20700
cctaccaaca caacaactct ggctttgtgg gttacatggc tccgaccatg cgccaaggtc   20760
aaccctatcc cgctaactat ccctatccac tcattggaac aactgccgta aatagtgtta   20820
cgcagaaaaa gttcttgtgt gacagaacca tgtggcgcat accgttctcg agcaacttca   20880
tgtctatggg ggcccttaca gacttgggac agaatatgct ctatgccaac tcagctcatg   20940
ctctggacat gaccttgag gtggatccca tggatgagcc caccctgctt tatcttctct   21000
tcgaagtttt cgacgtggtc agagtgcatc agccacaccg cggcatcatc gaggcagtct   21060
acctgcgtac accgttctcg gccggtaacg ctaccacgta agaagcttct tgcttcttgc   21120
aaatagcagc tgcaaccatg gcctgcggat cccaaaacgg ctccagcgag caagagctca   21180
gagccattgt ccaagacctg ggttgcggac cctattttt gggaacctac gataagcgct   21240
tcccggggtt catggccccc gataagctcg cctgtgccat tgtaaatacg gccggacgtg   21300
agacggggg agagcactgg ttggctttcg gttggaaccc acgttctaac acctgctacc   21360
tttttgatcc tttttgattc tcggatgatc gtctcaaaca gatttaccag tttgaatatg   21420
agggtctcct gcgccgcagc gctcttgcta ccaaggaccg ctgtattacg ctggaaaaat   21480
```

```
ctacccagac cgtgcagggt ccccgttctg ccgcctgcgg acttttctgc tgcatgttcc    21540
ttcacgcctt tgtgcactgg cctgaccgtc ccatggacgg aaaccccacc atgaaattgc    21600
taactggagt gccaaacaac atgcttcatt ctcctaaagt ccagcccacc ctgtgtgaca    21660
atcaaaaagc actctaccat tttcttaata cccattcgcc ttattttcgc tcccatcgta    21720
cacacatcga aagggccact gcgttcgacc gtatggatgt tcaataatga ctcatgtaaa    21780
caacgtgttc aataaacatc actttatttt tttacatgta tcaaggctct gcattactta    21840
tttatttaca agtcgaatgg gttctgacga gaatcagaat gacccgcagg cagtgatacg    21900
ttgcggaact gatacttggg ttgccacttg aattcgggaa tcaccaactt gggaaccggt    21960
atatcgggca ggatgtcact ccacagcttt ctggtcagct gcaaagctcc aagcaggtca    22020
ggagccgaaa tcttgaaatc acaattagga ccagtgcttt gagcgcgaga gttgcggtac    22080
accggattgc agcactgaaa caccatcagc gacggatgtc tcacgcttgc cagcacggtg    22140
ggatctgcaa tcatgcccac atccagatct tcagcattgg caatgctgaa cggggtcatc    22200
ttgcaggtct gcctacccat ggcgggcacc caattaggct tgtggttgca atcgcagtgc    22260
agggggatca gtatcatctt ggcctgatcc tgtctgattc ctggatacac ggctctcatg    22320
aaagcatcat attgcttgaa agcctgctgg gctttactac cctcggtata aacatcccg    22380 caggacctgc tcgaaaactg gttagctgca cagccggcat cattcacaca gcagcgggcg    22440
tcattgttag ctatttgcac cacacttctg ccccagcggt tttgggtgat tttggttcgc    22500
tcgggattct cctttaaggc tcgttgtccg ttctcgctgg ccacatccat ctcgataatc    22560
tgctccttct gaatcataat attgccatgc aggcacttca gcttgccctc ataatcattg    22620
cagccatgag gccacaacgc acagcctgta cattcccaat tatggtgggc gatctgagaa    22680
aaagaatgta tcattccctg cagaaatctt cccatcatcg tgctcagtgt cttgtgacta    22740
gtgaaagtta actggatgcc tcggtgctcc tcgtttacgt actggtgaca gatgcgcttg    22800
tattgttcgt gttgctcagg cattagttta aaagaggttc taagttcgtt atccagcctg    22860
tacttctcca tcagcagaca catcacttcc atgcctttct cccaagcaga caccaggggc    22920
aagctaatcg gattcttaac agtgcaggca gcagctcctt tagccagagg gtcatcttta    22980
gcgatcttct caatgcttct tttgccatcc ttctcaacga tgcgcacggg cgggtagctg    23040
aaacccactg ctacaagttg cgcctcttct ctttcttctt cgctgtcttg actgatgtct    23100
tgcatgggga tatgtttggt cttccttggc ttctttttgg ggggtatcgg aggaggagga    23160
ctgtcgctcc gttccggaga cagggaggat tgtgacgttt cgctcaccat taccaactga    23220
ctgtcggtag aagaacctga ccccacacgg cgacaggtgt ttctcttcgg gggcagaggt    23280
ggaggcgatt gcgaagggct gcggtccgac ctggaaggcg gatgactggc agaacccctt    23340
ccgcgttcgg gggtgtgctc cctgtggcgg tcgcttaact gatttccttc gcggctggcc    23400
attgtgttct cctaggcaga gaaacaacag acatggaaac tcagccattg ctgtcaacat    23460
cgccacgagt gccatcacat ctcgtcctca gcgacgagga aaaggagcag agcttaagca    23520
ttccaccgcc cagtcctgcc accacctcta ccctagaaga taaggaggtc gacgcatctc    23580
atgacatgca gaataaaaaa gcgaaagagt ctgagacaga catcgagcaa gacccgggct    23640
atgtgacacc ggtggaacac gaggaagagt tgaaacgctt tctagagaga gaggatgaaa    23700
actgcccaaa acaacgagca gataactatc accaagatgc tggaaatagg gatcagaaca    23760
ccgactacct catagggctt gacggggaag acgcgctcct taaacatcta gcaagacagt    23820
```

```
cgctcatagt caaggatgca ttattggaca gaactgaagt gcccatcagt gtggaagagc    23880
tcagccgcgc ctacgagctt aacctctttt cacctcgtac tcccccaaa cgtcagccaa     23940
acggcacctg cgagccaaat cctcgcttaa acttttatcc agcttttgct gtgccagaag    24000
tactggctac ctatcacatc ttttttaaaa atcaaaaaat tccagtctcc tgccgcgcta    24060
atcgcacccg cgccgatgcc ctactcaatc tgggacctgg ttcacgctta cctgatatag    24120
cttccttgga agaggttcca aagatcttcg agggtctggg caataatgag actcgggccg    24180
caaatgctct gcaaaaggga gaaaatggca tggatgagca tcacagcgtt ctggtggaat    24240
tggaaggcga taatgccaga ctcgcagtac tcaagcgaag catcgaggtc acacacttcg    24300
catatcccgc tgtcaacctg cccctaaag tcatgacggc ggtcatggac cagttactca     24360
ttaagcgcgc aagtccccctt tcagaagaca tgcatgaccc agatgcctgt gatgagggta    24420
aaccagtggt cagtgatgag cagctaaccc gatggctggg caccgactct cccagggatt    24480
tggaagagcg tcgcaagctt atgatggccg tggtgctggt taccgtagaa ctagagtgtc    24540
tccgacgttt ctttaccgat tcagaaacct tgcgcaaact cgaagagaat ctgcactaca    24600
cttttagaca cggctttgtg cggcaggcat gcaagatatc taacgtggaa ctcaccaacc    24660
tggtttccta catgggtatt ctgcatgaga atcgcctagg acaaagcgtg ctgcacagca    24720
ccctgaaggg ggaagcccgc cgtgattaca tccgcgattg tgtctatctg tacctgtgcc    24780
acacgtggca aaccggcatg ggtgtatggc agcaatgttt agaagaacag aacttgaaag    24840
agcttgacaa gctcttacag aaatctctta aggttctgtg acagggttc gacgagcgca     24900
ccgtcgcttc cgacctggca gacctcatct cccagagcg tctcagggtt actttgcgaa     24960
acggattgcc tgactttatg agccagagca tgcttaacaa ttttcgctct ttcatcctgg    25020
aacgctccgg tatcctgccc gccacctgct gcgcactgcc ctcgactttt gtgcctctca    25080
cctaccgcga gtgcccccg ccgctatgga gtcactgcta cctgttccgt ctggccaact     25140
atctctccta ccactcggat gtgatcgagg atgtgagcgg agacggcttg ctggagtgtc    25200
actgccgctg caatctgtgc acgccccacc ggtccctagc ttgcaacccc cagttgatga    25260
gcgaaaccca gataataggc accttttgaat tgcaaggccc cagcagccaa ggcgatgggt    25320
cttctcctgg gcaaagttta aaactgaccc cgggactgtg gacctccgcc tacttgcgca    25380
agtttgctcc ggaagattac caccccctatg aaatcaagtt ctatgaggac caatcacagc    25440
ctccaaaggc cgaactttcg gcctgcgtca tcacccaggg ggcaattctg gcccaattgc    25500
aagccatcca aaaatcccgc caagaatttc tactgaaaaa gggtaagggg gtctaccttg    25560
accccccagac cggcgaggaa ctcaacacaa ggttccctca ggatgtccca acgacgagaa    25620
aacaagaagt tgaaggtgca gccgccgccc ccagaagata tggaggaaga ttgggacagt    25680
caggcagagg aggcggagga ggacagtctg gaggacagtc tggaggaaga cagtttggag    25740
gaggaaaacg aggaggcaga ggaggtggaa gaagtaaccg ccgacaaaca gttatcctcg    25800
gctgcggaga caagcaacag cgctaccatc tccgctccga gtcgaggaac ccggcggcgt    25860
cccagcagta gatgggacga gaccggacgc ttcccgaacc caaccagcgc ttccaagacc    25920
ggtaagaagt atcggcaggg atacaagtcc tggcgggggc ataagaatgc catcatctcc    25980
tgcttgcatg agtgcggggg caacatatcc ttcacgcggc gctacttgct attccaccat    26040
ggggtgaact ttccgcgcaa tgttttgcat tactaccgtc acctccacag cccctactat    26100
agccagcaaa tccggcagt ctcgacagat aaagacagcg gcggcgacct ccaacagaaa     26160
accagcagcg gcagttagaa aatacacaac aagtgcagca acaggaggat taaagattac    26220
```

```
agccaacgag ccagcgcaaa cccgagagtt aagaaatcgg atctttccaa ccctgtatgc   26280
catcttccag cagagtcggg gtcaagagca ggaactgaaa ataaaaaacc gatctctgcg   26340
ttcgctcacc agaagttgtt tgtatcacaa gagcgaagat caacttcagc gcactctcga   26400
ggacgccgag gctctcttca acaagtactg cgcgctgact cttaaagagt aggcagcgac   26460
cgcgcttatt caaaaaggc gggaattaca tcatcctcga catgagtaaa gaaattccca   26520
cgccttacat gtggagttat caaccccaaa tgggattggc ggcaggcgcc tcccaggact   26580
actccacccg catgaattgg ctcagcgccg ggccttctat gatttctcga gttaatgata   26640
tacgcgccta ccgaaaccaa atactttgg aacagtcagc tcttaccacc acgcccgcc   26700 aacaccttaa tcccagaaat tggcccgccg ccctagtgta ccaggaaagt cccgctccca   26760
ccactgtatt acttcctcga gacgcccagg ccgaagtcca aatgactaat gcaggtgcgc   26820
agttagctgg cggctccacc ctatgtcgtc acaggcctcg gcataatata aaacgcctga   26880
tgatcagagg ccgaggtatc cagctcaacg acgagtcggt gagctctccg cttggtctac   26940
gaccagacgg aatctttcag attgccggct gcgggagatc ttccttcacc cctcgtcagg   27000
ctgttctgac tttggaaagt tcgtcttcgc aaccccgctc gggcggaatc gggaccgttc   27060
aatttgtgga ggagtttact ccctctgtct acttcaaccc cttctccgga tctcctgggc   27120 attaccccgga cgagttcata ccgaacttcg acgcgattag cgagtcagtg gacggctacg   27180
attgatgtct ggtgacgcgg ctgagctatc tcggctgcga catctagacc actgccgccg   27240 cttttcgctgc tttgcccggg aactcattga gttcatctac ttcgaactcc ccaaggatca   27300
ccctcaaggt ccggcccacg gagtgcggat ttctatcgaa ggcaaaatag actctcgcct   27360
gcaacgaatt ttctcccagc ggccgtgct gatcgagcga gaccagggaa acaccacggt   27420
ttccatctac tgcatttgta atcaccccgg attgcatgaa agcctttgct gtcttatgtg   27480
tactgagttt aataaaaact gaattaagac tctcctacgg actgccgctt cttcaacccg   27540
gattttacaa ccagaagaac gaaacttttc ctgtcgtcca ggactctgtt aacttcacct   27600
ttcctactca caaactagaa gctcaacgac tacaccgctt ttccagaagc attttcccta   27660
ctaatactac tttcaaaacc ggaggtgagc tccaaggtct tcctacagaa aaccctttggg   27720 tggaagcggg ccttgtagtg ctaggaattc ttgcgggtgg gcttgtgatt attctttgct   27780
acctatacac accttgcttc actttcttag tggtgttgtg gtattggttt aaaaaatggg   27840
gcccatacta gtcttgcttg ttttactttc gcttttggaa ccgggttctg ccaattacga   27900
tccatgtcta gacttcgacc cagaaaactg cacacttact tttgcacccg acacaagccg   27960
catctgtgga gttcatcgcc tctcttacga acttggcccc caacgacaaa aatttacctg   28020
catggtggga atcaacccca tagttatcac ccagcaaagt ggagatacta agggttgcat   28080
tcactgctcc tgcgattcca tcgagtgcac ctacaccctg ctgaagaccc tatgcggcct   28140
aagagacctg ctaccaatga attaaaaaat gattaataaa aaatcactta cttgaaatca   28200
gcaataaggt ctctgttgaa attttctccc agcagcacct cacttccctc ttcccaactc   28260
tggtattcta aaccccgttc agcggcatac tttctccata ctttaaaggg gatgtcaaat   28320
tttagctcct ctcctgtacc cacaatcttc atgtctttct tcccagatga ccaagagagt   28380
ccggctcagt gactccttca accctgtcta cccctatgaa gatgaaagca cctcccaaca   28440
cccctttata aacccagggt ttatttcccc aaatggcttc acacaaagcc caaacggagt   28500
tcttacttta aaatgtttaa ccccactaac aaccacaggg ggatctctac agctaaaagt   28560
```

```
gggaggggga cttacagtgg atgacaccaa cggttttttg aaagaaaaca taagtgccac   28620
cacaccactc gttaagactg gtcactctat aggtttacca ctaggagccg gattgggaac   28680
gaatgaaaat aaactttgta tcaaattagg acaaggactt acattcaatt caaacaacat   28740
ttgcattgat gacaatatta acaccttatg gacaggagtc aaccccaccg aagccaactg   28800
tcaaatcatg aactccagtg aatctaatga ttgcaaatta attctaacac tagttaaaac   28860
tggagcacta gtcactgcat ttgtttatgt tataggagta tctaacaatt ttaatatgct   28920
aactacacac agaaatataa attttactgc agagctgttt ttcgattcta ctggtaattt   28980
actaactaga ctctcatccc tcaaaactcc acttaatcat aaatcaggac aaaacatggc   29040
tactggtgcc attactaatg ctaaaggttt catgcccagc acgactgcct atccttcaa    29100 tgataattct agagaaaaag aaaactacat ttacggaact tgttactaca cagctagtga   29160
tcgcactgct tttcccattg acatatctgt catgcttaac cgaagagcaa taaatgacga   29220
gacatcatat tgtattcgta taacttggtc ctggaacaca ggagatgccc cagaggtgca   29280
aacctctgct acaaccctag tcacctcccc atttaccttt tactacatca gagaagacga   29340
ctgacaaata aagtttaact tgtttatttg aaaatcaatt cacaaaatcc gagtagttat   29400
tttgcctccc ccttcccatt taacagaata caccaatctc tccccacgca cagcttaaa    29460 catttggata ccattagata tagacatggt tttagattcc acattccaaa cagtttcaga   29520
gcgagccaat ctggggtcag tgatagataa aaatccatcg gatagtcttt ttaaagcgct   29580
ttcacagtcc aactgctgcg gatgcgactc cggagtctgg atcacggtca tctggaagaa   29640
gaacgatggg aatcataatc cgaaaacggt atcggacgat tgtgtctcat caaacccaca   29700
agcagccgct gtctgcgtcg ctccgtgcga ctgctgttta tgggatcagg gtccacagtg   29760
tcctgaagca tgatttaat agcccttaac atcaactttc tggtgcgatg cgcgcagcaa    29820
cgcattctga tttcactcaa atctttgcag taggtacaac acattattac aatattgttt   29880
aataaaccat aattaaaagc gctccagcca aaactcatat ctgatataat cgcccctgca   29940
tgaccatcat accaaagttt aatataaatt aaatgacgtt ccctcaaaaa cacactaccc   30000
acatacatga tctctttgg catgtgcata ttaacaatct gtctgtacca tggacaacgt    30060
tggttaatca tgcaacccaa tataaccttc cggaaccaca ctgccaacac cgctccccca   30120
gccatgcatt gaagtgaacc ctgctgatta caatgacaat gaagaaccca attctctcga   30180
ccgtgaatca cttgagaatg aaaaatatct atagtggcac aacatagaca taaatgcatg   30240
catcttctca taatttttaa ctcctcagga tttagaaaca tatcccaggg aataggaagc   30300
tcttgcagaa cagtaaagct ggcagaacaa ggaagaccac gaacacaact tacactatgc   30360
atagtcatag tatcacaatc tggcaacagc gggtggtctt cagtcataga agctcgggtt   30420 tcatttcct cacaacgtgg taactgggct ctggtgtaag ggtgatgtct ggcgcatgat    30480
gtcgagcgtg cgcgcaacct tgtcataatg gagttgcttc ctgacattct cgtattttgt   30540
atagcaaaac gcggccctgg cagaacacac tcttcttcgc cttctatcct gccgcttagc   30600
gtgttccgtg tgatagttca agtacaacca cactcttaag ttggtcaaaa gaatgctggc   30660
ttcagttgta atcaaaactc catcgcatct aatcgttctg aggaaatcat ccaagcaatg   30720
caactggatt gtgtttcaag caggagagga gagggaagag acggaagaac catgttaatt   30780
tttattccaa acgatctcgc agtacttcaa attgtagatc gcgcagatgg catctctcgc   30840
ccccactgtg ttggtgaaaa agcacagcta gatcaaaaga aatgcgattt tcaaggtgct   30900
caacggtggc ttccagcaaa gcctccacgc gcacatccaa gaacaaaaga ataccaaaag   30960
```

```
aaggagcatt ttctaactcc tcaatcatca tattacattc ctgcaccatt cccagataat    31020
tttcagcttt ccagccttga attattcgtg tcagttcttg tggtaaatcc aatccacaca    31080
ttacaaacag gtcccggagg gcgccctcca ccaccattct taaacacacc ctcataatga    31140
caaaatatct tgctcctgtg tcacctgtag cgaattgaga atggcaacat caattgacat    31200
gcccttggct ctaagttctt ctttaagttc tagttgtaaa aactctctca tattatcacc    31260
aaactgctta gccagaagcc ccccgggaac aagagcaggg gacgctacag tgcagtacaa    31320
gcgcagacct ccccaattgg ctccagcaaa aacaagattg gaataagcat attgggaacc    31380
gccagtaata tcatcgaagt tgctggaaat ataatcaggc agagtttctt gtaaaaattg    31440
aataaaagaa aaatttgcca aaaaaacatt caaaacctct gggatgcaaa tgcaataggt    31500
taccgcgctg cgctccaaca ttgttagttt tgaattagtc tgcaaaaata aaaaaaaaaa    31560
caagcgtcat atcatagtag cctgacgaac agatggataa atcagtcttt ccatcacaag    31620
acaagccaca gggtctccag ctcgaccctc gtaaaacctg tcatcatgat taaacaacag    31680
caccgaaagt tcctcgcggt gaccagcatg aataattctt gatgaagcat acaatccaga    31740
catgttagca tcagttaacg agaaaaaaca gccaacatag cctttgggta taattatgct    31800
taatcgtaag tatagcaaag ccaccccctcg cggatacaaa gtaaaaggca caggagaata    31860
aaaaatataa ttatttctct gctgctgttc aggcaacgtc gccccggtc cctctaaata     31920 cacatacaaa gcctcatcag ccatggctta ccagacaaag tacagcgggc acacaaagca    31980
caagctctaa agtgactctc caacctctcc acaatatata tatacacaag ccctaaactg    32040
acgtaatggg agtaaagtgt aaaaaatccc gccaaaccca acacacaccc cgaaactgcg    32100
tcaccaggga aaagtacagt ttcacttccg caatcccaac aggcgtaact tcctcttttct    32160 cacggtacgt gatatcccac taacttgcaa cgtcattttc ccacggtcgc accgcccctt    32220
ttagccgtta accccacagc caatcaccac acgatccaca cttttttaaaa tcacctcatt    32280 tacatattgg caccattcca tctataaggt atattatata gataga              32326

<210> SEQ ID NO 2
<211> LENGTH: 5287
<212> TYPE: DNA
<213> ORGANISM: Artificial Sequence
<220> FEATURE:
<223> OTHER INFORMATION: Chimeric E2B

<400> SEQUENCE: 2
ctatggcatc tcgatccagc agacctcctc gtttcgcggg tttggacggc tcctggaata     60
gggtatgaga cgatgggcgt ccagcgctgc cagggttcgg tccttccagg gtctcagtgt    120
tcgagtcagg gttgtttccg tcacagtgaa ggggtgtgcg cctgcttggg cgcttgccag    180
ggtgcgcttc agactcatcc tgctggtcga aaacttctgt cgcttggcgc cctgtatgtc    240
ggccaagtag cagtttacca tgagttcgta gttgagcgcc tcggctgcgt ggcctttggc    300
gcggagctta cctttggaag ttttcttgca taccgggcag tataggcatt tcagcgcata    360
caacttgggc gcaaggaaaa cggattctgg ggagtatgca tctgcgccgc aggaggcgca    420
aacagtttca cattccacca gccaggttaa atccggttca ttggggtcaa aaacaagttt    480
tccgccatat tttttgatgc gtttcttacc tttggtctcc atgagttcgt gtcctcgttg    540
agtgacaaac aggctgtccg tgtccccgta gactgatttt acaggcctct ctccagtgg    600 agtgcctcgg tcttcttcgt acaggaactc tgaccactct gatacaaagg cgcgcgtcca    660
```

```
ggccagcaca aaggaggcta tgtgggaggg gtagcgatcg ttgtcaacca gggggtccac      720
cttttccaaa gtatgcaaac acatgtcacc ctcttcaaca tccaggaatg tgattggctt      780
gtaggtgtat ttcacgtgac ctggggtccc cgctgggggg gtataaaagg gggcggttct      840
ttgctcttcc tcactgtctt ccggatcgct gtccaggaac gtcagctgtt ggggtaggta      900
ttccctctcg aaggcgggca tgacctctgc actcaggttg tcagtttcta agaacgagga      960
ggatttgata ttgacagtgc cggttgagat gcctttcatg aggttttcgt ccatctggtc     1020
agaaaacaca atttttttat tgtcaagttt ggtggcaaat gatccataca gggcgttgga     1080
taaaagtttg gcaatggatc gcatggtttg gttcttttcc ttgtccgcgc gctctttggc     1140
ggcgatgttg agttggacat actcgcgtgc caggcacttc cattcgggga agatagttgt     1200
taattcatct ggcacgattc tcacttgcca ccctcgatta tgcaaggtaa ttaaatccac     1260
actggtggcc acctcgcctc gaaggggttc attggtccaa cagagcctac ctccttcct      1320 agaacagaaa gggggaagtg ggtctagcat aagttcatcg ggagggtctg catccatggt     1380
aaagattccc ggaagtaaat ccttatcaaa atagctgatg ggagtggggt catctaaggc     1440
catttgccat tctcgagctg ccagtgcgcg ctcatatggg ttaaggggac tgccccatgg     1500
catgggatgg gtgagtgcag aggcatacat gccacagatg tcatagacgt agatgggatc     1560
ctcaaagatg cctatgtagg ttggatagca tcgcccccct ctgatacttg ctcgcacata     1620
gtcatatagt tcatgtgatg gcgctagcag ccccggaccc aagttggtgc gattgggttt     1680
ttctgttctg tagacgatct ggcgaaagat ggcgtgagaa ttggaagaga tggtgggtct     1740
ttgaaaaatg ttgaaatggg catgaggtag acctacagag tctctgacaa agtgggcata     1800
agattcttga agcttggtta ccagttcggc ggtgacaagt acgtctaggg cgcagtagtc     1860
aagtgtttct tgaatgatgt cataacctgg ttggttttc ttttcccaca gttcgcggtt      1920
gagaaggtat tcttcgcgat ccttccagta ctcttctagc ggaaacccgt ctttgtctgc     1980
acggtaagat cctagcatgt agaactgatt aactgccttg taagggcagc agcccttctc     2040
tacgggtaga gagtatgctt gagcagcttt tcgtagcgaa gcgtgagtaa gggcaaaggt     2100
gtctctgacc atgactttga ggaattggta tttgaagtcg atgtcgtcac aggctccctg     2160
ttcccagagt tggaagtcta cccgtttctt gtaggcgggg ttgggcaaag cgaaagtaac     2220
atcattgaag agaatcttgc cggccctggg catgaaattg cgagtgatgc gaaaaggctg     2280
tggtacttcc gctcggttat tgataacctg ggcagctagg acgatctcgt cgaaaccgtt     2340
gatgttgtgt cctacgatgt ataattctat gaaacgcggc gtgcctctga cgtgaggtag     2400
cttactgagc tcatcaaagg ttaggtctgt ggggtcagat aaggcgtagt gttcgagagc     2460
ccattcgtgc aggtgaggat tcgctttaag gaaggaggac cagaggtcca ctgccagtgc     2520
tgtttgtaac tggtcccggt actgacgaaa atgccgtccg actgccattt tttctggggt     2580
gacgcaatag aaggtttggg ggtcctgccg ccagcgatcc cacttgagtt ttatggcgag     2640
gtcataggcg atgttgacga gccgctggtc tccagagagt ttcatgacca gcatgaaggg     2700
gattagctgc ttgccaaagg accccatcca ggtgtaggtt tccacatcgt aggtgagaaa     2760
gagcctttct gtgcgaggat gagagccaat cgggaagaac tggatctcct gccaccagtt     2820
ggaggaatgg ctgttgatgt gatggaagta gaactccctg cgacgcgccg agcattcatg     2880
cttgtgcttg tacagacggc cgcagtagtc gcagcgttgc acgggttgta tctcgtgaat     2940
gagttgtacc tggcttccct tgacgagaaa tttcagtggg aagccgaggc ctggcgattg     3000
tatctcgtgc tttactatgt tgtctgcatc ggcctgttca tcttctgtct cgatggtggt     3060
```

```
catgctgacg agccctcgcg ggaggcaagt ccagacctcg gcgcggcagg ggcggagctc    3120
gaggacgaga gcgcgcaggc tggagctgtc caggtcctg agacgctgcg gactcaggtt     3180
agtaggcagt gtcaggagat taacttgcat gatcttttgg agggcgtgcg ggaggttcag    3240
atagtacttg atctcaacgg gtccgttggt ggagatgtcg atggcttgca gggttccgtg    3300
tcccttgggc gctaccaccg tgccttgtt tttcattttg dacggcggtg gctctgttgc     3360
ttcttgcatg tttagaagcg gtgtcgaggg cgcgcaccgg gcggcagggg cggctcggga    3420
cccggcggca tggctggcag tggtacgtcg gcgccgcgcg cgggtaggtt ctggtactgc    3480
gccctgagaa gactcgcatg cgcgacgacg cggcggttga catcctggat ctgacgcctc    3540
tgggtgaaag ctaccggccc cgtgagcttg aacctgaaag agagttcaac agaatcaatc    3600
tcggtatcgt tgacggcggc ttgcctaagg atttcttgca cgtcaccaga gttgtcctgg    3660
taggcgatct ccgccatgaa ctgctcgatc tcttcctctt gaagatctcc gcggcccgct    3720
ctctcgacgg tggccgcgag gtcgttggag atgcgcccaa tgagttgaga gaatgcattc    3780
atgcccgcct cgttccagac gcggctgtag accacggccc ccacgggatc tctcgcgcgc    3840
atgaccacct gggcgaggtt gagctccacg tggcgggtga agaccgcata gttgcatagg    3900
cgctggaaaa ggtagttgag tgtggtggcg atgtgctcgg tgacgaagaa atacatgatc    3960
catcgtctca gcggcatctc gctgacatcg cccagagctt ccaagcgctc catggcctcg    4020
tagaagtcca cggcaaaatt aaaaaactgg gagtttcgcg cggacacggt caactcctct    4080
tccagaagac ggataagttc ggcgatgtg gtgcgcacct cgcgctcgaa agcccctggg     4140
atttcttcct caatctcttc ttcttccact aacatctctt cctcttcagg tggggctgca    4200
ggaggagggg gaacgcggcg acgccggcgg cgcacgggca gacggtcgat gaatctttca    4260
atgacctctc cgcggcggcg gcgcatggtt tcagtgacgg cgcggccgtt ctcgcgcggt    4320
cgcagagtaa aaacaccgcc gcgcatctcc ttaaagtggt gactgggagg ttctccgttt    4380
gggagggaga gggcgctgat tatacatttt attaattggc ccgtagggac tgcacgcaga    4440
gatctgatcg tgtcaagatc cacgggatct gaaaaccttt cgacgaaagc gtctaaccag    4500
tcacagtcac aaggtaggct gagtacggct tcttgtgggc gggggtggtt atgtgttcgg    4560
tctgggtctt ctgtttcttc ttcatctcgg gaaggtgaga cgatgctgct ggtgatgaaa    4620
ttaaagtagg cagttctaag acggcggatg gtggcgagga gcaccaggtc tttgggtccg    4680
gcttgctgga tacgcaggcg attggccatt ccccaagcat tatcctgaca tctagcaaga    4740
tctttgtagt agtcttgcat gagccgttct acgggcactt cttcctcacc cgttctgcca    4800
tgcatacgtg tgagtccaaa tccgcgcatt ggttgtacca gtgccaagtc agctacgact    4860 cttcggcga ggatggcttg ctgtacttgg gtaagggtgg cttgaaagtc atcaaaatcc      4920
acaaagcggt ggtaagctcc tgtattaatg gtgtaagcac agttggccat gactgaccag    4980
ttaactgtct ggtgaccagg gcgcacgagc tcggtgtatt taaggcgcga ataggcgcgg    5040
gtgtcaaaga tgtaatcgtt gcaggtgcgc accagatact ggtacccta aagaaaatgc     5100 ggcggtggtt ggcggtagag aggccatcgt tctgtagctg gagcgccagg ggcgaggtct    5160
tccaacataa ggcggtgata gccgtagatg tacctgaca tccaggtgat tcctgcggcg     5220
gtagtagaag cccgaggaaa ctcgcgtacg cggttccaaa tgttgcgtag cggcatgaag    5280
tagttca                                                              5287
```

DOSING REGIME AND FORMULATIONS FOR TYPE B ADENOVIRUS

CROSS REFERENCE TO RELATED APPLICATIONS

This application is a US national phase of International Application No. PCT/EP2014/062284 filed on Jun. 12, 2014, which claims priority to Great Britain Patent Application No. 1310698.4 filed on Jun. 14, 2013; Great Britain Patent Application No. 1405140.3 filed on Mar. 22, 2014; and Great Britain Patent Application No. 1406509.8 filed on Apr. 10, 2014. The entire disclosure contents of each of these applications are hereby incorporated by reference into the present application.

The present disclosure relates to a method of treating a patient, for example with a replication capable oncolytic adenovirus employing a dosing regimen designed to allow the virus to have a suitable therapeutic effect and/or minimise adverse events in vivo. The disclosure also extends to formulations described herein, methods of preparing said formulations and use of the same in treatment, in particular the treatment of cancer.

BACKGROUND

Cancer is a leading cause of death and serious illness worldwide. There are over 200 different types of cancer and the type of treatment is dependent on the type of cancer. Typically, treatment will involve surgery, chemotherapy and/or radiotherapy. These treatments are often unsuccessful or are only partially successful and have significant side effects. Five year survival rates for cancer can range from less than 5% to over 95% depending on the type of cancer (CRUK statistics, 2000-2001). For example, between 2005-2009, patients with colorectal cancer, which accounts for 13% of all cancers in men and women in the UK, had a five year survival rate of approximately 55% in the UK. This drops to just 12% for patients with metastatic colorectal cancer.

The management of metastatic cancer is mainly palliative and involves a combination of palliative surgery, chemotherapy, radiation and supportive care. Clinical outcomes such as overall survival, response and toxicity are important, but alternative outcomes such as progression-free survival, quality of life, convenience, acceptability and patient choice are also important. New therapies are clearly needed to improve these outcomes.

During transformation, cancer cells acquire certain mutations which render them more permissive to virus infection. Cancer cells also induce the suppression of host anti-tumour activity. Changes within the tumour cells and the local micro-environment create a potential vulnerability and expose the tumour to infection by viruses (Liu et al 2007; Liu et al 2008;
Roberts, 2006).

There is a long history of using viruses to treat cancer beginning with anecdotal reports of temporary cancer remission after natural viral infections or viral vaccinations. The earliest report seems to be a 1912 account of the regression of cervical cancer in a patient vaccinated for rabies. Similar results were seen in cancer patients receiving smallpox vaccinations, or following natural virus infections such as mumps or measles. Based on these reports as well as animal data, inoculations of live viruses into patients for cancer treatment were initiated in the late 1940s and early 1950s.

The usual experience, however, was that after occasional temporary tumour regression, the tumour regrew and the patient died. These inoculations seldom resulted in long-lasting complete remissions. In 1957, Albert B. Sabin, M. D., who developed the live oral polio vaccine commented, "The most disappointing aspect is the fact that even when a virus is oncolytic and it punches a hole in a tumour, the immune response of the individual to the virus occurs so fast that the effects are quickly wiped out and the tumour continues to grow."

At the present time, a number of oncolytic viruses have been identified but the only virus that has been approved for clinical use anywhere in the world to date is Oncorine (H101) a subgroup C adenovirus modified by E1B-55KD deletion enabling conditional replication in P53-deficient cancer cells (H101 is a close analogue of ONYX015 as described by Bischoff et al 1996). Oncorine is administered by intratumoural injection for head and neck cancer.

Talimogene laherparepvec (Tvec), is an oncolytic virus based on Herpes simplex virus type-1 carrying ICP34.5 & ICP47 deletions, expressing US11 as an immediate early gene and encoding GM-CSF. The OPTiM trial is a multi-national, open label, randomized study designed to assess the efficacy and safety of treatment with talimogene laherparepvec as an intratumoural treatment compared to subcutaneously administered GM-CSF in patients with unresectable stage Ill (b-c) and Stage IV (M1a-c) disease. On interim analysis, talimogene laherparepvec elicited a durable response rate in 16% of patients compared to 2% in those receiving GM-CSF. Other oncolytic viruses for intra-tumoural administration currently in development include (Sheridan 2013):
   Reolysin, an oncolytic reovirus serotype 3 (Dearing strain)
   PV701, an oncolytic Newcastle disease virus
   CG0070, a conditionally replicating adenovirus encoding GM-CSF
   Pexastimogene devacirepvec (Pexa-Vec, JX-594), a thymidine kinase-deleted vaccinia virus encoding GM-CSF
   Cavatak, an unmodified Coxsackievirus A21
   Seprehvir (HSV1716), a conditionally replicating Herpes simplex type 1 carrying an ICP34.5 deletion
   DNX-2401, a conditionally replicating adenovirus encoding an integrin-binding peptide
   CGTG-102, a conditionally replicating adenovirus encoding GM-CSF
   ColoAd1 is a chimeric (Ad11/Ad3) serogroup B adenovirus, which was developed using the process of directed evolution and it is thought to be suitable for the treatment of cancers of epithelial origin and metastatic forms thereof, including colorectal cancer (Kuhn, I et al. 2008). To date, clinical studies of oncolytic viruses have primarily investigated intra-tumoural injection of the virus. In a review of clinical studies by Aghi & Martuza (2005) 25 of 36 studies used intra-tumoural injection to administer the virus. However, this method is only practical for treating easily accessible tumours and in patients where the structure of the tumour, such as tissue stroma and necrotic areas therein, do not limit spread of the virus within a tumour (Ries & Korn 2002).

Death from cancer is often the result of inaccessible tumours or metastases. Oncolytic viruses administered intra-tumourally rely on systemic dissemination from the tumour to reach these secondary tumours. However, dissemination has proved transient and often ineffective (Ferguson et al 2012).

Thus, intra-tumoural injection is only suitable for a limited number of cancers and is not suitable for treatment of, for example of many metastatic cancers.

Where intravenous administration of oncolytic viruses has been employed generally it has been associated with acute toxicity and rapid clearance. For example, in the case of the group C adenovirus Ad5, for which uptake is mediated by the ubiquitous coxsackie adenovirus receptor (CAR), side effects including acute liver toxicity, influenza like illness and haematological changes have been regularly reported, whilst rapid hepatic clearance and immunological neutralisation are also well described.

The currently established view is that repeated doses are required in order to produce and maintain efficacy. In all the oncolytic cancer treatments under investigation it is generally envisaged that the treatment will be chronic, with repeat administrations over many weeks, months or years. For example, in the case of PV701, treatment in at least one patient continued in cycles for about 10 month with 6 days between finishing the previous treatment cycle and initiating the next treatment cycle.

Neumanatis et al (2001) report administration of up to 24 weekly cycles of an intravenous infusion of ONYX-015 to cancer patients. In an on-going phase III clinical study (Clinicaltrials.gov identifier NCT01708993), Reolysin® (an oncloytic reovirus) was infused over a 1 hour period on days 1 to 3 and then every 3 weeks until progression. In a recently reported phase I clinical trial (Clinicaltrials.gov identifier NCT01380600) JX-594 was administered intravenously every 2 weeks on four occasions, and in a second on-going phase I/II clinical study (Clinicaltrials.gov identifier NCT01394939) JX-594 is administered intravenously weekly for 5 weeks followed by up to 3 intra-tumoural boosts to liver metastases of patients with metastatic colorectal cancer. In the on-going OPTIM clinical trial talimogene laherparepvec was administered intra-tumourally every two weeks for up to 18 months (Clinicaltrials.gov identifier NCT00769704).

SUMMARY OF THE INVENTION

In a first aspect of the disclosure there is provided a method of treating a human patient, said method comprising the steps of:
  systemically administering multiple doses of a parenteral formulation of a replication capable oncolytic adenovirus of subgroup B in a single treatment cycle,
  wherein the total dose given in each administration is in the range of $1\times10^{10}$ to $1\times10^{14}$ viral particles per dose, and
  wherein each dose of virus is administered such that the rate of viral particle delivery is in the range of $2\times10^{10}$ particles per minute to $2\times10^{12}$ particles per minute.

In an independent aspect the present disclosure relates to ColoAd1 for use in treating ovarian cancer, for example administering a therapeutically effective amount of ColoAd1 to a patient with ovarian cancer, for example employing a dosing regimen described herein.

In a further independent aspect the present disclosure relates to a combination therapy comprising oncolytic type B adenovirus, such as ColoAd1, and a chemotherapeutic agent which does not interfere with the adenovirus activity, such as viral replication in vivo.

In one embodiment the combination therapy is employed for treatment of cancer, in particular a cancer described herein, in particular colorectal cancer or ovarian cancer, including metastatic forms thereof.

In one embodiment ColoAd1 in a combination therapy is dosed according to a regimen described herein.

Also provided is a parenteral formulation of a replication capable oncolytic adenovirus of subgroup B, for use in treatment as described herein.

The present disclosure also extends to use of a parenteral formulation of a replication capable oncolytic adenovirus of subgroup B, for the manufacture of a medicament, as described herein and for use in treatments described herein.

In one aspect there is also provided a unit dose in the range $1\times10^{10}$ to $1\times10^{14}$, such as $6\times10^{12}$ viral particles of a replication capable oncolytic adenovirus of subgroup B.

Also provided is an infusion or injection rate for dosing the viral particles of $2\times10^9$ to $2\times10^{12}$ virus particles (VP) per minute, for example $1.5\times10^{11}$ VP per minute.

BRIEF DESCRIPTION OF THE DRAWINGS

FIG. 6 Cytokine levels after the first and subsequent equal therapeutic doses in a pre-clinical toxicology study in CD-1 mice:

FIG. 7A-C Cytokine levels (ng/L) (TNF (A), gamma interferon (B) and IL6 (C)) over time in human cancer patients with metastatic solid epithelial tumours after intravenous doses of ColoAd1.

FIG. 8A Systemic pharmacokinetics of ColoAd1 (Genome copies per mL of blood) in human cancer patients with metastatic solid epithelial tumours.

FIG. 8B Systemic pharmacokinetics of ColoAd1 (Genome copies per mL of blood) in human cancer patients with metastatic solid epithelial tumours.

FIG. 9A Systemic pharmacokinetics of ColoAd1 (Genome copies per mL of blood) in human cancer patients administered with 1e10)($1\times10^{10}$ ColoAd1 viral particles over 5 minutes.

FIG. 9B Systemic pharmacokinetics of ColoAd1 (Genome copies per mL of blood) in human cancer patients administered with 1e11 ($1\times10^{11}$) ColoAd1 viral particles over 5 minutes.

FIG. 9C Systemic pharmacokinetics of ColoAd1 (Genome copies per mL of blood) in human cancer patients administered with 1e12 ($1\times10^{12}$) ColoAd1 viral particles over 5 minutes.

FIG. 9D Systemic pharmacokinetics of ColoAd1 (Genome copies per mL of blood) in human cancer patients administered with 1e13 ($1\times10^{13}$) ColoAd1 viral particles over 5 minutes.

FIG. 9E Systemic pharmacokinetics of ColoAd1 (Genome copies per mL of blood) in human cancer patients administered with 3e12 ($3\times10^{12}$) ColoAd1 viral particles over 5 minutes.

FIG. 9F Systemic pharmacokinetics of ColoAd1 (Genome copies per mL of blood) in human cancer patients administered with 3e12 ($3\times10^{12}$) ColoAd1 viral particles over 20 minutes.

FIG. 9G Systemic pharmacokinetics of ColoAd1 (Genome copies per mL of blood) in human cancer patients administered with 6e12 ($6\times10^{12}$) ColoAd1 viral particles over 40 minutes.

FIG. 10 Slower infusion of the same dose lowers the cMax level at the end of infusion (cohort 5 vs 6)

FIG. 11 MCP1 levels (ng/L) over time in human cancer patients with metastatic solid epithelial tumours after intravenous doses of ColoAd1.

FIG. 12 Schematic diagram showing ColoAd1 replication cycle in cell.

FIG. 13 ColoAd1 infection of cancer cells shown as nuclear staining in a colorectal cell line following in vitro infection with the virus.

FIG. 14A Nuclear staining (hexon staining) of ColoAd1 in colorectal tissue from a patient with colorectal cancer after administration of ColoAd1 by IT.

FIG. 14B Isotype control staining for FIG. 14A.

FIG. 14C Colorectal tissue (hexon staining) showing no nuclear staining in stromal cells (following IV administration of ColoAd1 to a colorectal cancer patient.

FIG. 14D Isotype control for FIG. 14C.

FIG. 15 320 compounds (clinically approved or compounds in development) that were analysed for their impact on viral replication.

FIG. 16A-D An in vivo murine model showing the effects of Paclitaxel and ColoAd1 combination therapy (and controls).

FIG. 17-18 In vivo data for ColoAd1 and chemotherapy in a murine model.

DETAILED DESCRIPTION

Figure 1:
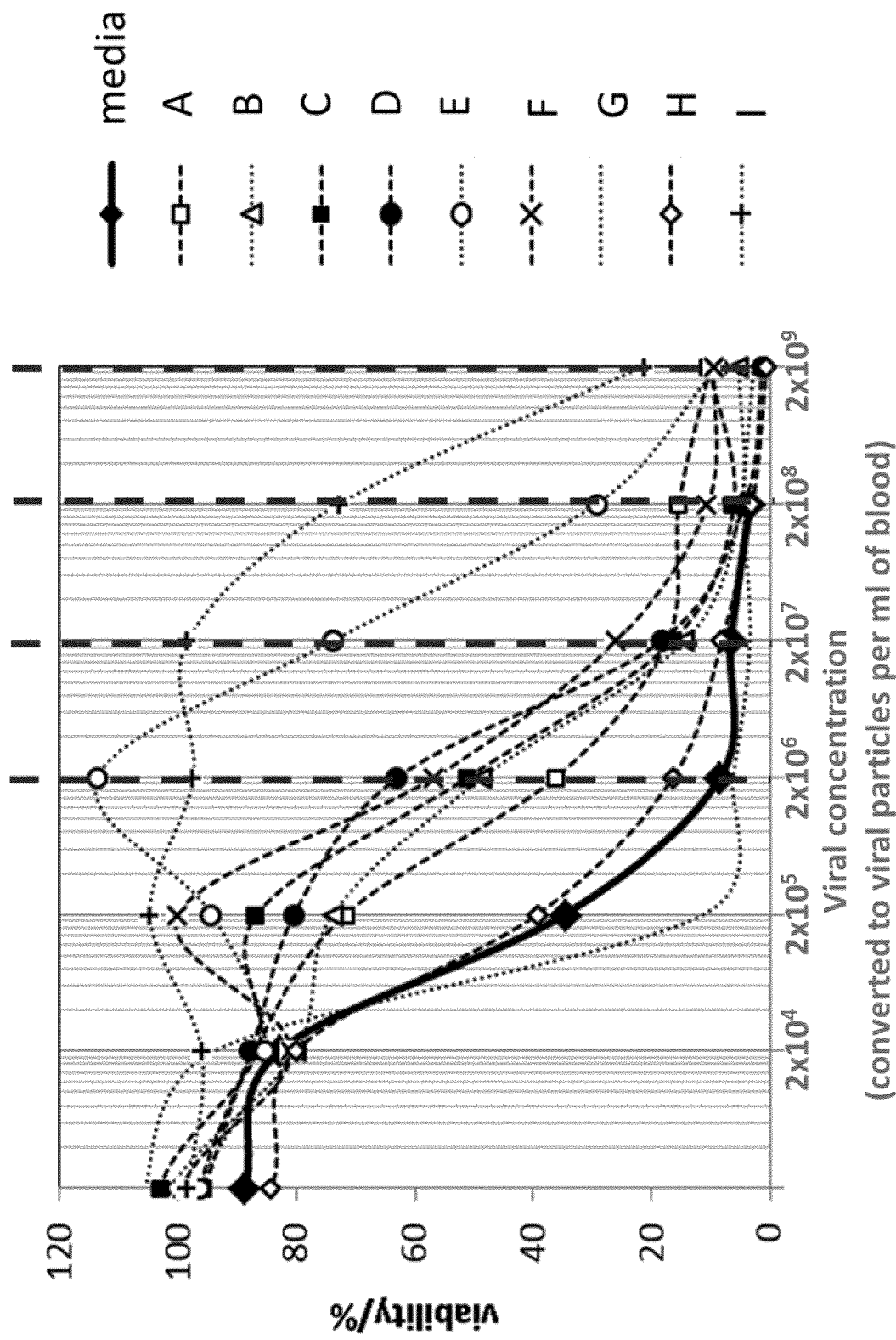
FIG. 1 Shows the cytotoxicity profile on A549 cells of ColoAd1 in the presence of fresh whole human blood.

In one embodiment the dose administered is in the range of $1\times10^{10}$ to $1\times10^{13}$, such as $1\times10^{10}$ to $1\times10^{12}$ viral particles.

In one embodiment the total dose administered in one treatment cycle is $1\times10^{12}$, $2\times10^{12}$, $3\times10^{12}$, $4\times10^{12}$, $5\times10^{12}$, $6\times10^{12}$, $7\times10^{12}$, $8\times10^{12}$ or $9\times10^{12}$ viral particles.

In one embodiment the total dose administered in one treatment cycle is $6\times10^{12}$ viral particles. It is hypothesised by the present inventors that what may be most critical for efficacy is to establish a productive infection within the tumour at an early stage, for example before an anti-viral immune response has developed.

The dosing regimen thus has to balance delivering sufficient virus to generate, for example adequate plasma levels of virus for a period long enough to seed viral infection in the cancer cells, whilst not eliciting toxicity and severe adverse events in the patient (or minimising the same).

The present inventors have shown for the first time that infection of the tumour by type B adenovirus can be established by doses of viral particles administered intravenously. Support for this conclusion is provided herein where patients with colorectal cancer that received treatment with ColoAd1 intravenously were shown to have virus infection in the nucleus of cancer cells, when the cells were stained for hexon and also when analysed independently by PCR. Virus in the nucleus indicates the virus life cycle of the virus is in progress and an increase in the viral load in the patients indicates the virus is able to replicate.

When administering an oncolytic adenovirus systemically to a patient, a number of dosing variables need to be considered. These dosing variables include, but are not limited to: the route of virus administration; the dose of virus administered; the rate of viral administration for each dose; the interval between individual viral administrations in a given cycle; the number of viral administrations per treatment cycle; the interval between treatment cycles; the number of treatment cycles; and finally the use of any co-medicaments or other supportive care used to enhance efficacy or minimise adverse effects. Each of the dosing parameters is in turn dependent upon the specific characteristics of the type of oncolytic virus under investigation.

The key parameters will include, but are not limited to: the relative degree and avidity of any binding of the virus to tumour cells versus non-tumour cells; the relative selectivity and potency of the virus in tumour cells versus non-tumour cells; the rate of active uptake and clearance of the virus by reticuloendothelial cells (for example liver Kupffer cells) and any specific or non-specific binding of blood elements to the virus.

These key parameters are in turn driven by important physical and phenotypic characteristics of the specific virus type, which include but are not limited to: the receptor specificity of the virus; the charge carried on the viral coat; the presence or absence of an envelope; the size of the viral particle; the immunogenicity of the viral particle; the inflammatory potential of the viral particle; the tumour specificity of the virus; the replicative speed of the virus; and the killing potency of the virus.

Therefore, the suitability of any given dosing regime will vary with different types of virus and the most appropriate regime may be specific to the type of virus being administered. For example, Zhang et al (2012) describe an Ad5-Ad48 chimeric virus created to reduce hexon binding with blood coagulation factor X in order to eliminate liver sequestration, enhance circulation and decrease toxicity, whilst maintaining anti-tumour activity. Likewise, Shashkova et al (2009) describe significant differences between wild-type human adenoviral serotypes 5, 6, 11, and 35 when investigated as potential anticancer agents. It is thus anticipated that different viral types will behave with significant differences when administered systemically to humans and thus the optimum dosing strategy cannot be predicted a priori without in vivo data and preferably supporting clinical data.

The dose regimen described herein may be particularly suitable to achieve this for group B adenoviruses when compared to, for example the current practice of more regularly spaced and long term repeated dosing.

The objective of an optimised dose regimen for any given oncolytic adenovirus is thus to maximise delivery of the virus to the tumour cells whilst minimising both the induction of side effects (adverse events) and antiviral immunity, in order to produce a suitable risk benefit treatment profile whilst still allowing for repeat viral administrations, as appropriate to the therapy. The optimised dose regimen will thus differ between virus types and specifically between adenoviral subtypes due to the differences in the viral coat.

Much work has been performed in the prior art based on Ad5, which is a subgroup C adenovirus, the infectivity for which is mediated by the Coxsackie Adenovirus Receptor. When delivered systemically, over 90% of the delivered dose is taken up by the liver. The rapid and extensive loss to the liver reduces the virus uptake by tumours and diminishes therapeutic efficacy. The vast majority of this dose is taken up by cytokine producing innate immune cells such as Kupffer cells, which are specialised macrophages resident in the liver. Ad5 also exhibits liver toxicity and causes necrosis and subsequent depletion of Kupffer cells.

Shoshkova et al 2009 showed that depletion of Kupffer cells by Ad5 increased levels of hepatocyte transduction with subsequent delivery of Ad5 vectors and also suggests that the mechanisms elucidated for Ad5 are not necessarily relevant to adenoviruses from subgroup B, for example Ad11 and Ad35. The data therein suggests that subgroup C adenoviruses interact with Kupffer cells in a similar manner, whereas subgroup B adenoviruses either are not well recognized by Kupffer cells or do not cause death of these cells. In particular, Shoshkova suggests that pre-dosing with Ad11 based viruses does not have the same beneficial effect upon Kupffer cells as Ad5. This paper concludes that whilst there may be some binding for subgroup B adenoviruses (including Ad11) the impact of this is in fact minimal.

Whilst not wishing to be bound by theory the present inventors believe that, contrary to the prior art suggestions, cytokine producing innate immune cells such as Kupffer cells may play a role in the clearance of subgroup B adenoviruses.

Furthermore, binding of blood coagulation factor X to Ad5 hexon is a mechanism of infection of hepatocytes and this mechanism may also be relevant to other adenoviruses in vivo (see for example Molecular Therapy vol. 17 no. 10, 1683-1691 Oct. 2009) but generally is not a mechanism of hepatic uptake for adenoviruses from subgroup B.

High global seroprevalence of Ad5 (high Ad5 neutralizing antibody titres in human populations) and certain other adenoviral serotypes represent a significant concern for the systemic application of high seroprevelance adeno-based therapies, because such blood-borne viruses can be neutralised by pre-existing antibodies, Vogels et al Journal of Virology, August 2003 Vol 77, No. 15 page 8263-8271.

Subgroup B adenoviruses have certain inherent advantages in this respect, in that they are associated with lower seroprevalence (Stone et al Journal of Virology 2005 Vol 79 No. 8 page 5090-5104) and have lower inflammatory potential. Initial dosing may thus be far more efficient than with Ad5, for example. However, the ability to avoid the immune system after systemic delivery may still become an issue with repeat dosing. Thus, even with the local suppression of the immune system by the cancer, avoidance of the immune system is still probably the biggest obstacle to the long term success of oncolytic virus therapy based on subgroup B adenoviruses. The data generated by the present inventors supports the position that the therapeutic effect of the oncolytic adenoviruses of subgroup B can thus be improved and/or the elimination of neutralisation of the adenovirus by the immune system can be minimised by employing an appropriate dosing regimen.

In one embodiment the dosing regimens herein may also minimise side-effects, for example flu like symptoms and inflammatory responses.

In one embodiment, the replication competent adenovirus is administered repeatedly during an early "dosing window" before a specific anti-viral immune response has been developed, and that later dosing windows may again be exploited when the specific anti-viral immune response has waned once more. That is to say several treatments in a short period of time followed by a period of time before initiating subsequent treatment cycles.

Advantageously, by administering the replication competent adenovirus in such a way, the viral blood levels are sufficient to establish a self-amplifying infection within the tumour (which is known to be an immunosuppressed environment) thereby potentially avoiding the need for chronic repeat administrations with the oncolytic virus. In order to establish a self-amplifying infection within the tumour, it is beneficial to maintain the level of virus within the patients' blood stream at a level above an effective infective concentration for as long as possible but without producing adverse events. This concept is akin to identifying a therapeutic window for the virus, i.e. a range of doses or dosing regimens where the therapeutic effect is optimised and the side effects are minimised.

This can be achieved by optimising both the dose administered and the infusion rate of the virus. In one embodiment, the rate of infusion of the virus is equal to or greater than the rate of clearance of the virus by the body.

Once an infection is established inside the tumour the virus is relatively protected from neutralising antibodies and is afforded a potentially permissive environment to replicate and to produce a therapeutic effect without dose limiting toxicities.

In addition, it is hypothesised by the inventors that peaks in virus concentration ($C_{max}$) contribute to side effects and that a flatter pharmacological profile may be desirable.

In one embodiment the $C_{max}$ is kept below a specific value, for example $3\times10^8$ DNA copies per ml. It appears that a $C_{max}$ level above the relevant threshold is more likely to induce serious adverse events or toxicity in some patients.

In one embodiment the rate of infusion has more influence than the absolute amount of virus administered.

Based on the data generated in the clinic, the present inventors also believe that virus can be delivered at a rate above the rate of clearance and up to 1.5 to $2\times10^{11}$ viral particles per minute over a prolonged period such as up to 72 hours or more (wherein the total dose of virus delivered is above $6\times10^{12}$ virus particles) without eliciting serious adverse events in the patient.

In one embodiment, the $C_{max}$ of the viral genome in the blood is maintained at a level of less than $3\times10^8$ genomes per ml of blood.

The present inventors have evaluated the initial rate of clearance of virus in a number of scenarios and believe that the estimated α-half-life is in the region of 18 minutes.

The use of prophylactic anti-inflammatories during oncolytic viral therapy is controversial. On the one hand it has been proposed that their use may minimise adverse events and thus enhance tolerability of oncolytic Newcastle Disease Virus (Lorence et al 2007). On the other hand, there have been reports that the occurrence of fever may be associated with enhanced oncolytic efficacy for adenoviruses (Yu et al 2007).

The present inventors have found that the use of prophylactic or therapeutic agents (including anti-inflammatories, steroids, antiemetics, antidiarrheals or analgesics) administered during this treatment cycle may enhance the tolerability of this regime, particularly allowing for higher or more frequent doses.

In one embodiment, steroids are administered during the treatment cycle.

The present inventors thus hypothesise that six parameters, used either individually or in concert, are important in achieving the goal of suitable delivery of an oncolytic subgroup B adenovirus:
  a) the number of virus particles administered with each dose,
  b) the rate that each virus dose is administered (the number of viral particles delivered per minute),
  c) the number of individual doses of virus in the treatment cycle,
  d) the interval between each individual dose within the treatment cycles,
  e) the use of prophylactic anti-inflammatory medicines during the treatment cycle, and
  f) the time period between treatment cycles.

These parameters can be balanced against each other i.e. an increased dose can be given at a slower infusion rate to off-set the negative effect of the increase.

If the dose is too low then the level of viral particles is not sufficient to establish an effective infection of the cancer cells. If the rate of administration is too slow then then the viral particles can readily be cleared by natural viral sinks (for example cytokine producing innate immune cells such as hepatic Kupffer cells or blood components) and an effective infection of the cancer/tumour cells is not achieved. If the viral dose is too high and/or if the rate of administration is too fast then the number of adverse events is likely to increase because of the high concentration of viral particles. The latter then induce an inflammatory cytokine response, which may increase the side-effects experienced by the patient. A moderate infusion rate can thus optimise the dose delivered.

On average the rate of clearance of type B adenoviruses such as ColoAd1 have an α-half-life of about 18 mins.

A single dose of virus may fail to establish an infection, but may adequately occupy or remove viral sinks (for example cytokine producing innate immune cells such as hepatic Kupffer cells or blood components). If viral sinks have been adequately occupied or removed, and if subsequent doses are administered soon thereafter, the viral kinetics may be altered for the later doses, with a longer circulating half-life and/or higher peak plasma levels. In this case, one or more doses administered shortly after the first dose may more effectively establish an effective infection of the cancer cells.

However, if the subsequent doses are administered too far apart (for example greater than 14 days apart) then the viral sinks may have time to replenish and the benefit of the prior dose may be lost and/or a specific anti-viral immune response may have developed. Depletion of, for example cytokine producing innate immune cells such as hepatic Kupffer cells with this form of dosing regimen may have an important secondary benefit in that Kupffer mediated cytokine release can be greatly reduced on subsequent viral doses such that these doses are better tolerated even in the face of higher viral plasma levels.

Thus the present inventors are advocating the administration of a given treatment cycle over a relatively short period of time, for example as described below.

From the work completed by the present inventors it appears that for a group B adenovirus multiple doses in a treatment cycle, with each dose administered over a relatively short period of time, with each dose administered as a moderately fast infusion, optionally in combination with prophylactic agents and with each dose separated by a relatively short period of time, is suitable for infecting cancer cells with oncolytic type B adenovirus with minimal toxicity.

Treatment cycles may be repeated as required.

The present inventors have monitored the inflammatory cytokines TNF, gamma interferon, IL-6 and MCP-1 as markers of acute toxicity and believe that by the second or subsequent doses, there is reduced toxicity and increased potential for the virus to infect the cancer cells in each case because the non-cancerous viral sinks are either removed or occupied by both the first and the second doses, provided these doses are administered at an appropriate dose level, rate and frequency.

In one embodiment three doses are employed in the treatment cycle, and in a further embodiment more than three doses are employed in the treatment cycle.

In one embodiment, a dose is administered on any or all of days 1, 3, 5, 14, and 21.

In another embodiment, a follow-up dose is administered as a maintenance or booster dose, for example, biweekly, weekly, once every two weeks, or every 3 weeks, such as every week or every 3 weeks, for a suitable period, in particular whilst the treatment is beneficial to the patient as maintenance therapy, for example whilst a patient remains in remission.

The skilled addressee will appreciate that various modifications to the treatment cycle can be made depending on the needs of the individual patient.

The present disclosure also extends to a replication capable oncolytic adenovirus of subgroup B for use in treatment of a human patient by systemically administering at least one dose, such as multiple doses of a parenteral formulation comprising the adenovirus in a single treatment cycle, wherein the total dose given in each administration is in the range $1 \times 10^{10}$ to $7 \times 10^{12}$, for example $1 \times 10^{10}$ to $5 \times 10^{12}$ viral particles, and is administered over a period of 1 minute to 90 minutes.

In a further aspect the disclosure extends to use of a replication capable oncolytic adenovirus of subgroup B for the manufacture of a medicament for use in the treatment of a human patient by systemically administering at least one dose, such as multiple doses of a parenteral formulation comprising the adenovirus in a single treatment cycle, wherein the total dose given in each dose is in the range $1 \times 10^{10}$ to $1 \times 10^{13}$ for example $1 \times 10^{10}$ to $7 \times 10^{12}$, such as $1 \times 10^{10}$ to $5 \times 10^{12}$, or $6 \times 10^{12}$ viral particles, and is administered over a period of 1 minute to 90 minutes.

In one embodiment the first dose in the treatment of a given cycle is a lower dose than the dose administered in subsequent treatments in the cycle.

It appears that contrary to Shoshkova's suggestion, based on work in mice, that pre-dosing with Ad11 based viruses does not have a beneficial priming effect upon cytokine producing innate immune cells such as Kupffer cells. In fact, optimisation of the dose and timing between administration of group B oncolytic adenovirus doses may be employed to minimize side effects and hence be beneficial.

In one embodiment the dose administered is $6 \times 10^{12}$, for example over a period of 20 to 60 minutes, such as 40 minutes.

In one embodiment a high first and second dose (i.e. which may correspond to a normal therapeutic dose) may be desirable to fully occupy cytokine producing innate immune cells, such as Kupffer cells (and/or other viral sinks) and thus optimise delivery for subsequent doses. To put it another way, the first and second dose may be equal.

In one embodiment all the doses administered contain an equal number of viral particles. This may be particularly advantageous in that it simplifies manufacture of the viral formulation, reduces the risk of dosing errors, and may in fact provide a highly effective treatment regime.

In one embodiment a follow-up cycle of treatment is provided 1 month to 6 months after completion of the previous treatment cycle, for example 2, 3, 4, 5 months thereafter in order to allow the immune response to wane.

In one embodiment a follow-up cycles may be a single dose administered weekly or bi-weekly, for a period of 1 month to 5 years, such 6, 7, 8, 9, 10, 11, 12, 18, 24, 30 or 36 months.

In one embodiment the following-up treatment cycle is initiated within about 14 days of administering the last dose in the first treatment cycle.

The follow-up cycles may also act as maintenance doses, thereby helping to maintain viral load at a level sufficient to provide a therapeutic effect.

In one embodiment there are 1, 2, 3, 4, 5 or more subsequent treatment cycles, for example 1 or 2.

In one embodiment there is only one treatment cycle with no subsequent treatment cycles.

In one embodiment there is provided a liquid parenteral formulation for infusion or injection of a replication capable oncolytic subgroup B adenovirus (such as ColoAd1) wherein the formulation provides a dose in the range of $1\times10^{10}$ to $1\times10^{14}$ viral particles per volume of dose, such as $6\times10^{12}$ viral particles per dose.

Also disclosed is a method for treating a patient by administering a parenteral formulation according to the present disclosure comprising a replication capable oncolytic subgroup B adenovirus, for example containing a dose described herein, such as $6\times10^{12}$ viral particles per dose.

Also disclosed is a method for treating a patient by administered parenteral formulation according to the present disclosure comprising a replication capable oncolytic subgroup B adenovirus said method comprising the co-administration to the patient of one or more substances or medicaments selected from the group comprising anti-inflammatory, steroid, anti-histamines, anti-pyretic medicaments and fluids for hydration.

Also disclosed is a method of determining when it is suitable to administer to a subject subsequent cycles of the parenteral formulation according to the disclosure comprising a replication capable oncolytic subgroup B adenovirus, said method comprising the steps of:
determining the pre-existing titre of the patient's specific antiviral immunity prior to a first treatment cycle,
serially determining the patient's specific antiviral immunity subsequent to the first treatment cycle, and
delaying any subsequent treatment cycles until the patient's specific antiviral immunity has reduced to a pre-specified percentage of baseline.

The term "serially determining" as used herein refers to determining a patient's antiviral immunity at multiple time points, which may be regularly or irregularly spaced apart. The multiple readings obtained may be used to generate an average titre over a particular period of time for example.

The term "pre-specified percentage of baseline" as used herein refers to a viral titre which is defined as a threshold or limit for a particular patient, taking into account factors such as a baseline measured before treatment is initiated, the patient's prognosis, ongoing cancer therapy, any adverse side effects, etc.

In one embodiment, the "pre-specified percentage of baseline" is 90% or less of the patient's baseline viral titre, such as 80% or less, 70% or less, 60% or less, 50% or less, 40% or less, 30% or less, 20% or less, or 10% or less.

In an alternative embodiment, no testing is performed prior to administering the subsequent treatment cycles.

In one embodiment there is provided use of a glass or plastic syringe with an internal volume in the range of 3 to 50 ml, said syringe containing a parenteral formulation comprising $1\times10^{10}$ to $1\times10^{14}$, for example $1\times10^{10}$ to $7\times10^{12}$ (such as $1\times10^{10}$ to $6\times10^{12}$ or $1\times10^{10}$ to $5\times10^{12}$, or $1\times10^{10}$ to $4\times10^{12}$, or $1\times10^{10}$ to $3\times10^{12}$, or $1\times10^{10}$ to $2\times10^{12}$, or $1\times10^{10}$ to $1\times10^{12}$) viral particles, of a replication capable oncolytic adenovirus of subgroup B, wherein the formulation is sterile and was filled into the syringe under aseptic conditions, for use in treatment, in particular for use in the manufacture of a medicament which is capable of injection or intravenous infusion to a human subject.

The skilled person will appreciate that the formulations may include an overage of the viral particles, for example to compensate for viral particles that may adhere to the surface of the syringe and which are not subsequently administered.

Advantageously, such a prefilled syringe would significantly enhance the usability and cost effectiveness for a manufactured oncolytic adenovirus of subgroup B, by removing the need for dose preparation in specialised pharmacies using expensive resources such as specialised equipment (including extraction hoods) and trained personnel.

The disclosure also extends to pre-filled vials of the said formulation, in particular vials each containing a single dose, in the range defined herein.

In one embodiment the virus formulation is provided in a concentrated form, for example concentrated liquid, suitable for diluting with a sterile isotonic diluent, such as saline, glucose or similar locally before administration to a patient.

Advantageously, the dosing regimen herein is suitable for delivering a therapeutically effective amount of subgroup B oncolytic virus to the cancer target. In particular the dosing regimen herein may minimise neutralisation and/or clearance of the oncolytic virus by, for example blood born agents, sinks, cytokine producing innate immune cells such as Kupffer cells and the immune system. The latter may lead to a better availability of the therapeutic dose of the oncolytic virus and, overall, an improved prognosis for the patient and/or improved survival. Advantageously the present regimen may also provide an improved quality of life for patients by minimising adverse events and/or side effects during treatment.

In one embodiment a patient who receives treatment according to the present disclosure shows an increased survival rate in comparison to a patient receiving the current standard treatment at the time of filing, for example a statistically significant increase in survival.

In one embodiment a patient who receives treatment according to the present disclosure shows a decreased tumour burden, in comparison to the standard treatment at the time of filing, for example a statistically significant decrease.

In one embodiment the a patient who receives treatment according to the present disclosure shows an increased likelihood of going into remission, in comparison to the standard treatment at the time of filing, for example a statistically significant increase.

In one embodiment the amount or extent of metastasis is reduced, for example is statistically significantly reduced in a patient who receives treatment according to the present disclosure in comparison to the standard treatment at the time of filing.

Whilst not wishing to be bound by theory, it is thought that cells of the mononuclear phagocyte system, and in particular cytokine producing innate immune cells such as Kupffer cells, may be responsible for the clearance of type B oncolytic viruses from the circulation, even though the prior art suggest otherwise.

Furthermore, the mouse studies conducted, by the present inventors, leads them to believe that after the first or second dose in a treatment regimen, cytokine producing innate immune cells such as the Kupffer cells are depleted or occupied such that they are unable to efficiently clear, for example the third dose and subsequent doses if those doses are administered in a short time frame after the second dose, or alternatively a lower toxicity may be observed or both. It is hypothesised that the cytokine markers indicate the latter, in that the levels of the cytokines are not significantly elevated after administration of the second or third dose when compared to the first dose, provided that the doses are administered within a relatively short time period. The present inventors take this to be an indication that the mechanisms for clearing the virus may be subdued after the first and second dose.

Whilst studies in mice do not always parallel what is seen in the human system, particularly with viruses, in this instance the human observations seem to correlate well with those in the murine model performed by the present inventors. The impact of the dosing regimen on cytokine responses and pharmacokinetics of ColoAd1 has also been exemplified in human subjects, by the present inventors.

As employed herein, "method of treating a patient by systemically administering" is intended to refer to a method of administering a therapeutic agent to a human to effect entry of the entity into the patient's circulatory system, in particular wherein the treatment is intended to prevent or slow the progression of, ameliorate or cure a malignancy, such as cancer or complications or symptoms associated therewith, for example direct administration to the circulatory system by intravenous administration.

In one embodiment systemic delivery affords the opportunity to treat a primary tumour, any overt, inaccessible or undiagnosed tumours and/or metastases. This is particularly advantageous because it may lead to a better overall prognosis for the patient and/or improved survival.

Thus systemic delivery as employed herein does not refer to treatment which is localised in the tumour or within a body cavity, such as the peritoneal cavity. Examples of systemic delivery include intravenous infusion and intramuscular and subcutaneous injection.

Parenteral formulation means a formulation designed not to be delivered through the GI tract nor through topical administration. Typical parenteral delivery routes include injection, implantation or infusion. In one embodiment the formulation is provided in a form for bolus delivery.

In one embodiment the parenteral formulation is in the form of an injection. Injection includes intravenous, subcutaneous, intra-tumoural or intramuscular injection. Injection as employed herein means the insertion of liquid into the body via a syringe. In one embodiment the method of the present disclosure does not involve intra-tumoural injection. An injection will generally involve the administration of 150 mL of fluid or less over a short period of time, for example 1.5 minutes or less.

In one embodiment the formulation is delivered into the peritoneal cavity.

For head and neck cancer, or brain metastases of epithelial cancers, intracranial injection may be necessary.

In one embodiment the parenteral formulation is in the form of an infusion.

Infusion as employed herein means the administration of fluids at a slower rate by drip, infusion pump, syringe driver or equivalent device. In one embodiment the infusion is administered over a period in the range of 1.5 minutes to 90 minutes, such as 3, 4, 5, 6, 7, 8, 9, 10, 15, 20, 25, 30, 35, 40, 45, 50, 55 or 60 minutes.

In one embodiment the volume of formulation administered is 100 mLs or less, in particular 50 mLs or less, for example 30 mls, 10 ml, 5 ml or less, such as 3 ml, such as administered by a syringe driver. The latter may be referred to as a slow injection.

In one embodiment the infusion is delivered at a rate in the range of 0.5 to 6 ml per minute, for example 0.75 ml per minute. In one embodiment, the infusion is delivered at a rate in the range of $2\times10^9$ to $2\times10^{12}$ virus particles (VP) per minute, for example $1.5\times10^{11}$ VP per minute.

In one embodiment the injection is administered as a slow injection, for example over a period of 1.5 to 30 or 1.5 to 40 minutes.

In one embodiment the formulation is for intravenous administration. This route is particularly effective for delivery of oncolytic virus because it allows rapid access to the majority of the organs and tissue and is particular useful for the treatment of metastases, for example established metastases especially those located in highly vascularised regions such as the liver and lungs.

In one embodiment a combination of administration methods are employed, for example IV and intra-tumourally or intraperitoneally and intra-tumourally, or IV and intraperitoneally.

Thus in one embodiment systemic administration of the present disclosure may be employed in combination with other routes of administration, such as intra-tumoural administration either concomitantly or sequentially, for example a first pre-treatment cycle may be intra-tumoural and the second treatment cycle may be systemic according to the present disclosure. Alternatively, the first treatment cycle may be according to the present disclosure and subsequent cycles or boosts may be intra-tumoural, as appropriate. Therapeutic formulations typically will be sterile and stable under the conditions of manufacture and storage. The composition can be formulated as a solution, microemulsion, liposome, or other parenteral formulation suitable for administration to a human and may be formulated as a pre-filled device such as a syringe or vial, particular as a single dose.

In one embodiment 2 or more doses are employed in the treatment cycle, for example 2, 3, 4, 5 or 6 doses are employed in each treatment cycle and for example may be provided as a kit.

Each dose administered in a given treatment cycle may be referred to herein as a treatment.

In one embodiment a lower first dose is employed in comparison to the subsequent doses administered in the cycle, for example a lower dose may be in the range of 30-95% of the subsequent dose or doses, for example 50, 60, 70 or 80%.

In one embodiment a higher first is employed in comparison to the subsequent doses administered in the cycle, which may be desirable to full occupy cytokine producing innate immune cells such as the Kupffer cells and thus optimise delivery for subsequent doses.

A higher dose means more than 100% of the subsequent dose, for example 105 to 150% of the subsequent dose, such as 110%, 115%, 120%, 125%, 130%, 135%, 140% or 145% of the subsequent dose.

In one embodiment 1, 2, 3 or all the doses administered contains an equal number of viral particles. This may be particularly advantageous in that it simplifies manufacture of the viral formulation and may in fact provide a highly effective treatment regime.

In one embodiment the "same dose" i.e. the same number of viral particles are administered in one or more doses, such as all the doses in a treatment cycle, however, the doses may be administered at different rates, for example as described herein.

Treatment cycle as employed herein is the period of treatment between a period of rest in a course of treatment repeated in accordance with a schedule with periods of rest there-between.

A treatment cycle generally refers to multiple (i.e. at least two) treatments administered as part of a program or schedule of treatment, administered over a relatively short period of time, for example about 1 to 4 weeks, such as 3 weeks, 2 weeks, or 1 week. Generally, a given treatment cycle will be a part of a larger treatment regime.

In one embodiment the treatment cycle is a period of 14 days or less, for example 10, 9, 8, 7 or 5 days, such as 7 or 5 days.

In one embodiment each further dose or doses is/are administered at approximately 48 hour intervals, such as every 40 to 56 hours. This is advantageous since it allows dosing to occur within a normal working week or within an outpatient setting.

In one embodiment the first dose is administered on day 1 and the further therapeutic doses are administered every second day thereafter, such as on days 1, 3, 5, 7, 9, 11 and 13, or once every approximately 48 hours thereafter, such as every 40 to 56 hours.

In one embodiment the plasma levels of virus in the patient after administration of the dose (such as the second or subsequent dose) is at least $2\times10^6$ viral particles per ml, for example for a period of 15 minutes or longer, for example 20, 30, 40, 50, 60 minutes or more.

In vitro studies performed by the inventors (see FIG. 1) suggest that for virus particles in whole human blood at 37° C., killing drops below 50% at $<2\times10^6$ particles ml. Furthermore, the inventors have been able to show the presence of live viral particles in patient blood using plaque assays when viral genome levels are above for example 1.6e6 to 1e8, and can be consistently detected. In one embodiment there is at least 14 days between treatment cycles.

The formulation will generally comprise a pharmaceutically acceptable diluent or carrier, for example a non-toxic, isotonic carrier that is compatible with the virus, and in which the virus is stable for the requisite period of time.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a dispersant or surfactant such as lecithin or a non-ionic surfactant such as polysorbate 80 or 40.

In dispersions the maintenance of the required particle size may be assisted by the presence of a surfactant. Examples isotonic agents include sugars, polyalcohols such as mannitol, sorbitol, or sodium chloride in the composition.

In one embodiment a sterile isotonic diluent such as saline or glucose (for example 5% glucose is employed).

In one embodiment parenteral formulations employed in the method may comprise one or more of the following a buffer, for example 4-(2-hydroxyethyl)-1-piperazineethanesulfonic acid, a phosphate buffer, and/or a Tris buffer, a sugar for example dextrose, mannose, sucrose or similar, a salt such as sodium chloride, magnesium chloride or potassium chloride, a detergent such as a non-ionic surfactant such as Briji®, PS-80, PS-40 or similar. The formulation may also comprise a preservative such as EDTA or ethanol or a combination of EDTA and ethanol, which are thought to prevent one or more pathways of possible degradation.

In one embodiment the formulation will comprise purified oncolytic virus, for example $1\times10^{10}$ to $1\times10^{14}$ viral particles per dose, such as $1\times10^{10}$ to $7\times10^{12}$ viral particles per dose, in particular $1\times10^{10}$ to $1\times10^{12}$ viral particles per dose, including overage as necessary.

In one embodiment the formulation according to the present disclosure comprises $6\times10^{12}$ viral particles.

In one embodiment the concentration of virus in the formulation is in the range $2\times10^8$ to $2\times10^{14}$ vp/mL, such as $2\times10^{12}$ vp/ml.

In one embodiment the parenteral formulation comprises glycerol.

In one embodiment the formulation comprises oncolytic adenovirus from subgroup B, HEPES (N-2-hydroxyethylpiperazine-N'-2-ethanesulfonic acid), glycerol and buffer.

In one embodiment the parenteral formulation consists of virus, HEPES for example 5 mM, glycerol for example 5-20% (v/v), hydrochloric acid, for example to adjust the pH into the range 7-8 and water for injection.

In one embodiment 0.7 mL of ColoAd1 at a concentration of $2\times10^{12}$ vp/mL is formulated in 5 mM HEPES, 20% glycerol with a final pH of 7.8.

Prolonged absorption of the injectable compositions can be brought about by including in the composition an agent which delays absorption, for example, monostearate salts and gelatin.

Thus the oncolytic adenoviruses employed herein may be administered in a time release formulation, for example in a composition which includes a slow release polymer. The oncolytic adenovirus can be prepared with carriers that will protect it against neutralisation and/or prevent rapid release, such as a controlled release formulation, such as implants and microencapsulated delivery systems.

Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Biocompatible non-degradable polymers such as Polyethylene glycol and poly(N-(2-hydroxypropyl)methacrylamide) can also be used. Many methods for the preparation of such formulations are known to those skilled in the art.

Sterile injectable solutions can be prepared by incorporating the oncolytic adenovirus in the required amount in an appropriate solvent, for example with one or a combination of ingredients described herein, as relevant, followed by filtered sterilisation. Generally, dispersions are prepared by incorporating the oncolytic adenovirus into a sterile vehicle which contains a basic dispersion medium and the required other ingredients.

Generally the parenteral formulation according to the disclosure is a sterile liquid formulation, such as an aqueous formulation, substantially free of particulates, for example prepared aseptically and sterilised by passing through a 0.2 micron filter.

In one embodiment the therapeutic parenteral formulation is administered to minimise the contact of the formulation with the epidermis of the patient, for example employing a sheathed needle or via a cannula. This precaution is thought to minimise the immune response of the patient to the oncolytic virus, for example by minimising contact with Langerhan cells in the skin. Replication capable as employed herein is a virus that can replicate in a host cell. In one embodiment replication capable encompasses replication competent and replication selective viruses.

Replication competent as employed herein is intended to mean an oncolytic adenovirus that is capable of replicating in a human cell, such as a cancer cell, without any additional complementation to that required by wild-type viruses, for example without relying on defective cellular machinery. That is, they are tumour selective by infecting tumour cells in preference to non-tumour cells. ColoAd1 is an example of a replication competent virus.

Replication selective or selective replication as employed herein is intended to mean an oncolytic adenovirus that is able to replicate in cancer cells employing an element which is specific to said cancer cells or upregulated therein, for example defective cellular machinery, such as a p53 mutation, thereby allowing a degree of selectivity over healthy/normal cells.

Oncolytic subgroup B adenovirus as employed herein refers to an adenovirus comprising at least the hexon and fiber from subgroup B (see Shenk et al and Table 1) that preferentially infects and/or lyses tumour cells compared with normal cells. Thus an oncolytic subgroup B adenovirus as employed herein includes a chimeric, a mutant or a variant, with the fiber and hexon of a group B adenovirus and which retains oncolytic properties.

Adenovirus or adenoviral serotype as used herein refers to any of the human adenoviral serotypes currently known (51) or isolated in the future. See for example, Strauss (1984) and Shenk (2001). Adenovirus serotypes are classified into subgroups as shown in Table 1.

Table 1 shows the division of adenovirus serotvnes:

| Subgroup | Adenoviral Serotype |
|---|---|
| A | 12, 18, 31 |
| B | 3, 7, 11, 14, 16, 21, 34, 35, 51 |
| C | 1, 2, 5, 6 |
| D | 8-10, 13, 15, 17, 19, 20, 22-30, 32, 33, 36-39, 42-50 |
| E | 4 |
| F | 40, 41 |

Examples of subgroup B viruses include Ad11 (wild-type) such as Ad11a and Ad11p (Genbank Accession No: AF532578) and the chimeric adenovirus ColoAd1. The latter is disclosed in WO 2005/118825 and the full sequence for the virus is provided in SEQ ID NO: 1 therein.

Thus in one embodiment the virus employed in the method according to the present disclosure is a chimeric virus.

Chimeric adenovirus as employed herein refers to adenoviruses which have DNA from two or more different adenovirus serotypes such as those generated using the method of WO2005/118825 which is incorporated herein by reference.

In one embodiment the chimeric adenovirus is ColoAd1. ColoAd1 is thought to kill tumour cells by a mechanism which more closely resembles necrosis than apoptosis (unpublished data produced at the University of Oxford). This has a number of potential beneficial effects (Kirn et al 2001; Small et al 2006; Reid et al 2002; Liu et al 2007; Ferguson et al 2012):

ColoAd1 has been shown to be potent in multi-drug resistant cancer cell lines and in cancer stem-cell like cells, which are known to have a resistance to apoptosis;

An inflammatory necrotic cell death may be more suitable for the generation of a specific anti-tumoural immune response;

ColoAd1 exits tumour cells very rapidly, even before target cell death, and may thus have enhanced ability to spread.

ColoAd1 is a chimera of Ad11 and Ad3 but has an outer capsule which is entirely homologous with that of Ad11. The viral kinetics, inflammatory potential and immunological characteristics of ColoAd1 thus most closely resemble and predict those of Ad11 and other subgroup B adenoviruses.

In one embodiment the oncolytic virus employed in the method of the present disclosure is deleted in the E3 and/or E4 region or part thereof. This may be beneficial because it may allow more rapid replication of the virus in vivo.

In addition the E3 deletion may contribute to the rapid clearance of the virus from non-cancer cells as the E3 region encoded proteins which may be relevant to avoiding the immunity of the host.

In one embodiment the virus employed in the method of the present disclosure is based on Ad11 or derived therefrom such that the hexon and fibre are substantially similar to Ad11, such as Ad11p. Furthermore since the serotype designation of adenovirus is based on the exterior properties of the virus i.e. hexon and fibre properties, the present disclosure is useful in type B adenovirus which have similar surface properties.

In one embodiment the type B adenovirus is OvAd1 or OvAd2 which are disclosed in SEQ ID NO: 1 and SEQ ID NO: 2 respectively in WO2008/080003, incorporated herein by reference.

Substantially similar as employed herein refers to an amino acid sequence for a relevant protein or proteins which is/are at least 95% identical (e.g. 96, 97, 98, 99 or 100% identical) over the "whole" of the particular protein. The protein(s) being compared may be part of a larger entity but the comparison will be the whole length of the relevant fragment or component.

Adenovirus type 5 (Ad5) generally enter the cell via the coxsackie-adenovirus receptor (CAR). However, Adenovirus serotype 11 (Ad11) is a subgroup B adenovirus that targets a different receptor (CD46) which is expressed at low levels in all nucleated cells. In normal cells CD46 is often hidden on the basolateral surfaces of cells and is thus not available for virus binding (Varela J C, et al Intl Cancer 2008 Sep. 15; 123(6):1357-63; Maisner et al., 1997). However, in tumour cells it typically has enhanced surface expression, particularly in more advanced and aggressive tumours (Kinugasa et al., 1999). Therefore, Ad11 efficiently infects carcinoma cell lines, for example from lung epithelial carcinoma (A549 cells), hepatoma (HepG2), prostatic cancer (DU 145 and LNCaP), laryngeal cancer (Hep2) and breast cancer (CAMA and MG7) and also to glioblastoma, medulloblastoma and neuroblastoma cells (Mei et al 2003). Thus Ad11 preferentially infects tumour cells and viruses derived therefrom are thought to be useful in the treatment of at least one or more of the above cancers. As a chimera of Ad11 and Ad3, ColoAd1 shares these characteristics with Ad11.

In one embodiment a virus employed in the method of the present disclosure comprises a transgene (in particular one or more transgenes), for example a therapeutic transgene, for expression in vivo. A transgene gene as employed herein is intended to refer to a gene not found in the parent or wild type virus. Such genes may perform a function as a marker or reporter for tracking efficacy of viral infection. Alternatively the gene may perform a role in improving the efficacy of the virus. Alternatively the gene may deliver a cytotoxic agent to the cell.

The therapeutic transgene may express a therapeutic agent in the cell, for example siRNA; shRNA; a polypeptide; tumour associated antigen (TAA), cytokine; antibody; or an anti-angiogenesis factor.

Examples of therapeutic antibodies include anti-VGEF antibodies such as bevacizumab, anti-EGFR antibodies such as cetuximab, an anti-CD20 antibody such as rituximab, or an immune system activator modulator such as anti-CTLA4 (e.g. ipilimumab), anti-PD-1 and anti-PD-L1 amongst others. Single chain antibodies, antibody subunits, antibody fragments and TRAPs may also be encoded as well as full length antibodies. Importantly for the current disclosure, the inclusion of these proteins does not change the surface properties of the virus and therefore can readily be incorporated into the genome without deleterious effects upon the dosing as described herein whilst providing additional therapeutic mechanisms for attacking the cancer cells.

Examples of cytokines include interferon-alpha, interferon-gamma and IL-2 amongst others.

As the RNA, antibody, polypeptide, TAA or cytokine will be expressed in the tumour it is thought that this presents an opportunity to change the microenvironment of the tumour but avoid systemic side effects of the delivered agent. For example, it may be possible to stimulate the local immune system to attack the cancer. It is possible to modulate this local effect by altering whether or not the RNA, antibody, polypeptide, TAA or cytokine is secreted from the cell and when during the viral life cycle it is expressed.

In one embodiment the transgene encodes thymidine kinase, for example from a non-human origin or cytosine deaminase, for example from bacterial origin or from a yeast.

In one embodiment the antibody, polypeptide or cytokine or similar is non-human in origin and is not humanised. The latter is not likely to detrimentally effect the activity of the entity in the cancer cell and has the advantage that material that may escape the cancer cell will attract the attention of the immune system locally and will be rapidly cleared.

In one embodiment the virus encodes and expresses in vivo a visible or visualisable protein, for example a fluorescent protein, such as GFP or similar. Given the virus selectively infects cancerous cells, when it expresses a visible or visualisable protein then it can be used to highlight the area of cancerous tissue for resection or radiation.

In one embodiment, the viruses may be armed with therapeutic genes capable of eliciting anti-tumour immune function, inhibition of tumour neovascularization, or prodrug activation. Therapeutic dose as employed herein refers to the amount of oncolytic adenovirus that is suitable for achieving the intended therapeutic effect when employed in a suitable treatment regimen, for example ameliorates symptoms or conditions of a disease. A dose may be considered a therapeutic dose in the treatment of cancer or metastases when the number of viral particles may be sufficient to result in the following: tumour or metastatic growth is slowed or stopped, or the tumour or metastasis is found to shrink in size, and/or the life span of the patient is extended. Suitable therapeutic doses are generally a balance between therapeutic effect and tolerable toxicity, for example where the side-effect and toxicity are tolerable given the benefit achieved by the therapy.

In one embodiment the therapeutic dose range does not have a dose limiting toxicity.

Dose limiting toxicity as employed herein means the appearance of side effects during treatment that are severe enough to prevent any one of the following: further increase in dosage, frequency or strength or to prevent continuation of treatment at any dosage level. Toxicity effects which are intolerable, for example associated with a high dose mean the latter is not suitable for use as a therapeutic dose in the context of the present disclosure.

In one embodiment pre-existing immunity to the Ad11 capsid is weak permitting effective administration of further therapeutic doses on or after day 7.

In one embodiment the poor immune stimulatory properties of the Ad11 capsid permits effective administration of further therapeutic doses on or after day 7.

In one embodiment intravenous delivery of the virus is less immunogenic in terms of antiviral immunogenicity than sub-cutaneous or intramuscular delivery of virus.

It is generally believed that the toxicity of Ad11 may be lower than certain other adenoviruses, such as Ad5. This together with the lower seroprevalence is beneficial but this may not be sufficient to allow Ad11 to evade immune responses. Even though the literature suggests that the subgroup B adenoviruses are not toxic to liver cells it may be that macrophages in the lungs, liver (Kupffer cells) and spleen clear oncolytic viruses after systemic delivery.

It is thought that the rapid delivery of at least two doses of the oncolytic virus may be beneficial in generating sufficient levels of virus that are sustained for a period which allows adequate infection of the target cells, namely cancer cells.

Providing at least two doses in quick succession may allow one or more the following beneficial events to occur a) the immune mechanisms are occupied by the first dose, which may then allow the second dose to escape the full onslaught of the immune system to reach the target and/or b) at least two doses in quick succession allow the biodistribution of the virus to reach sufficient levels for a sufficient period to reach the target cells in vivo, either way once the virus reaches and infects the target cells it is able to replicate.

Biodistribution as employed herein means the distribution in vivo.

Whilst not wishing to be bound by theory the inventors believe that the first dose of virus may down regulate clearance, for example mechanisms such as those employing cytokine producing innate immune cells such as Kupffer cells thereby improving the bioavailablity for the further therapeutic dose(s). The first dose of virus may thus "deplete" the phagocytic 'sinks' for circulating virus thereby achieving better delivery and/or increased efficacy. Depleting the phagocytic sinks also reduces the tendency to release cytokines on subsequent doses and thus allows higher viral blood levels to be achieved without excessive toxicity.

Bioavailability as employed herein means the amount of virus available to perform its intended therapeutic function in vivo.

In one embodiment the method herein wherein at least three doses are administered minimises side-effects and/or toxicity in the patient.

In one embodiment the adenovirus is stealthed by coating said virus with a polymer, for example to at least partially avoid the patient's immune system.

Stealthed as employed herein means that the adenovirus's exterior surface has been modified to avoid the patient's immune response, for example employing a polymer. Examples of suitable polymers are disclosed in WO98/19710, WO00/74722, WO2010/067041, WO2010/067081, and WO2006/008513 incorporated herein by reference.

In one embodiment the oncolytic virus is conjugated to a cytotoxic or immunomodulatory agent.

In one embodiment the oncolytic adenovirus is provided which is pegylated, for example to reduce immunogenenicity and/or increase half-life.

In one embodiment the method of treatment is for use in the treatment of a tumour.

Tumour as employed herein is intended to refer to an abnormal mass of tissue that results from excessive cell division that is uncontrolled and progressive, also called a neoplasm. They may be either benign (not cancerous) or malignant. Tumour encompasses all forms of cancer and metastases.

In one embodiment the tumour is a solid tumour. The solid tumour may be localised or metastasised.

In one embodiment the tumour is of epithelial origin.

In one embodiment the tumour is a solid tumour.

In one embodiment the tumour is a malignancy, such as colorectal cancer, hepatoma (liver cancer), prostate cancer, pancreatic cancer, breast cancer, ovarian cancer, thyroid cancer, renal cancer, bladder cancer, head and neck cancer or lung cancer.

In one embodiment the tumour is a colorectal malignancy.

Malignancy as employed herein means cancerous cells.

In one embodiment the cancer is colorectal cancer and/or metastatic forms thereof such as liver metastasis.

In one embodiment the cancer is liver cancer and/or metastatic forms thereof.

In one embodiment the cancer is lung cancer and/or metastatic forms thereof.

In one embodiment the cancer is ovarian cancer and/or metastatic forms thereof, such as lung metastasis.

In one embodiment the cancer is renal cancer and/or metastatic forms thereof.

In one embodiment the cancer is bladder cancer and/or metastatic forms thereof.

In one embodiment the cancer is throat cancer.

In one embodiment the cancer is skin cancer, such as melanoma. In one embodiment the cancer is Leukemia. In one embodiment the cancer is glioblastoma, medulloblastoma or neuroblastoma. In one embodiment the cancer is a neuroendocrine cancer. In one embodiment the cancer is Hodgkin's or non-Hodgkins lymphoma.

In one embodiment the oncolytic adenovirus is employed in the treatment or prevention of metastasis.

In one embodiment the oncolytic adenoviruses described herein are suitable for the treatment of cancerous cells that have migrated to the lymph node. The present inventors have shown that oncolytic virus administered to colorectal cancer patients can infect cancerous cells that have migrated to the lymph nodes.

In one embodiment the virus, formulations and regimens according to the present disclosure are suitable for treating abnormal pre-cancerous cells.

In one embodiment the method or formulation herein is employed in the treatment of drug resistant cancers.

In one embodiment the method or formulation is employed in to sensitise drug resistant to cancers to said drugs.

Cancer Types in More Detail

Lung Cancer

Lung cancers are classified according to histological type and are categorized by the size and appearance of the malignant cells seen by a histopathologist under a microscope. For therapeutic purpose, two broad classes are distinguished: non-small cell lung carcinoma and small cell lung carcinoma.

In one embodiment the epithelial cancer is lung cancer, for example small-cell lung cancer (SCLC) and non-small-cell lung cancer (NSCLC).

Non-small-cell lung carcinoma—The three main subtypes of NSCLC are adenocarcinoma, squamous-cell carcinoma and large-cell carcinoma.

Nearly 40% of lung cancers are adenocarcinoma, which usually originates in peripheral lung tissue. A subtype of adenocarcinoma, the bronchioloalveolar carcinoma, is more common in female never-smokers, and may have a better long term survival.

Squamous-cell carcinoma accounts for about 30% of lung cancers. They typically occur close to large airways. A hollow cavity and associated cell death are commonly found at the center of the tumour. About 9% of lung cancers are large-cell carcinoma. These are so named because the cancer cells are large, with excess cytoplasm, large nuclei and conspicuous nucleoli.

Small-cell lung carcinoma—In small-cell lung carcinoma (SCLC), the cells contain dense neurosecretory granules (vesicles containing neuroendocrine hormones), which give this tumour an endocrine/paraneoplastic syndrome association. Most cases arise in the larger airways (primary and secondary bronchi). These cancers grow quickly and spread early in the course of the disease. Sixty to seventy percent have metastatic disease at presentation.

In one embodiment the cancer is non-small lung carcinoma.

Liver Cancer

In one embodiment the cancer is liver cancer, for example a liver metastasis from a primary cancer, for example colon cancer, which has spread to the liver. In one embodiment the liver cancer is hepatocellular carcinoma (HCC).

Renal Cancer

In one embodiment there is provided treatment of renal cancer, for example renal cell carcinoma and/or urothelial cell carcinoma using an oncolytic adenovirus as disclosed herein. Other examples of renal cancer include squamous cell carcinoma, juxtaglomerular cell tumour (reninoma), angiomyolipoma, renal oncocytoma, Bellini duct carcinoma, clear-cell sarcoma of the kidney, mesoblastic nephroma, Wilms' tumour, mixed epithelial stromal tumour, clear cell adenocarcinoma, transitional cell carcinoma, inverted papilloma, renal lymphoma, teratoma, carcinosarcoma, and carcinoid tumour of the renal pelvis.

Bladder Cancer

In one embodiment the cancer is bladder cancer, for example is any of several types of malignancy arising from the epithelial lining (i.e., the urothelium) of the urinary bladder. About 90% of bladder cancers are transitional cell carcinoma. The other 10% are squamous cell carcinoma, adenocarcinoma, sarcoma, small cell carcinoma, and secondary deposits from cancers elsewhere in the body. The staging of is given below.

T (Primary Tumour)

TX Primary tumour cannot be assessed

T0 No evidence of primary tumour

Ta Non-invasive papillary carcinoma

Tis Carcinoma in situ ('flat tumour')

T1 Tumour invades subepithelial connective tissue

T2a Tumour invades superficial muscle (inner half)

T2b Tumour invades deep muscle (outer half)

T3 Tumour invades perivesical tissue:

T3a Microscopically

T3b Macroscopically (extravesical mass)

T4a Tumour invades prostate, uterus or vagina

T4b Tumour invades pelvic wall or abdominal wall

N (Lymph Nodes)

NX Regional lymph nodes cannot be assessed

N0 No regional lymph node metastasis

N1 Metastasis in a single lymph node 2 cm or less in greatest dimension

N2 Metastasis in a single lymph node more than 2 cm but not more than 5 cm in greatest dimension, or multiple lymph nodes, none more than 5 cm in greatest dimension N3 Metastasis in a lymph node more than 5 cm in greatest dimension M (Distant Metastasis)

MX Distant metastasis cannot be assessed

M0 No distant metastasis

M1 Distant metastasis.

The current disclosure extends to any stage of bladder cancer.

Ovarian Cancer

In an independent aspect the present disclosure relates to ColoAd1, a formulation of the same or a combination therapy comprising ColoAd1, for use in treating ovarian cancer, for example administering a therapeutically effective amount of ColoAd1 to a patient with ovarian cancer, for example employing a dosing regimen described herein.

There are more than 30 different types of ovarian cancer which are classified according to the type of cell from which they start. Cancerous ovarian tumours can start from three common cell types:

Surface Epithelium—cells covering the lining of the ovaries

Germ Cells—cells that are destined to form eggs

Stromal Cells—Cells that release hormones and connect the different structures of the ovaries The present disclosure relates to treatment of ovarian cancer from any source, for example as described herein, in particular epithelium cells. Epithelial ovarian carcinomas (EOCs) account for 85 to 90 percent of all cancers of the ovaries.

Common Epithelial Tumours—Epithelial ovarian tumours develop from the cells that cover the outer surface of the ovary. Most epithelial ovarian tumours are benign (noncancerous). There are several types of benign epithelial tumours, including serous adenomas, mucinous adenomas, and Brenner tumours. Cancerous epithelial tumours are carcinomas—meaning they begin in the tissue that lines the ovaries. These are the most common and most dangerous of all types of ovarian cancers. Unfortunately, almost 70 percent of women with the common epithelial ovarian cancer are not diagnosed until the disease is advanced in stage.

There are some ovarian epithelial tumours whose appearance under the microscope does not clearly identify them as cancerous. These are called borderline tumours or tumours of low malignant potential (LMP tumours). The method of the present disclosure includes treatment of the latter.

Germ Cell Tumours—Ovarian germ cell tumours develop from the cells that produce the ova or eggs. Most germ cell tumours are benign (non-cancerous), although some are cancerous and may be life threatening. The most common germ cell malignancies are maturing teratomas, dysgerminomas, and endodermal sinus tumours. Germ cell malignancies occur most often in teenagers and women in their twenties. Today, 90 percent of patients with ovarian germ cell malignancies can be cured and their fertility preserved.

Stromal Tumours—Ovarian stromal tumours are a rare class of tumours that develop from connective tissue cells that hold the ovary together and those that produce the female hormones, estrogen and progesterone. The most common types are granulosa-theca tumours and Sertoli-Leydig cell tumours. These tumours are quite rare and are usually considered low-grade cancers, with approximately 70 percent presenting as Stage I disease (cancer is limited to one or both ovaries).

Primary Peritoneal Carcinoma—The removal of one's ovaries eliminates the risk for ovarian cancer, but not the risk for a less common cancer called Primary Peritoneal Carcinoma. Primary Peritoneal Carcinoma is closely rated to epithelial ovarian cancer (most common type). It develops in cells from the peritoneum (abdominal lining) and looks the same under a microscope. It is similar in symptoms, spread and treatment.

Stages of Ovarian Cancer

Once diagnosed with ovarian cancer, the stage of a tumour can be determined during surgery, when the doctor can tell if the cancer has spread outside the ovaries. There are four stages of ovarian cancer—Stage I (early disease) to Stage IV (advanced disease). The treatment plan and prognosis (the probable course and outcome of your disease) will be determined by the stage of cancer you have.

Following is a description of the various stages of ovarian cancer:

Stage I—Growth of the cancer is limited to the ovary or ovaries.

Stage IA—Growth is limited to one ovary and the tumour is confined to the inside of the ovary. There is no cancer on the outer surface of the ovary. There are no ascites present containing malignant cells. The capsule is intact.

Stage IB—Growth is limited to both ovaries without any tumour on their outer surfaces. There are no ascites present containing malignant cells. The capsule is intact.

Stage IC—The tumour is classified as either Stage IA or IB and one or more of the following are present: (1) tumour is present on the outer surface of one or both ovaries; (2) the capsule has ruptured; and (3) there are ascites containing malignant cells or with positive peritoneal washings.

Stage II—Growth of the cancer involves one or both ovaries with pelvic extension.

Stage IIA—The cancer has extended to and/or involves the uterus or the fallopian tubes, or both.

Stage IIB—The cancer has extended to other pelvic organs.

Stage IIC—The tumour is classified as either Stage IIA or IIB and one or more of the following are present: (1) tumour is present on the outer surface of one or both ovaries; (2) the capsule has ruptured; and (3) there are ascites containing malignant cells or with positive peritoneal washings.

Stage III—Growth of the cancer involves one or both ovaries, and one or both of the following are present: (1) the cancer has spread beyond the pelvis to the lining of the abdomen; and (2) the cancer has spread to lymph nodes. The tumour is limited to the true pelvis but with histologically proven malignant extension to the small bowel or omentum.

Stage IIIA—During the staging operation, the practitioner can see cancer involving one or both of the ovaries, but no cancer is grossly visible in the abdomen and it has not spread to lymph nodes. However, when biopsies are checked under a microscope, very small deposits of cancer are found in the abdominal peritoneal surfaces.

Stage IIIB—The tumour is in one or both ovaries, and deposits of cancer are present in the abdomen that are large enough for the surgeon to see but not exceeding 2 cm in diameter. The cancer has not spread to the lymph nodes.

Stage IIIC—The tumour is in one or both ovaries, and one or both of the following is present: (1) the cancer has spread to lymph nodes; and/or (2) the deposits of cancer exceed 2 cm in diameter and are found in the abdomen.

Stage IV—This is the most advanced stage of ovarian cancer. Growth of the cancer involves one or both ovaries and distant metastases (spread of the cancer to organs located outside of the peritoneal cavity) have occurred. Finding ovarian cancer cells in pleural fluid (from the cavity which surrounds the lungs) is also evidence of stage IV disease.

In one embodiment the ovarian cancer is: type I, for example IA, IB or IC; type II, for example IIA, IIB or IIC; type III, for example IIIA, IIIB or IIIC; or type IV.

The present disclosure relates to treatment of any stage of ovarian cancer, in particular as described herein.

Combination Therapy

In one embodiment the virus is administered in combination with the administration of a further cancer treatment or therapy.

"In combination" as employed herein is intended to encompass where the oncolytic virus is administered before, concurrently and/or post cancer treatment or therapy.

In one embodiment the oncolytic adenovirus is employed in combination with high intensity focused ultrasound (HIFU) treatment.

Cancer therapy includes surgery, radiation therapy, targeted therapy and/or chemotherapy.

Cancer treatment as employed herein refers to treatment with a therapeutic compound or biological agent, for example an antibody intended to treat the cancer and/or maintenance therapy thereof.

In one embodiment the cancer treatment is selected from any other anti-cancer therapy including a chemotherapeutic agent, a targeted anticancer agent, radiotherapy, radio-isotope therapy or any combination thereof.

In a further independent aspect the present disclosure relates to a combination therapy comprising oncolytic type B adenovirus, such as ColoAd1, and a chemotherapeutic agent which does not interfere with the adenovirus activity. Type B adenovirus, such as ColoAd1 as employed herein includes formulations thereof, for example pharmaceutical formulations thereof.

Activity as employed herein refers to any beneficial property or characteristic of the virus, for example the oncolytic activity and or the ability of the virus to replicate in cancer cells, such as viral replication in vivo.

In one embodiment the ColoAd1 in the combination therapy is dosed according to a regimen described herein.

Generally, the combination therapy will be provided as a formulation of the adenovirus and a formulation of the chemotherapeutic agent. Thus the administration of the adenovirus and the chemotherapeutic will suitably be separate events. These administrations may be on the same or different days.

In one embodiment the adenovirus is administered in a suitable regime one week and the chemotherapeutic is administer a following week, for example the next.

In one or more embodiments the chemotherapeutic agent and the adenovirus may have a synergistic therapeutic effect.

The oncolytic adenovirus may be used as a pre-treatment to the therapy, such as a surgery (neoadjuvant therapy), to shrink the tumour, to treat metastasis and/or prevent metastasis or further metastasis. The oncolytic adenovirus may be used after the therapy, such as a surgery (adjuvant therapy), to treat metastasis and/or prevent metastasis or further metastasis.

Concurrently as employed herein is the administration of the additional cancer treatment at the same time or approximately the same time as the oncolytic adenovirus formulation. The treatment may be contained within the same formulation or administered as a separate formulation.

In one embodiment the virus is administered in combination with the administration of a chemotherapeutic agent, for example as described herein, such as paclitaxel, abraxane or similar.

Chemotherapeutic agent as employed herein is intended to refer to specific antineoplastic chemical agents or drugs that are selectively destructive to malignant cells and tissues. For example alkylating agents, antimetabolites, anthracyclines, plant alkaloids, topoisomerase inhibitors, and other antitumour agents. Other examples of chemotherapy include doxorubicin, 5-fluorouracil (5-FU), paclitaxel, capecitabine, irinotecan, and platins such as cisplatin and oxaliplatin. The preferred dose may be chosen by the practitioner based on the nature of the cancer being treated.

Surprisingly the present inventors have established that certain classes of therapeutic agents can inhibit viral replication, for example topoisomerase or parp inhibitors, may inhibit the replication of the virus in vivo. Given it is thought to be desirable to establish a viral infection in a cancer cell such that the virus can replicate, then co-administration of compounds that inhibit viral replication is likely to be undesirable.

In one embodiment the chemotherapeutic agent is not an enzyme inhibitor. Thus in one embodiment the combination therapy does not employ a topoisomerase inhibitor.

In one embodiment he chemotherapeutic agent is not a parp inhibitor.

In one embodiment the combination therapy employs a platinum containing chemotherapeutic agent, for example cisplatin, carboplatin or oxaliplatin.

In one embodiment the combination employs a microtubule inhibitor, for example vincristine sulphate, epothilone A, N-[2-[(4-Hydroxyphenyl)amino]-3-pyridinyl]-4-methoxybenzenesulfonamide (ABT-751), ataxol derived chemotherapeutic agent, for example paclitaxel, abraxane, or docetaxel or a combination thereof.

In one embodiment the combination employs an mTor inhibitor. Examples of mTor inhibitors include: everolimus (RAD001), WYE-354, KU-0063794, papamycin (Sirolimus), Temsirolimus, Deforolimus(MK-8669), AZD8055 and BEZ235(NVP-BEZ235).

In one embodiment the combination employs a Pi3 Kinase inhibitor. Examples of Pi3 kinases inhibitors include: GDC-0941, ZSTK474, PIK-90, LY294002, TG100-115, XL147, GDC-0941, ZSTK474, PIK-90, LY294002, TG100-115, XL147, AS-605240, PIK-293, AZD6482, PIK-93, TGX-221, IC-87114, AS-605240, P1K-293, AZD6482, PIK-93, TGX-221, IC-87114 and compounds disclosed in WO2011/048111 incorporated herein by reference including 2-((4-Amino-3-(3-hydroxyphenyl)-1H-pyrazolo[3,4-d]pyrimidin-1-yl)methyl)-3-(2-chlorobenzyl)-5-ethynylquinazolin-4(3H)-one; 2-((4-Amino-3-(3-hydroxyphenyl)-1H-pyrazolo[3,4-d]pyrimidin-1-yl)methyl)-3-(2-chlorobenzyl)-5-(3-(2-(2-methoxyethoxy)ethoxy)prop-1-yn-1-yl)quinazolin-4(3H)-one; 2-((4-Amino-3-(3-hydroxyphenyl)-1H-pyrazolo[3,4-d]pyrimidin-1-yl)methyl)-3-(2-chlorobenzyl)-5-(6-morpholino-6-oxohex-1-yn-1-yl)quinazolin-4(3H)-one; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)hex-5-ynoic acid; 2-((4-Amino-3-(4-hydroxyphenyl)-1H-pyrazolo[3,4-d]pyrimidin-1-yl)methyl)-3-(2-chlorobenzyl)-5-(6-morpholino-6-oxohex-1-yn-1-yl)quinazolin-4(3H)-one; 3-((2-((4-Amino-3-(3-hydroxyphenyl)-1H-pyrazolo[3,4-d]pyrimidin-1-yl)methyl)-5-(3-(2-(2-hydroxyethoxy)ethoxy)prop-1-yn-1-yl)-4-oxoquinazolin-3(4H)-yl)methyl) benzonitrile; 2-((4-amino-3-(3-hydroxyphenyl)-1H-pyrazolo[3,4-d]pyrimidin-1-yl)methyl)-3-(2-chlorobenzyl)-5-(3-(2-morpholinoethoxy)prop-1-ynyl)quinazolin-4(3H)-one; 2-((4-Amino-3-(4-hydroxyphenyl)-1H-pyrazolo[3,4-d]pyrimidin-1-yl)methyl)-3-(2-chloro benzyl)-5-ethynylquinazolin-4(3H)-one; 2-((4-Amino-3-(3-hydroxyphenyl)-1H-pyrazolo[3,4-d]pyrimidin-1-yl)methyl)-3-(3-chlorobenzyl)-5-ethynylquinazolin-4(3H)-one; 2-((4-Amino-3-(4-hydroxyphenyl)-1H-pyrazolo[3,4-d]pyrimidin-1-yl) methyl)-3-(3-chlorobenzyl)-5-ethynyl quinazolin-4(3H)- one; 2-((4-Amino-3-(3-hydroxyphenyl)-1H-pyrazolo[3,4-d]pyrimidin-1-yl)methyl)-5-ethynyl-3-(2-fluorobenzyl)quinazolin-4(3H)-one; 2-((4-Amino-3-(4-hydroxy phenyl)-1H-pyrazolo[3,4-c]pyrimidin-1-yl)methyl)-5-ethynyl-3-(2-fluorobenzyl) quinazolin-4 (3H)-one; 2-((4-Amino-3-(4-hydroxyphenyl)-1H-pyrazolo[3,4-d]pyrimidin-1-yl)methyl)-5-ethynyl-3-(3-methoxybenzyl)quinazolin-4(3H)-one; 2-((4-Amino-3-(3-hydroxyphenyl)-1H-pyrazolo[3,4-d]pyrimidin-1-yl)methyl)-5-ethynyl-3-(3-methoxybenzyl)quinazolin-4(3H)-one; 2-((4-Amino-3-(4-hydroxyphenyl)-1H-pyrazolo[3,4-d]pyrimidin-1-yl)methyl)-5-ethynyl-3-(3-(tri-fluoromethyl)benzyl)quinazolin-4(3H)-one; 2-((4-Amino-3-(3-hydroxyphenyl)-1H-pyrazolo[3,4-d]pyrimidin-1-yl)methyl)-5-ethynyl-3-(3-(trifluoromethyl) benzyl)quinazolin-4(3H)-one; 2-((4-Amino-3-(4-hydroxyphenyl)-1H-pyrazolo[3,4-d]pyrimidin-1-yl)methyl)-3-(4-chlorobenzyl)-5-ethynyl quinazolin-4(3H)-one; 2-((4-Amino-3-(3-hydroxyphenyl)-1H-pyrazolo[3,4-d]pyrimidin-1-yl)methyl)-5-ethynyl-3-(4-(methylsulfonyl) benzyl)quinazolin-4(3H)-one; 2-((4-Amino-3-(4-hydroxyphenyl)-1H-pyrazolo[3,4-d]pyrimidin-1-yl)methyl)-5-ethynyl-3-(4-(methyl-sulfonyl)benzyl)quinazolin-4(3H)-one; 2-((4-Amino-3-(3-hydroxyphenyl)-1H-pyrazolo[3,4-d]pyrimidin-1-yl)methyl)-5-ethynyl-3-(4-(trifluoromethyl) benzyl) quinazolin-4(3H)-one; 3-((2-((4-Amino-3-(4-hydroxyphenyl)-1H-pyrazolo[3,4-d]pyrimidin-1-yl)methyl)-5-ethynyl-4-oxo-quinazolin-3(4H)-yl)methyl) benzonitrile; 2-((4-Amino-3-(3-hydroxyphenyl)-1H-pyrazolo[3,4-d]pyrimidin-1-yl)methyl)-5-ethynyl-3-(3-(methyl-sulfonyl)benzyl)quinazolin-4(3H)-one; 3-((2-((4-Amino-3-(3-hydroxyphenyl)-1H-pyrazolo[3,4-d]pyrimidin-1-yl)methyl)-5-ethynyl-4-oxo-quinazolin-3(4H)-yl)methyl) benzonitrile; 2-((4-Amino-3-(3-hydroxyphenyl)-1H-pyrazolo[3,4-d]pyrimidin-1-yl)methyl)-3-(4-chlorobenzyl)-5-ethynylquinazolin-4(3H)-one; 2-((4-Amino-3-(3-hydroxyphenyl)-1H-pyrazolo[3,4-d]pyrimidin-1-yl)methyl)-3-(4-chlorobenzyl)-5-(3-methoxy-prop-1-ynyl) quinazolin-4(3H)-one; 2-((4-Amino-3-(4-hydroxyphenyl)-1H-pyrazolo[3,4-cl]pyrimidin-1-yl)methyl)-3-(3-methoxybenzyl)-5-(3-methoxyprop-1-ynyl) quinazolin-4 (3H)-one; 2-((4-Amino-3-(4-hydroxyphenyl)-1H-pyrazolo[3,4-d]pyrimidin-1-yl)methyl)-3-(2-chlorobenzyl)-5-(3-methoxyprop-1-ynyl)quinazolin-4(3H)-one; 2-((4-Amino-3-(4-hydroxyphenyl)-1H-pyrazolo[3,4-d]pyrimidin-1-yl)methyl)-5-ethynyl-3-(4-(trifluoro methyl)benzyl) quinazolin-4(3H)-one; 2-((4-Amino-3-(3-hydroxyphenyl)-1H-pyrazolo[3,4-d]pyrimidin-1-yl)methyl)-3-(2-chlorobenzyl)-5-(3-(2-methoxyethoxy)prop-1-ynyl) quinazolin-4(3H)-one; 2-((4-Amino-3-(3-hydroxyphenyl)-1H-pyrazolo[3,4-d]pyrimidin-1-yl)methyl)-5-ethynyl-3-((5-methylisoxazol-3-yl)methyl)quinazolin-4(3H)-one; 2-((4-Amino-3-(4-hydroxyphenyl)-1H-pyrazolo[3,4-d]pyrimidin-1-yl)methyl)-5-ethynyl-3-((5-methylisoxazol-3-yl)methyl) quinazolin-4(3H)-one; 2-((4-Amino-3-(4-hydroxyphenyl)-1H-pyrazolo[3,4-d]pyrimidin-1-yl)methyl)-3-(3-chloro-2-fluoro-benzyl)-5-ethynylquinazolin-4(3H)-one; 2-((4-Amino-3-(4-hydroxyphenyl)-1H-pyrazolo[3,4-d]pyrimidin-1-yl)methyl)-3-(2,6-difluorobenzyl)-5-ethynylquinazolin-4 (3H)-one; 2-((4-Amino-3-(4-hydroxyphenyl)-1H-pyrazolo[3,4-c]pyrimidin-1-yl)methyl)-3-(4-chloro-2-fluorobenzyl)-5-ethynylquinazolin-4(3H)-one; 2-((4-Amino-3-(3-fluoro-4-hydroxyphenyl)-1H-pyrazolo[3,4-d]pyrimidin-1-yl)methyl)-3-(2-chlorobenzyl)-5-ethynylquinazolin-4(3H)-one; 2-((4-Amino-3-(3-hydroxyphenyl)-1H-pyrazolo[3,4-c]pyrimidin-1-yl)methyl)-5-(3-methoxyprop-1-ynyl)-3-(3-(trifluoromethyl)benzyl)quinazolin-4(3H)-one; 2-((4-Amino-3-(4-hydroxyphenyl)-1H-pyrazolo[3,4-c]pyrimidin-1-yl)methyl)-5-ethynyl-3-(4-fluorobenzyl) quinazolin-4 (3H)-one; 2-((4-Amino-3-(4-hydroxyphenyl)-1H-pyrazolo[3,4-d]pyrimidin-1-yl)methyl)-3-(2-chlorobenzyl)-5-(3-cyclopentylprop-1-ynyl)quinazolin-4(3H)-one; 2-((4-Amino-3-(4-hydroxyphenyl)-1H-pyrazolo[3,4-d]pyrimidin-1-yl) methyl)-5-(3-(benzyloxy)prop-1-ynyl)-3-(2-chloro-benzyl) quinazolin-4(3H)-one; 2-((4-Amino-3-(4-hydroxyphenyl)-1H-pyrazolo[3,4-d]pyrimidin-1-yl)methyl)-3-(2-chlorobenzyl)-5-(5-hydroxypent-1-ynyl)quinazolin-4(3H)-one; 21(4-Amino-3-(4-hydroxyphenyl)-1H-pyrazolo[3,4-d]pyrimidin-1-yl)methyl)-5-ethynyl-3-(2-fluoro-5-methoxybenzyl)quinazolin-4(3H)-one; 2-((4-Amino-3-(4-hydroxyphenyl)-1H-pyrazolo[3,4-d]pyrimidin-1-yl)methyl)-3-(3,4-dichlorobenzyl)-5-ethynylquinazolin-4(3H)-one; 2-((4-Amino-3-(4-hydroxyphenyl)-1H-pyrazolo[3,4-d]pyrimidin-1-yl)methyl)-3-benzyl-5-ethynylquinazolin-4 (3H)-one; 2-((4-Amino-3-(4-hydroxyphenyl)-1H-pyrazolo[3,4-d]pyrimidin-1-yl)methyl)-5-ethynyl-3-(2-trifluoromethylbenzyl)quinazolin-4(3H)-one; 2-((4-Amino-3-(4-hydroxyphenyl)-1H-pyrazolo[3,4-d]pyrimidin-1-yl)methyl)-5-ethynyl-3-(4-methoxybenzyl)quinazolin-4(3H)-one; 4-((2-((4-Amino-3-(4-hydroxyphenyl)-1H-pyrazolo[3,4-d]pyrimidin-1-yl)methyl)-5-ethynyl-4-oxoquinazolin-3 (4H)-yl)methyl) benzonitrile; 2-((4-Amino-3-(4-hydroxyphenyl)-1H-pyrazolo[3,4-d]pyrimidin-1-yl)methyl)-5-ethynyl-3-(2-fluoro-4-methoxybenzyl) quinazolin-4(3H)-one; 1-(3-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)prop-2-ynyl)urea; 2-((4-Amino-3-(3-hydroxyphenyl)-1H-pyrazolo[3,4-d]pyrimidin-1-yl)methyl)-3-(2-fluorobenzyl)-5-(3-(2-(2-methoxyethoxy)ethoxy)prop-1-ynyl)quinazolin-4(3H)-one; 2-((4-Amino-3-(4-fluoro-3-hydroxyphenyl)-1H-pyrazolo[3,4-d]pyrimidin-1-yl) methyl)-3-(2-chlorobenzyl)-5-ethynyl-quinazolin-4(3H)-one; 2-((4-Amino-3-(4-hydroxyphenyl)-1H-pyrazolo[3,4-d]pyrimidin-1-yl)methyl)-3-(2-chlorobenzyl)-5-(3-phenoxyprop-1-ynyl)quinazolin-4(3H)-one; 2-((4-Amino-3-(4-hydroxyphenyl)-1H-pyrazolo[3,4-c]pyrimidin-1-yl)methyl)-3-(2-fluorobenzyl)-5-(6-morpholino-6-oxohex-1-yn-1-yl)quinazolin-4(3H)-one; 6-(21(4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N-(2-methoxyethyl)hex-5-ynamide; 2-((4-Amino-3-(3-hydroxyphenyl)-1H-pyrazolo[3,4-d]pyrimidin-1-yl)methyl)-3-(2-chlorobenzyl)-5-(7-morpholino-7-oxohept-1-yn-1-yl)quinazolin-4(3H)-one; 2-((4-Amino-3-(3-hydroxyphenyl)-1H-pyrazolo[3,4-d]pyrimidin-1-yl)methyl)-3-(2-chlorobenzyl)-5-(5-morpholino-5-oxopent-1-yn-1-yl)quinazolin-4(3H)-one; 2-((4-Amino-3-(3-hydroxyphenyl)-1H-pyrazolo[3,4-d]pyrimidin-1-yl)methyl)-3-((5-methylpyrazin-2-yl)methyl)-5-(6-morpholino-6-oxohex-1-yn-1-yl)quinazolin-4(3H)-one; 2-((4-Amino-3-(4-hydroxyphenyl)-1H-pyrazolo[3,4-d]pyrimidin-1-yl)methyl)-3-(2-chlorobenzyl)-5-(6-oxo-6-(piperidin-1-yl)hex-1-yn-1-yl)quinazolin-4(3H)-one; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-diethylhex-5-ynamide; 7-(2-((4-Amino-3-(3-hydroxyphenyl)-1H-pyrazolo[3,4-d]pyrimidin-1-yl)methyl)-3-(2-chloro-benzyl)-4-oxo-3,4-dihydroquinazolin-5-yl)hept-6-ynoic acid; 2-Acetamido-N-(3-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)prop-2-yn-1-yl)acetamide; 2-((4-Amino-3-(4-hydroxyphenyl)-1H-pyrazolo[3,4-d]pyrimidin-1-yl)methyl)-3-(3-methoxy-5-(trifluoromethyl) benzyl)-5-

(6-morpholino-6-oxohex-1-yn-1-yl)quinazolin-4(3H)-one; 2-((4-Amino-3-(4-hydroxyphenyl)-1H-pyrazolo[3,4-d]pyrimidin-1-yl)methyl)-3-(2-methoxy phenethyl)-5-(6-morpholino-6-oxohex-1-yn-1-yl)quinazolin-4(3H)-one; 2-((4-Amino-3-(4-hydroxyphenyl)-1H-pyrazolo[3,4-d]pyrimidin-1-yl)methyl)-3-(benzo[b]thiophen-2-ylmethyl)-5-(6-morpholino-6-oxohex-1-yn-1-yl)quinazolin-4(3H)-one; 2-((4-Amino-3-(4-hydroxyphenyl)-1H-pyrazolo[3,4-d]pyrimidin-1-yl)methyl)-3-(2-fluoro-3-methoxybenzyl)-5-(6-morpholino-6-oxohex-1-yn-1-yl)quinazolin-4(3H)-one; Methyl 3-((2-((4-amino-3-(3-hydroxyphenyl)-1H-pyrazolo[3,4-d]pyrimidin-1-yl)methyl)-5-(6-morpholino-6-oxohex-1-yn-1-yl)-4-oxoquinazolin-3(4H)-yl)methyl)benzoate; 2-((4-Amino-3-(3-hydroxyphenyl)-1H-pyrazolo[3,4-d]pyrimidin-1-yl)methyl)-3-((1-methyl-1H-pyrazol-4-yl)methyl)-5-(6-morpholino-6-oxohex-1-yn-1-yl) quinazolin-4(3H)-one; 2-((4-Amino-3-(3-hydroxyphenyl)-1H-pyrazolo[3,4-c]pyrimidin-1-yl)methyl)-3-(benzofuran-5-ylmethyl)-5-(6-morpholino-6-oxohex-1-yn-1-yl)quinazolin-4(3H)-one; 2-((4-Amino-3-(3-hydroxyphenyl)-1H-pyrazolo[3,4-d]pyrimidin-1-yl)methyl)-3-((2-methylthiazol-4-yl)methyl)-5-(6-morpholino-6-oxohex-1-yn-1-yl)quinazolin-4(3H)-one; 2-((4-Amino-3-(3-hydroxyphenyl)-1H-pyrazolo[3,4-d]pyrimidin-1-yl)methyl)-3-(2-chlorobenzyl)-5-(6-(4-methylpiperazin-1-yl)-6-oxohex-1-yn-1-yl)quinazolin-4(3H)-one; 2-((4-Amino-3-(3-hydroxyphenyl)-1H-pyrazolo[3,4-d]pyrimidin-1-yl)methyl)-3-(2-chlorobenzyl)-5-(6-(4-morpholinopiperidin-1-yl)-6-oxohex-1-yn-1-yl)quinazolin-4(3H)-one; 5-(6-(4-Acetylpiperazin-1-yl)-6-oxohex-1-yn-1-yl)-2-((4-amino-3-(4-hydroxyphenyl)-1H-pyrazolo[3,4-d]pyrimidin-1-yl)methyl)-3-(2-chlorobenzyl)quinazolin-4(3H)-one; N-(4-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)but-3-yn-1-yl)morpholine-4-carboxamide; 5-(6-(4-Acetyl-piperazin-1-yl)-6-oxohex-1-yn-1-yl)-2-((4-amino-3-(4-hydroxyphenyl)-1H-pyrazolo[3,4-d]pyrimidin-1-yl)methyl)-3-(2-chlorobenzyl)quinazolin-4(3H)-one; N-(4-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)but-3-yn-1-yl)morpholine-4-carboxamide; 2-((4-Amino-3-(4-hydroxy-phenyl)-1H-pyrazolo[3,4-d]pyrimidin-1-yl)methyl)-5-(5-(bis(2-methoxyethyl) amino)pent-1-ynyl)-3-(2-chlorobenzyl)quinazolin-4(3H)-one; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-cyclopentylhex-5-ynamide; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-(tetrahydro-2H-pyran-4-yl)hex-5-ynamide; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-(2-morpholinoethyl)hex-5-ynamide; 2-((4-Amino-3-(4-hydroxy phenyl)-1H-pyrazolo[3,4-d]pyrimidin-1-yl)methyl)-3-(2-chlorobenzyl)-5-(6-(4-(2-methoxyethyl)piperazin-1-yl)-6-oxohex-1-ynyl)quinazolin-4(3H)-one; 6-(2-((4-Amino-3-(4-hydroxyphenyl)-1H-pyrazolo[3,4-a]pyrimidin-1-yl)methyl)-3-(2-chlorobenzyl)-4-oxo-3,4-dihydroquinazolin-5-yl)-N-(2-(dimethylamino)ethyl)hex-5-ynamide; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-(pyridin-4-yl)hex-5-ynamide; 6-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N-(pyridin-4-yl)hex-5-ynamide; 2-((4-Amino-3-(4-hydroxyphenyl)-1H-pyrazolo[3,4-d]pyrimidin-1-yl)methyl)-3-(2-chlorobenzyl)-5-(6-(4-(dimethylamino)piperidin-1-yl)-6-oxohex-1-ynyl)quinazolin-4(3H)-one; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide; 6-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-(2-(4-methylpiperazin-1-yl)ethyl)hex-5-ynamide; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-methyl-N-(2-(4-methylpiperazin-1-yl)ethyl)hex-5-ynamide; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-isopropylhex-5-ynamide; 6-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N-isopropylhex-5-ynamide; 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-dimethylhex-5-ynamide; 2-((4-Amino-3-(4-hydroxyphenyl)-1H-pyrazolo[3,4-d]pyrimidin-1-yl)methyl)-3-(2-chlorobenzyl)-5-(6-oxo-6-(pyrrolidin-1-yl)hex-1-yn-1-yl)quinazolin-4(3H)-one; 6-(2-((4-Amino-3-(4-hydroxyphenyl)-1H-pyrazolo[3,4-c]pyrimidin-1-yl)methyl)-3-(2-chlorobenzyl)-4-oxo-3,4-dihydroquinazolin-5-yl)-N-(pyrrolidin-3-yl)hex-5-ynamide; 21(4-Amino-3-(4-hydroxyphenyl)-1H-pyrazolo[3,4-d]pyrimidin-1-yl)methyl)-3-(2-chlorobenzyl)-5-(6-(3-(dimethylamino)pyrrolidin-1-yl)-6-oxohex-1-ynyl)quinazolin-4(3H)-one; 2-((4-Amino-3-(3-hydroxyphenyl)-1H-pyrazolo[3,4-d]pyrimidin-1-yl)methyl)-3-(2-chlorobenzyl)-5-(6-(3-(dimethylamino)pyrrolidin-1-yl)-6-oxohex-1-ynyl)quinazolin-4(3H)-one; 2-((4-Amino-3-(4-hydroxyphenyl)-1H-pyrazolo[3,4-c]pyrimidin-1-yl)methyl)-3-(2-chlorobenzyl)-5-(6-(4-methyl-1,4-diazepan-1-yl)-6-oxohex-1-ynyl)quinazolin-4(3H)-one; 2-((4-Amino-3-(3-hydroxyphenyl)-1H-pyrazolo[3,4-d]pyrimidin-1-yl)methyl)-3-(2-chlorobenzyl)-5-(6-(4-methyl-1,4-diazepan-1-yl)-6-oxohex-1-ynyl)quinazolin-4(3H)-one, 2-((4-Amino-3-(4-hydroxy-3-methoxyphenyl)-1H-pyrazolo[3,4-d]pyrimidin-1-yl)methyl)-3-(2-chlorobenzyl)-5-(6-morpholino-6-oxohex-1-ynyl)quinazolin-4(3H)-one or a pharmaceutically acceptable salt thereof, including all stereoisomers, tautomers and isotopic derivatives thereof In one embodiment the combination employs a MEK inhibitor. Examples of MEK inhibitors include: A5703026, CI-1040 (PD184352), AZD6244 (Selumetinib), PD318088, PD0325901, AZD8330, PD98059, U0126-EtOH, BIX 02189 or BIX 02188.

In one embodiment the combination employs an AKT inhibitor. Examples of AKT inhibitors include: MK-2206 and AT7867.

In one embodiment the combination employs an aurora kinase inhibitor. Examples of aurora kinase inhibitors include: Aurora A Inhibitor I, VX-680, AZD1152-HQPA (Barasertib), SNS-314 Mesylate, PHA-680632, ZM-447439, CCT129202 and Hesperadin.

In one embodiment the combination employs a p38 inhibitor, for example as disclosed in WO2010/038086, such as N-[4-({4-[3-(3-tert-Butyl-1-p-tolyl-1H-pyrazol-5-yl)ureido]naphthalen-1-yloxy}methyl)pyridin-2-yl]-2-methoxyacetamide.

In one embodiment the combination employs a Bcl-2 inhibitor. Examples of Bcl-2 inhibitors include: obatoclax mesylate, ABT-737, ABT-263(navitoclax) and TW-37.

In one embodiment the combination employs an antimetabolite. Examples of an antimetabolite include: capecitabine (xeloda), fludarabine phosphate, fludarabine(fludara), decitabine, raltitrexed(tomudex), gemcitabine hydrochloride and cladribine.

In one embodiment the therapeutic agent is ganciclovir, which may assist in controlling immune responses and/or tumour vasculation.

In one embodiment one or more therapies employed in the method herein are metronomic, that is a continuous or frequent treatment with low doses of anticancer drugs, often given concomitant with other methods of therapy.

Subgroup B oncolytic adenoviruses, in particular Ad11 and those derived therefrom such as ColoAd1 may be particularly synergistic with chemotherapeutics because they seem to have a mechanism of action that is largely independent of apoptosis, killing cancer cells by a predominantly necrolytic mechanism. Moreover, the immunosuppression that occurs during chemotherapy may allow the oncolytic virus to function with greater efficiency.

In one embodiment the chemotherapeutic agent is administered parenterally.

In one embodiment the chemotherapeutic agent is administered separately to the virus, either temporally or by an alternate method of administration or both. Treatment can be concurrent or sequential.

In one embodiment the cancer treatment is a targeted agent, for example a monoclonal antibody such as bevacizumab, cetuximab or panitumumab or antibody conjugate, such as an antibody drug conjugate, in particular of the type where the antibody or binding fragment is linked to a toxin.

In one embodiment the cancer treatment is an immunotherapeutic agent, for example ipilimumab or other anti-CTLA4, anti-PD-1, anti-PD-L1, or other checkpoint inhibitors, or a cytokine or a cytokine analogue.

Checkpoint inhibitor as employed herein is intended to refer to agents that inhibit signalling from T-cell membrane proteins that act to inhibit or downregulate T-cell activation and function. In one embodiment the virus is administered in combination with the administration of radiotherapy.

Radiotherapy as employed herein is intended to refer to the medical use of ionising radiation.

Cancer cells are generally undifferentiated and stem cell-like; they reproduce more than most healthy differentiated cells, and have a diminished ability to repair sub-lethal damage. DNA damage is then passed on through cell division; damage to the cancer cells' DNA accumulates, causing them to die or reproduce more slowly.

In one embodiment the radiotherapy is administered concurrently.

In one embodiment the radiotherapy is administered sequentially.

In one embodiment the virus is administered in combination with therapy complimentary to the cancer therapy, for example a treatment for cachexia, such as cancer cachexia, for example S-pindolol, S-mepindolol or S-bopindolol. Suitable doses may be in the range of 2.5 mg to 100 mg, such as 2.5 mg to 50 mg per day provided a single dose or multiple doses given as multiple doses administered during the day.

In one embodiment the virus is administered in combination with the administration of one or more prophylactic agents, for example selected from an antipyretic, an antihistamine, an antiemetic, an antidiarrheal, steroid and an analgesic.

Antipyretics include aspirin and non-steroidal anti-inflammatories, for example ibuprofen, naproxen and ketoprofen.

Antihistamines include acrivastine, azalastine, brompheniramine, buclizine, bromodiphenhydramine, carbinoxamine, cetirizine, chlorpromazine, cyclizine, chlorpheniramine, chlorodiphenhydramine, clemastine, cyproheptadine, desloratadine, dexbrompheniramine, deschlorpheniramine, dexchlorpheniramine, dimenhydrinate, dimetindene, diphenhydramine, doxylamine, ebstine, embramine, fexofenadine, levocetirizine, loratadine, meclizine, mirtazapinem olopatadrine, pheninidamine, pheniramine, phenyltoloxamine, promethazine, pyrilamine, quetiapine, rupatadine, tripelennamine and triprolidine.

Antiemetics include dolasetron, granietron, ondansetron, tropisetron, palonoestron, mirtazapine, domperidone, olanzapine, droperidol, metoclopramide, alizapride, prochloperazine. In some instances antihistamines may be employed as antiemetics.

Antidiarrheals include methylcellulose, attapulgite, bismuth subsalicylate, atropine/diphenoxylate, loperamide and other opioids such as codeine and morphine.

Analgesics include non-steriodal anti-inflammatories, paracetamol, cox-2 inhibitors, opiates and morphinomimetics, such as morphine, codeine, oxycodone, hydrocodone, dihydromorphine, pethidine, buprenorphine, tramadol and the like.

In one embodiment viral treatment is employed in combination with a course of steroids.

Steroids include hydrocortisone, cortisone, prednisone, prednisolone, methylprednisolone, dexamethasone and the like.

Prophylactic as employed herein is intended to refer to preventive medicine or care, for example consisting of measures taken to prevent or ameliorate side effects during or following administration of the virus.

In one embodiment the prophylaxis is administered separately to the virus, either temporally or by an alternate method of administration or both. Treatment can be concurrent or sequential.

In one embodiment additional hydration is provided in combination with the administration of the virus, either concurrently or sequentially.

Additional hydration as employed herein means the patient is supplied with fluids beyond those included in the formulation. This may be any form of suitable liquid, for example, a saline or glucose infusion.

In one embodiment the virus therapy herein is administered in combination with an anti-inflammatory, for example a steroid or non-steroidal anti-inflammatory.

In one embodiment the virus therapy according to the present disclosure is administered in combination with an anti-pyretic.

In one embodiment the viral treatment is administered in combination with hydration therapy, for example intravenous administration of fluids, in particular isotonic saline or glucose.

In one embodiment the method is suitable for treating the patient as an outpatient.

Outpatient as employed herein is a patient who is not hospitalised during the treatment phase, but instead comes to a physician's office, clinic or day surgery for treatment.

In one embodiment there is provided a method of treating a patient with a pharmaceutical formulation described herein comprising ColoAd1 said method comprising the steps of intravenously administering to said patient: a dose on day 1 followed by, a dose on day 3, and a third dose on day 5.

In one embodiment there is provided a parenteral formulation of a replication capable oncolytic subgroup B adenovirus described herein, for use in treatment, such as a tumour and/or malignancy and/or cancer treatment by administering: a first dose of said formulation described herein, followed by one or more further therapeutic doses thereof wherein the first dose and further doses are administered within a period of 14 days, in particular as described supra.

In one embodiment, there is provided the use of multiple cycles of treatment with a replication capable oncolytic subgroup B adenovirus. A treatment cycle is to be interpreted herein as a series of viral doses administered to a patient over a relatively short period of time after which the patient's response will be assessed. Treatment cycles can be repeated multiple times provided the risk benefit is determined to be in the patient's best interests.

In one embodiment, there is provided a method to assess the suitability of repeated cycles of treatment with a replication capable oncolytic subgroup B adenovirus by determining the level of the specific antiviral titre and comparing it to the pre-treatment titre, such that a titre below a certain percentage of the pre-treatment titre will indicate a positive risk benefit profile for retreatment.

In one embodiment there is provided use of parenteral formulation of a replication capable oncolytic subgroup B adenovirus in the manufacture of a medicament for treatment of a tumour and/or malignancy and/or cancer treatment by employing a treatment regimen herein.

In one embodiment the formulation is employed in the treatment or prophylaxis of metastasis.

In one embodiment, there is provided a formulation presented as a sterile prefilled and packaged syringe of appropriate dose and volume in order to circumvent the need for complex and expensive dose preparation under sterile conditions and using appropriate air handling such as extraction hoods prior to administration to the patient.

In the context of this specification "comprising" is to be interpreted as "including".

Aspects of the invention comprising certain elements are also intended to extend to alternative embodiments "consisting" or "consisting essentially" of the relevant elements.

Any positive embodiment or combination thereof described herein may be the basis of a negative exclusion i.e. a disclaimer.

EXAMPLES

Preclinical Potency and Selectivity

Table 2 shows the $IC_{50}$ of ColoAd1 on a variety of epithelial cell lines.

| Cell Name | Cell Type | IC50 |
|---|---|---|
| HT-29[1] | Colorectal cancer | 0.06 |
| HT-29[2] | Colorectal cancer | 0.04 |
| DLD-1[1] | Colorectal cancer | 0.35 |
| LS1034[1] | Colorectal cancer | 0.21 |
| HCT116[1] | Colorectal cancer | 0.02 |
| LS174T[1] | Colorectal cancer | 0.57 |
| SW48[1] | Colorectal cancer | 0.06 |
| SW403[1] | Colorectal cancer | 1 |
| HepG2[2] | Hepatoma | 0.05 |
| PC-3[1] | Prostate cancer | 0.23 |
| DU145[1] | Prostate cancer | 5 |
| Panc-1[1] | Pancreatic cancer | 12 |
| MDA231[1] | Breast cancer | 0.84 |
| OVCAR-3[1] | Ovarian cancer | 3 |
| A549[2] | Lung cancer | 2 |
| HMEC[1] | Capillary endothelial | 575 |
| HUVE[1] | Umbilical endothelial | 50 |
| HUVE[2] | Umbilical endothelial | 60 |
| Hepatocytes[2] | Normal liver cells | 1050 |
| W138[2] | Fibroblast | 350 |

The $IC_{50}$ of ColoAd1 on a range of epithelial derived cancer and normal cells. The number of ColoAd1 particles required to kill 50% of cell ($IC_{50}$) was determined in vitro using a standard 6 day MTS assay.
[1]Results performed by Schering AG and published in Kuhn et al., 2008.
[2]Repeat and additional studies performed by the University of Oxford (unpublished).

Table 3 shows the $IC_{50}$ of ColoAd1 on a variety of non-epithelial cell lines.

| Cell name | Cell type | IC50 |
|---|---|---|
| Colo320DM[1] | neuroendocrine | 105 |
| 501[2] | melanoma | 430 |
| IG37[2] | melanoma | >500 |
| IG39[2] | melanoma | 470 |
| U87MG[2] | Glioblastoma | >1000 |
| BBA[2] | Glioblastoma | >1000 |
| BBB[2] | Glioblastoma | >1000 |
| K562[2] | Leukaemia | >1000 |

The $IC_{50}$ of ColoAd1 on a range of non-epithelial derived cancers. The number of particles required to kill 50% of cell ($IC_{50}$) was determined in vitro using a standard 5 day MTS assay.
[1]Results performed by Schering AG and published in Kuhn et al., 2008.
[2]Repeat and additional studies performed by the University of Oxford (unpublished).

Table 4 shows ColoAd1 replication in a variety of normal non-cancer human cell lines.

| Human Cell Types | Genomes (cells) | % of control | Genomes (supernatant) | % of control | Successful Re-infection of HT29 Cells |
|---|---|---|---|---|---|
| HT29 (+ve control) | 3.18E+08 | 100 | 4.29E+06 | 100 | YES |
| hepatocytes | 6.83E+03 | 0.0021 | 2.47E+02 | 0.01 | No |
| glomerular endothelial cells | 4.78E+02 | 0.0002 | 1.22E+03 | 0.03 | No |
| dermal microvascular cells | 1.03E+03 | 0.0003 | 1.45E+03 | 0.03 | No |
| cardiac microvascular cells | 5.36E+02 | 0.0002 | 1.29E+03 | 0.03 | No |
| corneal epithelial | 2.51E+06 | 0.7889 | 7.06E+04 | 1.65 | No |
| bronchial epithelial | 5.48E+05 | 0.1722 | 2.88E+04 | 0.67 | No |
| renal cortical epithelial | 3.68E+04 | 0.0116 | 3.67E+03 | 0.09 | No |
| mesangial cells | 1.18E+03 | 0.0004 | 9.71E+02 | 0.02 | No |
| Intestinal myofibroblasts | 9.50E+02 | 0.0003 | 1.49E+03 | 0.03 | No |
| ovarian epithelial | 2.38E+06 | 0.7479 | 9.99E+04 | 2.33 | No |
| astrocytes | 7.00E+02 | 0.0002 | 9.26E+02 | 0.02 | No |

| Human Cell Types | Genomes (cells) | % of control | Genomes (supernatant) | % of control | Successful Re-infection of HT29 Cells |
|---|---|---|---|---|---|
| aortic smooth muscle Cells | 8.65E+02 | 0.0003 | 9.42E+02 | 0.02 | No |
| cardiac myocytes | 1.28E+03 | 0.0004 | 7.99E+02 | 0.02 | No |
| renal proximal | 8.48E+05 | 0.2666 | 4.46E+03 | 0.10 | No |
| CD34+ | 1.59E+03 | 0.0005 | 2.84E+03 | 0.07 | No |
| PBMC | 1.25E+03 | 0.0004 | 1.02E+03 | 0.02 | No |

Human cells growing in monolayers in vitro were exposed to ColoAd1 for 72 hours. The total number of ColoAd1 genome copies was then determined by qPCR. The data are presented as total genome copies and as a % relative to a carcinoma cell positive control (HT29). The ColoAd1 materials derived from these normal human cells were then tested for viability on HT29 carcinoma cells. In all cases ColoAd1 material so recovered could not be shown to replicate in HT29 cells.

Pre-Clinical Circulation Kinetics

ColoAd1 circulation kinetics were obtained in CD-1 mice. Mice (3 per group) were administered virus particles via the tail vein and circulating genomes in whole blood samples were determined by quantitative PCR (qPCR). ColoAd1 half-life in this model is dose-dependent. At the lower input doses ($1 \times 10^9$-$2 \times 10^{10}$ on multiple dosing days), the mean alpha half-life is 1.8+/−0.5 minutes, consistent with values previously reported for other adenoviruses (Green 2004). At higher doses (over $2 \times 10^{11}$), saturation of clearance appears to occur, giving rise to longer circulation levels (mean alpha half-life 7.8+/−2 minutes). Saturation in the ColoAd1 study described here is reflected via multiple pharmacokinetic parameters Table 5 demonstrates significant increases in Area Under the Curve (AUC), half-life and percentage of particles retained at the 30 min time-point when ColoAd1 doses were administered over $2 \times 10^{11}$. It was noted in particular that the optimal kinetics (AUC, percentage retained particles at 30 min and mean alpha t½) were all achieved when three equal high doses were administered as opposed to a low priming dose followed by higher doses. From this data, given that blood circulation times are significantly longer in humans than in mice, it was anticipated that the half-life in humans would be considerably longer and that low priming doses were unlikely to be of value for a sub-group B adenovirus. In addition, in tumour bearing human patients, it was anticipated that replication of this virus in cancer cells, with subsequent release, would also result in further amplification of the virus at later time points. The clinical studies were planned accordingly.

TABLE 5

Circulation kinetics of ColoAd1 following multiple intra-venous injections in CD-1 mice (3 mice per group)

| Study | Dose | Mean Alpha t½ (minutes) | Mean AUC ml$^{-1}$ min$^{-1}$ | Mean % of input virus at 30 min |
|---|---|---|---|---|
| multi-dose study in CD1 mice $1 \times 10^9$ on day 1 then $1 \times 10^{10}$ on days 3 and 5 | $1 \times 10^9$ (d1) | 2.2 | $1.04 \times 10^9$ | 0.77 |
|  | $1 \times 10^{10}$ (d3) | 2.6 | $9.17 \times 10^9$ | 0.52 |
|  | $1 \times 10^{10}$ (d5) | 2.6 | $1.20 \times 10^{10}$ | 0.42 |
| multi-dose study in CD1 mice $1 \times 10^{10}$ on day 1 then $1 \times 10^{11}$ on days 3 and 5 | $1 \times 10^{10}$ (d1) | 1.2 | $1.06 \times 10^{10}$ | 0.10 |
|  | $1 \times 10^{11}$ (d3) | 1.3 | $9.20 \times 10^{10}$ | 0.75 |
|  | $1 \times 10^{11}$ (d5) | 1.2 | $1.06 \times 10^{11}$ | 0.97 |
| multi-dose study in CD1 mice $2 \times 10^{10}$ on day 1 then $2 \times 10^{11}$ on days 3 and 5 | $2 \times 10^{10}$ (d1) | 1.7 | $1.71 \times 10^{10}$ | 0.29 |
|  | $2 \times 10^{11}$ (d3) | 3.7 | $3.00 \times 10^{11}$ | 4.52 |
|  | $2 \times 10^{11}$ (d5) | 4.0 | $6.31 \times 10^{11}$ | 13.62 |
| multi-dose in CD1 mice all three doses at $2 \times 10^{11}$ on days 1, 3 and 5 | $2 \times 10^{11}$ (d1) | 6.5 | $1.09 \times 10^{12}$ | 27.43 |
|  | $2 \times 10^{11}$ (d3) | 10.1 | $1.21 \times 10^{12}$ | 28.67 |
|  | $2 \times 10^{11}$ (d5) | 6.8 | $7.875 \times 10^{11}$ | 10.48 |

Pre-Clinical Interaction Studies

Virus particles can interact with components of human blood including antibodies, complement and blood cells leading to rapid neutralisation (Lyons 2005, Carlisle 2009). These events are species-specific and cannot be modelled effectively in animals.

To evaluate neutralisation in human blood, ColoAd1 may be incubated in freshly isolated whole human blood from individuals before being applied to permissive cells (HT29 colorectal tumour cells). A range of virus concentrations can be chosen to cover the target clinical dose range ($2 \times 10^6$ to $2 \times 10^9$ particles per ml of human blood, and assuming a range of human blood volumes). Residual virus potency can be determined by cytotoxicity and compared to virus infection in the absence of incubation in human blood (media alone) and potency levels within a concentration in the range $2 \times 10^6$ to $2 \times 10^9$ viral particles per ml is desirable.

The data in FIG. 1 further demonstrate that ColoAd1 was only marginally affected by human blood. Fresh human blood was collected from 9 subjects (A-I) using lithium heparin tubes. ColoAd1 virus particles were added to the blood samples at 10 fold dilutions from $2 \times 10^9$ VP/mL, which reflects a potential equivalent human dose of $1 \times 10^{13}$ assuming that the dose is fully diluted in the total blood volume (assumed to be 5 L of blood). After 20 minutes incubation at 37° C., the virus/blood mixture was added to A549 tumour cells growing in a 96-well plate. The proportion of viable A549 cells remaining was then determined after 5 days and plotted as a percentage. The $IC_{50}$ occurs at a level of approximately equivalent to a viral blood concentration of $2 \times 10^6$ VP/mL. This level of virus was thus determined as a minimum target level to achieve in the human clinical studies Several in vitro studies were also conducted of the interaction of ColoAd1 with human blood cells. Fresh blood was obtained from 4 individuals, and erythrocytes, platelets and leukocytes were washed and re-suspended in PBS at physiological cell concentrations ($5 \times 10^9$, $2 \times 10^8$ and $6 \times 10^6$ per mL, respectively) for use in individual experiments. qPCR analysis revealed that over 80% (82%±8%) of the ColoAd1 was associated with human blood cells, primarily to erythrocytes and leukocytes. There was no significant difference in the fraction of ColoAd1 bound to blood cells after a 5 or 30 minutes of incubation. Ad5 showed comparatively higher levels of binding to human blood cells (95.5±1.2%) than ColoAd1. Based on relative fluorescence, pre-incubation of ColoAd1-gfp with human blood cells for 30 minutes significantly inhibited (>90%) the infection of SW480 tumour cells, which express only low levels of CD46, the cellular receptor for ColoAd1. Infection of HT29 cells, which express higher levels of CD46, was inhibited to a much lesser extent (~41%), probably because of the higher level of expression of the ColoAd1 receptor on these tumour cells. Finally, the infection of leukocytes, which may express high levels of CD46 and thus serve as a "sink" for ColoAd1, was assessed using ColoAd1-gfp to determine the extent of transgene expression. After 24 hours no evidence of transgene expression was observed in leukocytes. In contrast, previous studies have shown that Ad5 is able to efficiently infect monocytes in vitro under the same conditions. In summary, these studies suggest that the interaction of ColoAd1 with cellular blood components is limited and significantly different to that of Ad5. Again, the clinical studies were designed taking this into account.

Pre-Clinical Biodistribution of ColoAd1

Figure 2:
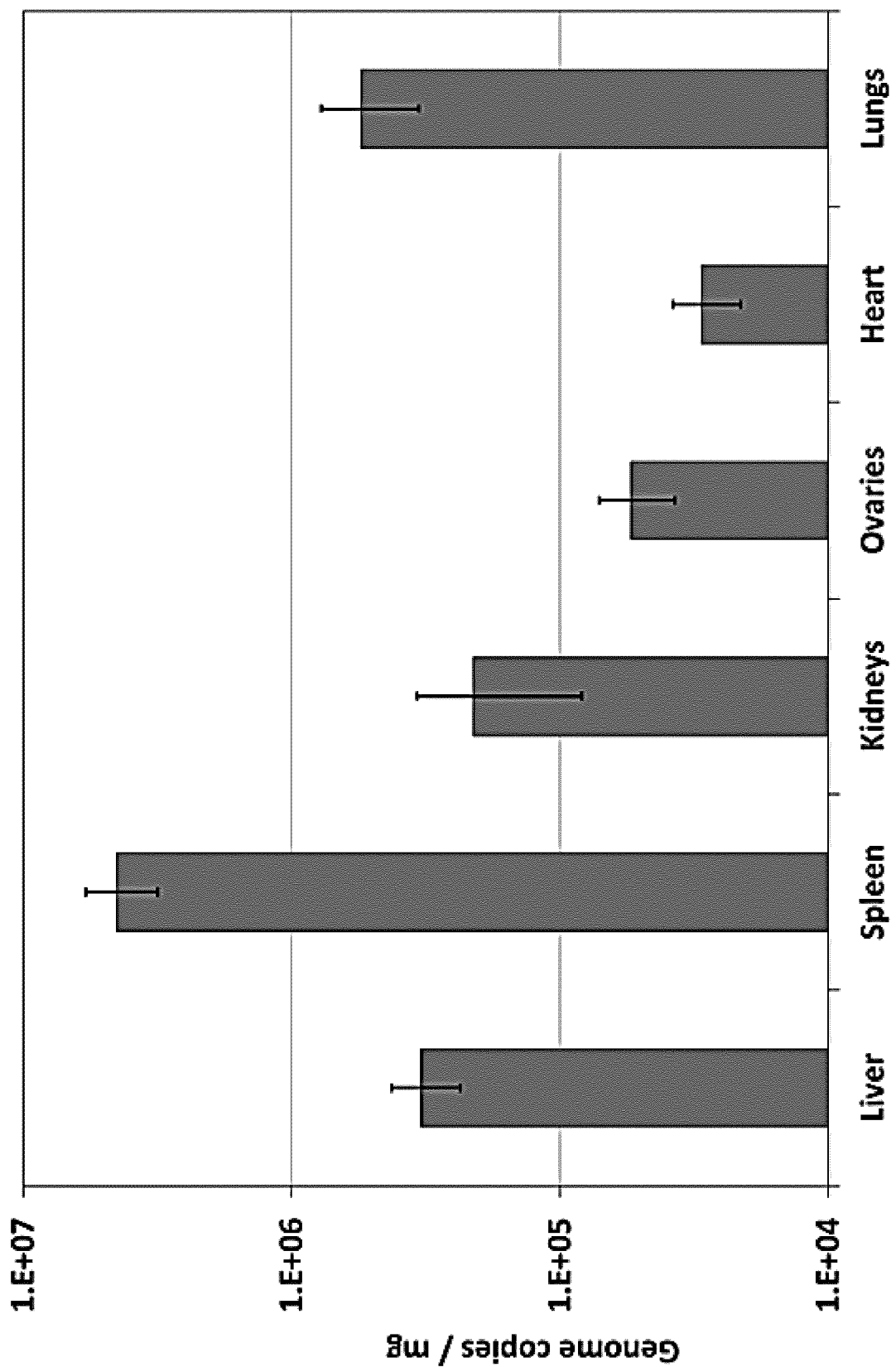
FIG. 2 Biodistribution of 1e11 ($1\times10^{11}$) particles of ColoAd1 in normal BalbC mice 24 hours post injection.
Figure 3:
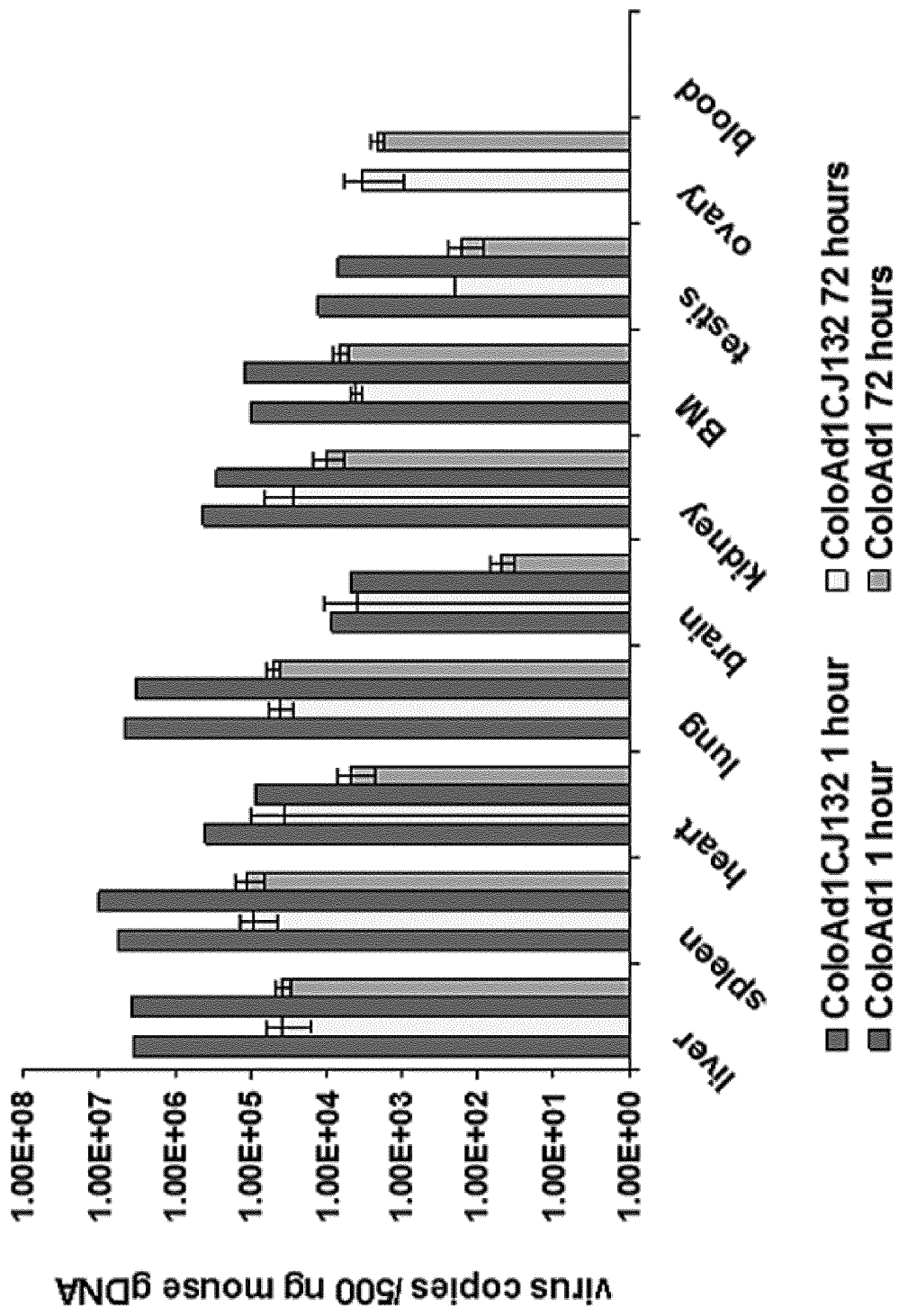
FIG. 3 Biodistribution of ColoAd1 and ColoAd10132 in CD46 transgenic mice at 1 hr and 72 hrs post-injection.

Biodistribution and clearance of ColoAd1 has been determined in normal mice and transgenic mice expressing the primary virus receptor CD46 (a receptor for group B adenoviruses that is not expressed in normal mice). Following tail vein administration of $1 \times 10^{11}$ virus particles in normal mice, virus particles were predominantly found in the liver, spleen and lungs after 24 hrs. (FIG. 2) indicates viral copies per mg and so these larger organs represent the predominant site of total viral distribution on a percentage basis). Similar distribution to the same target organs was observed in CD46 transgenic mice (FIG. 3), showing that the CD46 receptor is not a significant determinant of distribution. The distribution of a non-replicating mutant (ColoAd1CJ132) was identical to that of ColoAd1 indicating replication was not responsible for any of this distribution effect. However, in tumour bearing human patients, it was anticipated that replication of this virus in cancer cells, with subsequent release, would also result in further amplification of the virus at later time points and so the clinical studies were planned accordingly.

Pre-Clinical Viral Clearance

Figure 4:
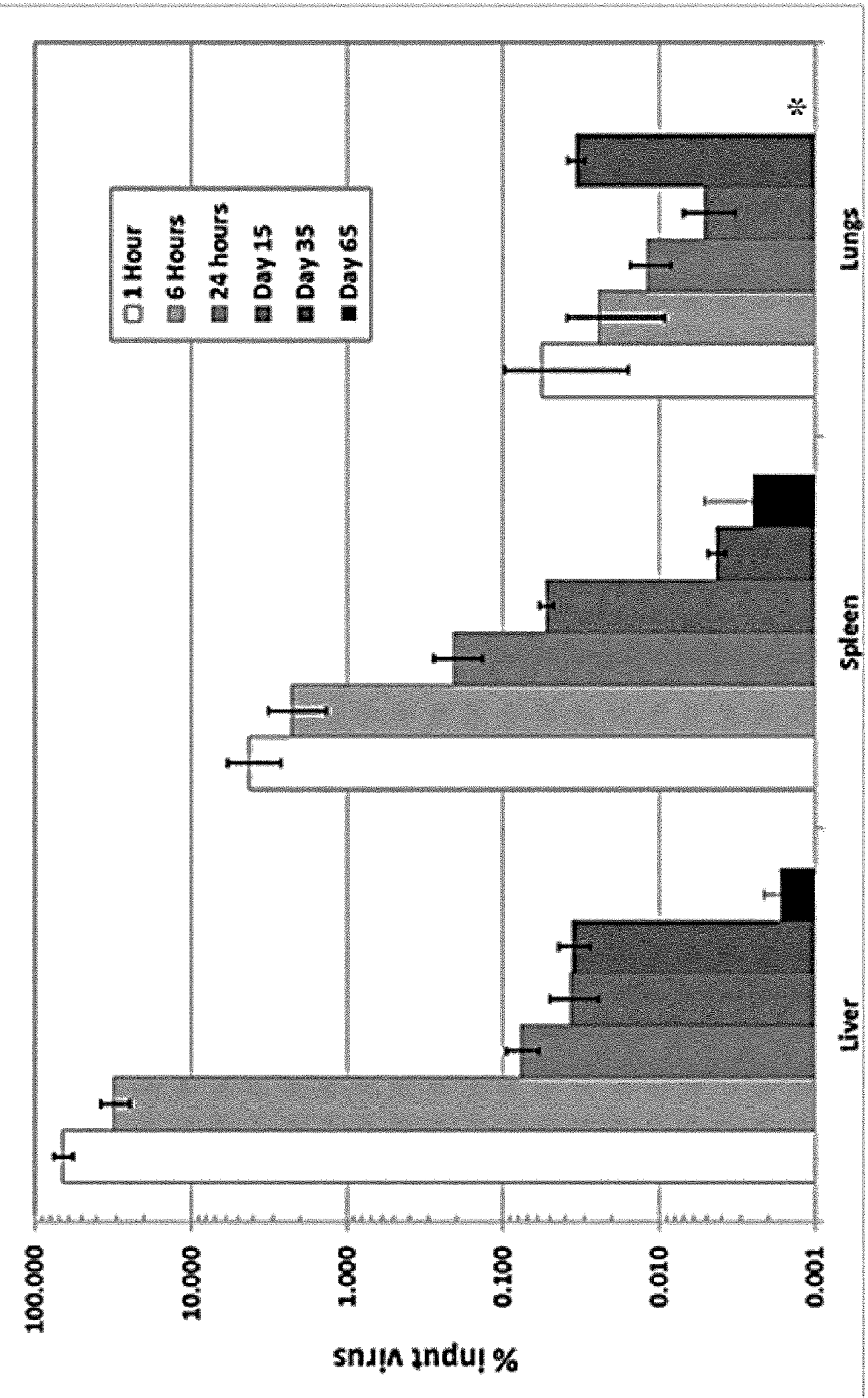
FIG. 4 Clearance kinetics of ColoAd1 from primary organs liver, spleen and lungs in CD46-expressing mice followed for 65 days.

To identify the time to complete virus clearance, a long-term particle clearance study was carried out in normal Balbc mice. The dominant organs for virus distribution: liver, spleen and lungs, were chosen for analysis. Here, the total virus particles per organ are recorded as a percentage of the input dose at each time point such that the results are not normalised to organ weight. At 1 hour the majority of the input virus has already been sequestered in the Liver, with less than 5% in the spleen and less than 0.1% in the lungs. At 24 hours post injection virus particles have rapidly been cleared from these organs with less than 1% of the input virus genomes remaining. Beyond day 65 post-injection, no significant levels of virus were detectable in any tissues and levels were not significantly above background. No virus particles could be recovered for any tissues at day 65 post-administration. The kinetics of viral clearance (data presented as % of input dose per organ) are summarised in FIG. 4.

CD46 transgenic mice were administered ColoAd1 on a single occasion at a dose of $1 \times 10^{10}$ vp/mouse by tail vein. n=3 animals per time-point. Genome copies (measured by qPCR) are presented as a percentage of the input dose of genome copies.

Pre-Clinical Immunogenicity

Figure 5:
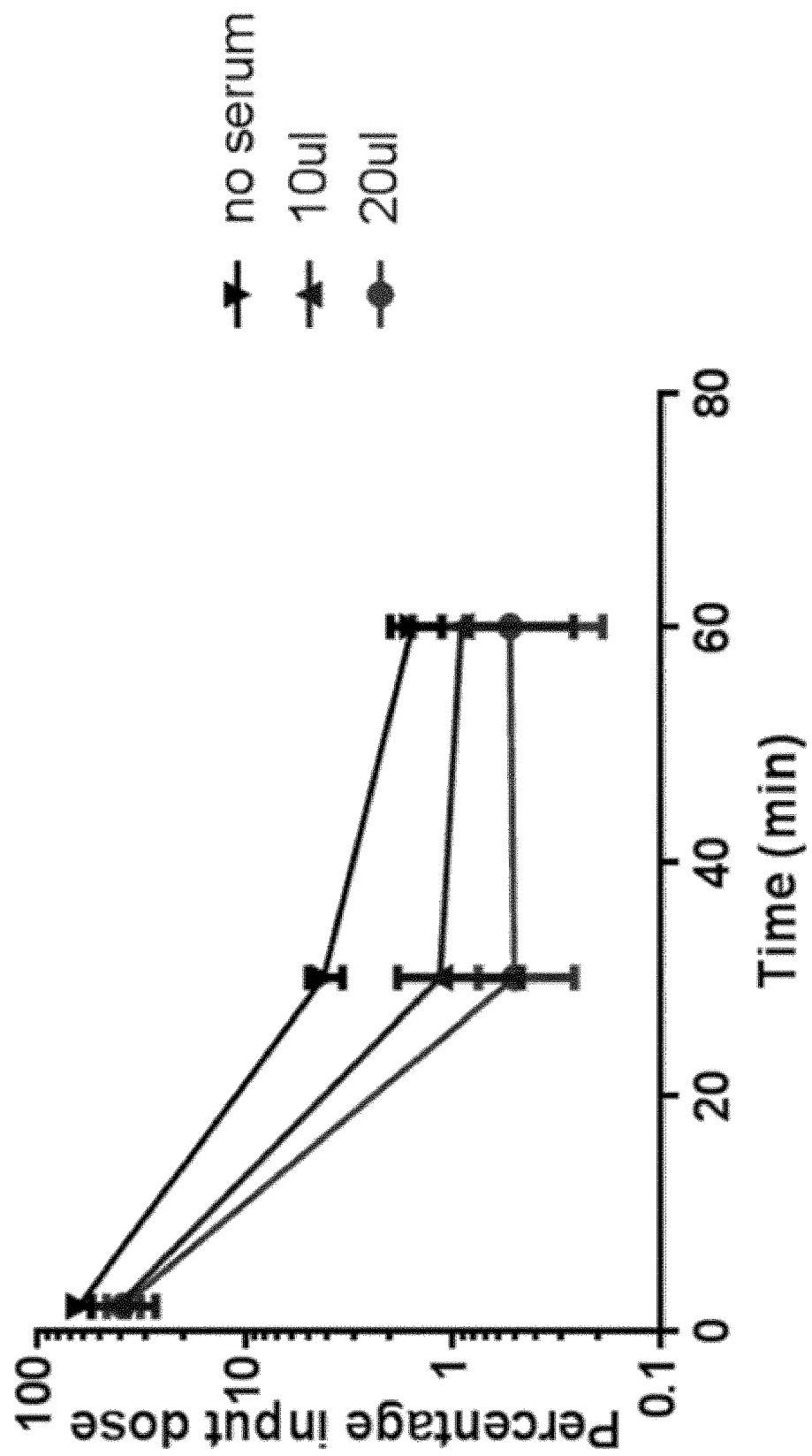
FIG. 5 Kinetics of ColoAd1 in mice either with or without co-administration of neutralising serum.

It is possible that the development of a specific anti-viral immune response may significantly impact the circulation kinetics. To examine this possibility, a group of mice were administered ColoAd1 repeatedly over several months in order to produce a pool of hyper-immune serum. A second group of mice were then passively immunised against ColoAd1 using the hyper-immune serum administered by i.v injection of 10 or 20 ul. These mice were then rested for 10 minutes before being administered $5 \times 10^{10}$ ColoAd1 i.v. Blood was collected from each mouse at 2, 10 and 30 minutes post-injection of ColoAd1 then analysed by qPCR. The results are shown in FIG. 5 and show that an immune response to ColoAd1 will have a significant impact upon the kinetics and delivery of ColoAd1, thus demonstrating the importance of administering doses before such a response occurs.

Pre-Clinical Safety and Toxicity

Several safety and toxicity studies have been conducted with ColoAd1, including pilot studies in CD-1 and Balb/c mice, CD46 transgenic mice. In a final toxicity study in male and female CD-1 mice, ColoAd1 was administered as three doses given over a 5-day period (on Days 1, 3 and 5) to model the intended clinical dosing regimen. Male and female CD-1 mice received intravenous bolus injections (dose volume=100 μL) of ColoAd1 or the formulation buffer as shown in Table 6, which shows the final study design after the unscheduled deaths of two Group 4 males on Day 1 led to the lowering of the dose in that particular group.

TABLE 6

Toxicity Study Design

| Group No. | Main Study No. of Animals | | Recovery Group No. of Animals | | Satellite Group No. of Animals | | Test Item | Total Dosage (vp/animal) |
|---|---|---|---|---|---|---|---|---|
| | Males | Females | Males | Females | Males | Females | | |
| 1 | 8 | 8 | 8 | 8 | 9 | 9 | Vehicle | — |
| 2 | 8 | 8 | 8 | 8 | 9 | 9 | ColoAd1 | $6.6 \times 10^9$ |
| 3 | 8 | 8 | 8 | 8 | 9 | 9 | ColoAd1 | $6.6 \times 10^{10}$ |
| 4 | $2^a$ | — | $4^b$ | — | $2^b$ | — | ColoAd1 | $2.2 \times 10^{11}$ |
| | $6^c$ | — | $4^c$ | — | $7^c$ | — | ColoAd1 | $3.59 \times 10^{11}$ |
| | — | — | — | — | $3^d$ | — | ColoAd1 | $2.09 \times 10^{11}$ |
| | — | $8^e$ | — | $8^e$ | $9^e$ | $9^e$ | ColoAd1 | $2.09 \times 10^{11}$ |

$^a$found dead on Day 1 after treatment; received a single dose of ColoAd1 on Day 1 at $2.2 \times 10^{11}$ vp
$^b$deemed unsuitable for further dosing and euthanised on Day 2; received a single ColoAd1 dose on Day 1 at $2.2 \times 10^{11}$ vp
$^c$received a single dose of $2.2 \times 10^{11}$ vp ColoAd1 on Day 1, then subsequent doses of $6.96 \times 10^{10}$ vp on Days 3 and 5
$^d$additional males added for cytokine assessment received $6.96 \times 10^{10}$ vp on Days 1, 3 and 5
$^e$at the top dose all females and all satellite group males received $6.96 \times 10^{10}$ vp on Days 1, 3 and 5

A standard set of safety endpoints, including clinical signs, body weight, plasma cytokine levels, clinical pathology and gross and microscopic examinations were done periodically. A standard list of tissues and organs was collected at necropsy on Days 6 and 17.

No significant clinical signs were observed in males and females in Groups 1, 2 or 3 on any treatment day. Clinical signs of adverse effect were seen in Group 4 after the first dose on Day 1 at doses of both $2.2 \times 10^{11}$ and $6.96 \times 10^{10}$ vp/animal, but—with the exception of one Group 4 male on Day 3—further adverse clinical signs were not seen. Dose-related body weight loss on Day 2 was seen in all ColoAd1-treated groups except for Group 2 males, though body weight was subsequently unaffected in any treatment group. Haematological and liver function changes, when recorded, occurred over a longer time course but had returned to normal range by the end of the recovery period. In summary, the most significant clinical signs were seen following the first dose, with subsequent doses being better tolerated.

Cytokine responses over time in this study are shown in FIG. 6. Elevations of the cytokine MCP-1 were most marked and seen in Groups 3 and 4 on Day 1 at 6 and 24 hours post-first treatment and 6 hours after treatment on Day 5. No consistent elevation in any other cytokine was seen in Group 2 animals. Smaller, but dose-related, increases in IL-6, IFNγ and TNFα were seen in Group 3 and 4 animals only, most commonly at low concentrations compared to MCP-1 and often in only some animals in each dose group, particularly in Group 3.

The cytokine pattern seen in this study is thus consistent with the clinical signs observed, showing that after the first dose, each subsequent dose is better tolerated, even though the doses are equal.

Clinical Studies

At the time of filing, two clinical studies are being conducted to examine the safety and efficacy of ColoAd1 when delivered intravenously to human subjects with metastatic cancer.

The Evolve study (ColoAd1-1001) is a phase I/II clinical study with the phase I dose escalation component conducted in patients with an epithelially derived metastatic tumour (of any origin) and who have no further treatment options. Patients in this phase I dose escalation part of the study have been dosed with three equal doses of intravenous ColoAd1 on days 1, 3 and 5 (48 hours apart). A slow intravenous infusion has been used, and in the early cohorts, each patient was infused with 30 ml of viral suspension over a 5 minute period (6 ml per minute). Initially each cohort of three patients was dosed at one log increments starting at $1 \times 10^{10}$ viral particles per dose until adverse events suggested dose limiting toxicity. Each patient also received a regimen of symptomatic prophylaxis, including supplemental fluids and a set regimen of anti-inflammatories (acetaminophen/paracetamol and ibuprofen). The safety and tolerability of this dosing regimen at each dose level was assessed using physical examinations (including blood pressure, pulse and temperature) and by eliciting all adverse events, as well as by assessing haematology, biochemistry and cytokine profile changes. Viral kinetics and excretion were assessed using regular blood, urine, stool and sputum samples. Efficacy was assessed by serial CT imaging according to objective criteria. Later stages of this study will go on to examine the safety and efficacy of the intravenous Maximum Tolerated Dose (MTD) of ColoAd1 in patients with metastatic colorectal cancer.

A second clinical study (ColoAd1-1002) is a phase 0 "window of opportunity" study to compare intravenous delivery with direct intra-tumoural delivery of ColoAd1 in patients with a newly diagnosed primary (non-metastatic) colorectal tumour. Patients in this study will be dosed pre-surgically with ColoAd1 and the resected tumours will then be examined post-surgically to examine the extent of viral delivery, replication and spread following the two different delivery and dosage regimens. The measures of safety and viral kinetics in this study are broadly similar to those of ColoAd1-1001.

The phase I dose escalation patients in study ColoAd1-1001 were dosed intravenously with ColoAd1 at dose levels up to and including $1 \times 10^{13}$ viral particles, in 7 patient cohorts (i.e. Cohorts 1 to 7) as shown in table 7 below.

TABLE 7

Dosage regimes for Cohorts 1 to 7 in the phase I dose escalation component of the ColoAd1-1001 clinical study.

| Dose cohort number | Total number of viral particles (VP) administered per dose | Dose regime (as repeated on days 1, 3 and 5) | | | | |
|---|---|---|---|---|---|---|
| | | Infusion Volume (ml) | Infusion duration (min) | Infusion rate | Rate of viral particle delivery (VP/minute) | Dose tolerability |
| 1 | 1e10 (1 × $10^{10}$) | 30 ml | 5 min | 6 ml/min | 2e9 VP/min | Well tolerated |
| 2 | 1e11 (1 × $10^{11}$) | 30 ml | 5 min | 6 ml/min | 2e10 VP/min | Well tolerated |
| 3 | 1e12 (1 × $10^{12}$) | 30 ml | 5 min | 6 ml/min | 2e11 VP/min | Well tolerated |
| 4 | 1e13 (1 × $10^{13}$) | 30 ml | 5 min | 6 ml/min | 2e12 VP/min | Not tolerated (dose limiting toxicity) |
| 5 | 3e12 (3 × $10^{12}$) | 30 ml | 5 min | 6 ml/min | 6e11 VP/min | Well tolerated |
| 6 | 3e12 (3 × $10^{12}$) | 30 ml | 20 min | 1.5 ml/min | 1.5e11 VP/min | Well tolerated |
| 7 | 6e12 (6 × $10^{12}$) | 30 ml | 40 min | 0.75 ml/min | 1.5e11 VP/min | Well tolerated |

The side effect profile of ColoAd1 in this study has included fever, flu like illness, transaminitis, thrombocytopenia, neutropenia, diarrhoea and vomiting. However, at a dose level of 1×$10^{13}$ viral particles infused over 5 minutes, the dose was not well tolerated. In particular, two patients suffered dose limiting toxicities (DLT) including a cytokine mediated acute lung injury at this dose and could not tolerate more than a single dose. One patient required steroids to treat this condition. Patients at this dose level also suffered chills, hypertension, pain, transaminitis, PPT prolongation, and D-dimer increases, although all resolved with time. As a result of these toxic effects at this poorly tolerated dose, the dose of ColoAd1 was reduced and then re-escalated using slower infusion rates. Using this strategy, doses of 3×$10^{12}$ VP over either 5 (cohort 5) or 20 minutes (cohort 6) and 6×$10^{12}$ VP infused over 40 minutes (cohort 7) were all shown to be well tolerated.

This safety data is preliminary at the time of writing, but is supportive of a very similar profile to that seen in mice. However, some patients continued to have fever and asthenia into the second week despite no ongoing dosing, a phenomenon that is consistent with on-going viral replication in the human tumours (a phenomenon that would not be seen in non-tumour bearing mice). The final maximum tolerated dose for humans is thus anticipated to be between 1×$10^{12}$ and 1×$10^{13}$ viral particles administered on days 1, 3 and 5 at an infusion rate of up to 6×$10^{11}$ VP/min and with each patient also receiving prophylactic anti-inflammatory medication and intravenous fluids as per the ColoAd1-1001 protocol. The final optimal dose regimen is now the subject of further confirmatory studies.

Table 8 summarises the key viral pharmacokinetic parameters as measured with qPCR for each patient in the phase I dose escalation component of the ColoAd1-1001 clinical study. These results were largely consistent with the preclinical data. In summary there was a dose dependent cMAX and AUC, and the average alpha half-life was approximately 18 minutes although there was an indication of possible saturation kinetics at the higher doses studied.

TABLE 8

ColoAd1 Pharmacokinetics for Cohorts 1 to 7

| Cohort | Patient number * | Dose (viral particles) | Infusion time (min) | α-half life (min) | EOI whole blood viral load (DNA copies/ml) | $C_{max}$ (DNA copies/ml) | AUC (DNA copies L/min) |
|---|---|---|---|---|---|---|---|
| 1 | 1 | 1 × $10^{10}$ | 5 | 28.22 | 1.75 × $10^6$ | 1.75 × $10^6$ | 8.08 × $10^{10}$ |
|   | 2 | 1 × $10^{10}$ | 5 | nd | 1.20 × $10^6$ | nd | nd |
|   | 3 | 1 × $10^{10}$ | 5 | 20.2 | 9.84 × $10^5$ | 9.86 × $10^5$ | 4.08 × $10^{10}$ |
| 2 | 4 | 1 × $10^{11}$ | 5 | 4.913 | 1.60 × $10^7$ | 1.60 × $10^7$ | 3.70 × $10^{11}$ |
|   | 5 | 1 × $10^{11}$ | 5 | 7.218 | 7.42 × $10^6$ | 7.41 × $10^6$ | 2.22 × $10^{11}$ |
|   | 6 | 1 × $10^{11}$ | 5 | 6.006 | 1.73 × $10^6$ | 2.67 × $10^6$ | 5.54 × $10^{10}$ |
| 3 | 7 | 1 × $10^{12}$ | 5 | 26.66 | 1.08 × $10^8$ | 1.20 × $10^8$ | 4.84 × $10^{12}$ |
|   | 8 | 1 × $10^{12}$ | 5 | 8.046 | 1.26 × $10^8$ | 1.26 × $10^8$ | 3.42 × $10^{12}$ |
|   | 9 | 1 × $10^{12}$ | 5 | 6.031 | 2.18 × $10^8$ | 2.18 × $10^8$ | 2.98 × $10^{12}$ |
| 4 | 10 | 1 × $10^{13}$ | 5 | 11.7 | 7.30 × $10^8$ | 7.26 × $10^8$ | 1.95 × $10^{13}$ |
|   | 11 | 1 × $10^{13}$ | 5 | 7.085 | 3.27 × $10^8$ | 4.96 × $10^8$ | 4.52 × $10^{13}$ |
|   | 12 | 1 × $10^{13}$ | 5 | 67.42 | 3.57 × $10^8$ | 3.47 × $10^8$ | 2.99 × $10^{13}$ |
|   | 13 | 1 × $10^{13}$ | 5 | 19.86 | 1.27 × $10^9$ | 1.23 × $10^9$ | 4.82 × $10^{13}$ |
| 5 | 14 | 3 × $10^{12}$ | 5 | 3.746 | 4.79 × $10^8$ | 4.79 × $10^8$ | 7.61 × $10^{12}$ |
|   | 15 | 3 × $10^{12}$ | 5 | 7.754 | 1.31 × $10^8$ | 1.31 × $10^8$ | 2.54 × $10^{12}$ |
|   | 16 | 3 × $10^{12}$ | 5 | 11.96 | 2.06 × $10^8$ | 2.04 × $10^8$ | 1.12 × $10^{13}$ |
| 6 | 17 | 3 × $10^{12}$ | 20 | 6.779 | 1.10 × $10^8$ | 1.10 × $10^8$ | 6.84 × $10^{12}$ |
|   | 18 | 3 × $10^{12}$ | 20 | 9.062 | 2.35 × $10^7$ | 3.37 × $10^7$ | 2.23 × $10^{12}$ |
|   | 19 | 3 × $10^{12}$ | 20 | 6.151 | 2.34 × $10^8$ | 2.34 × $10^8$ | 1.12 × $10^{13}$ |
| 7 | 20 | 6 × $10^{12}$ | 40 | 46.54 | 1.80 × $10^8$ | 1.80 × $10^8$ | 1.21 × $10^{13}$ |
|   | 21 | 6 × $10^{12}$ | 40 | 22.72 | 5.68 × $10^7$ | 5.68 × $10^7$ | 4.82 × $10^{12}$ |
|   | 22 | 6 × $10^{12}$ | 40 | 51.34 | 6.16 × $10^7$ | 6.37 × $10^7$ | 5.56 × $10^{12}$ |

* an indicative number for each patient
nd: not determined.

FIG. 7 shows the cytokine pattern observed in the cancer patients dosed in the ColoAd1-1001 clinical study in the initial dose escalation phase (up to and including identification of the dose limiting toxicity). As in the mouse studies, the inflammatory cytokine response seen in humans peaks after the first administration of ColoAd1 and then reduces for subsequent administrations. Interestingly, this initial priming effect of ColoAd1 is not reliably seen at the lower doses but is clearly seen at the higher dose, supporting the assertion that a repeated high dose regimen with equal dose levels may be optimal for the intravenous administration of subgroup B adenoviruses to human cancer patients.

In particular FIG. 7 shows cytokine levels (μg/L) over time in human cancer patients with metastatic solid epithelial tumours after intravenous doses of ColoAd1 administered as a 5 minute infusion of 30 ml of viral suspension on Days 1, 3 and 5 (dose points indicated by arrows) at four different dose levels (1e10, 1e11, 1e12 and 1e13 viral particles respectively). Each patient also received prophylactic anti-inflammatory medication and intravenous fluids. Patients at doses up to and including 1e12 tolerated these doses well, but two out of four patients who received the 1e13 dose experienced cytokine mediated dose limiting toxicity and were unable to receive more than a single dose. For the individual patients, raised TNF and gamma interferon levels correlated well with tolerability, but raised IL6 did not (data not shown). It was thus determined that rates up to 2e11 viral particles per minute could be regarded as a well-tolerated infusion rate. Panel A: TNF; Panel B: gamma interferon; Panel C: IL-6.

FIG. 8 shows systemic pharmacokinetics of ColoAd1 (Genome copies per mL of blood) in human cancer patients with metastatic solid epithelial tumours. Genome copies measured by qPCR.

In particular, FIG. 8A shows the mean plasma level of the three patients from the ColoAd1-1001 dosed with a well-tolerated dose (1e12 VP per dose) administered at 2e11 VP/min as equal intravenous doses of ColoAd1 administered as a 5 minute infusion of 30 ml of viral suspension on Days 1, 3 and 5 (dose time points indicated by arrows). The trend towards increasing viral concentration peaks with each subsequent dose is typical.

This clearly shows the beneficial effect of the claimed dosing regimen on viral pharmacokinetics, with the peak levels of virus after the second and third dose being increasingly higher than the peak levels of virus after the first dose. This demonstrates the benefit of occupying or removing the non-cancerous viral sinks with the earlier doses. This dose was well tolerated in these three patients.

FIG. 8B shows the mean initial pharmacokinetics (viral DNA copies/ml) following the first dose of virus at four different dose levels for patient cohorts 1 to 4 ($1\times10^{10}$, $1\times10^{11}$, $1\times10^{12}$ and $1\times10^{13}$ viral particles respectively) of the ColoAd1-1001 clinical study. In each case the dose is administered over 5 minutes and so the viral infusion rate increases from $2\times10^9$ viral particles per minute at the lowest dose to $2\times10^{12}$ viral particles per minute at the top dose. At the top two doses, the blood viral concentration remains above the $2\times10^6$ viral particles per mL level for a prolonged period. This is the minimum blood level (as predicted from preclinical studies and as shown in FIG. 1) to be effective at establishing an infection within the tumour. For the $1\times10^{12}$ dose this target level is achieved for between 1 to 2 hours, whilst for the $1\times10^{13}$ dose this target level is maintained for over 6 hours. However, the $1\times10^{13}$ viral particle dose administered as $2\times10^{12}$ viral particles per minute was poorly tolerated, with two patients suffering acute cytokine mediated dose limiting toxicity and so this dose regimen is not optimal.

A dose regimen using a well-tolerated infusion rate (such as $2\times10^{11}$ viral particles per minute or slower) may allow the administration of doses up to and possibly higher than $1\times10^{13}$ viral particles. Using this data, pharmacokinetic modelling can then be used to show that a dose of $1\times10^{13}$ viral particles infused over one hour ($1.67\times10^{11}$ viral particles per minute) will maintain viral blood levels above the $2\times10^6$ target level for three hours or more in most patients.

FIGS. 9A to 9H shows the pharmacokinetics from patients in the ColoAd1-1001 clinical trial. Patients were administered the first dose of ColoAd1 and the viral load was then assessed with serial blood draws using qPCR. The following treatment regimens were tested:

FIG. 9A: 1e10 ($1\times10^{10}$) viral particles administered over 5 minutes (Cohort 1); FIG. 9B: 1e11 ($1\times10^{11}$) viral particles administered over 5 minutes (Cohort 2); FIG. 9C: 1e12 ($1\times10^{12}$) viral particles administered over 5 minutes (Cohort 3); FIG. 9D: 1e13 ($1\times10^{13}$) viral particles administered over 5 minutes (Cohort 4); FIG. 9E: 3e12 ($3\times10^{12}$) viral particles administered over 5 minutes (Cohort 5); FIG. 9F: 3e12 ($3\times10^{12}$) viral particles administered over 20 minutes (Cohort 6); and FIG. 9G: 6e12 ($6\times10^{12}$) viral particles administered over 40 minutes (Cohort 7).

Each curve represents the viral blood levels measured for an individual test subject per unit time prior to receiving ColoAd1 and up to about 6 hours following treatment.

Adverse side effects were first observed in patients when viral blood levels exceeded a threshold of about 3e8 viral genomes per mL.

Hence, a range of about 3e7 to 3e8 viral genomes per ML was determined to be an ideal therapeutic range and that a regimen which maintains the viral blood levels within this range for as long as possible would maximise viral blood levels, whilst minimising toxic side effects.

As can be seen from the pharmacokinetic curves, FIG. 9G (6e12 particles administered over 40 minutes) shows a particularly suitable profile with the viral blood levels maintained within the therapeutic range for the longest.

FIG. 10 shows a comparison between $C_{max}$ levels when the same dose is administered to patients in the ColoAd1-1001 study as either a slow infusion or a fast infusion. Cohorts 5 and 6 were both administered a total dose of $3\times10^{12}$ viral particles but for cohort 5 the dose was infused over 5 mins (fast infusion) and cohort 6 the dose was infused over 20 mins (slow infusion). It can be seen that slowing the infusion rate can effectively result in less variation of the $C_{Max}$ and a lower mean $C_{Max}$ level, and so limiting the infusion rate of a Group B adenovirus is thus relevant when higher $C_{Max}$ levels are associated with toxicity.

FIG. 11 shows MCP1 levels (μg/L) over time in human cancer patients after intravenous doses of ColoAd1 administered on Days 1, 3 and 5 (dose points indicated by arrows) in ther ColoAd1-1001 clinical study. The graph shows the comparison between the different patient cohorts (1 to 7) that were each administered with a different dose regimen shown in Table 7.

Measurements of MCP1 levels (μg/L) were taken at the following time points: at 0 hours, 6 hours, 12 hours, 24 hours, 48 hours, 54 hours, 60 hours, 72 hours, 96 hours, 102 hours, 108 hours, 120 hours, 168 hours and 336 hours. This human data reflects a similar pattern to that seen in mice with reducing levels of MCP1 after each dose for every dose tested, thus supporting the specific benefits of the claimed dose regimen.

The cytokine pattern seen in FIG. 12 is consistent with the cytokine patterns previously observed in the mice studies (see FIG. 6), showing that after the first dose, each subsequent dose is better tolerated even when each of the 3 doses is equal.

Studies Showing that Infection of Tumours by Type B Adenovirus can be Established by Doses of Viral Particles Administered by IV FIG. 12 shows the replication cycle typical for an adenovirus. Adenovirus structural proteins e.g. Hexon, which makes 90% of the virus capsid, are only expressed late during infection after replication has occurred. The proteins are then transported back to the nucleus for assembly. The nucleus thus has the highest concentration of hexon and other structural proteins during replication. Therefore, nuclear hexon staining can be used for the quantification of adenovirus and as a marker for cells that have been successfully infected with ColoAd1.

In the ColoAd1-1002 clinical study, patients with primary (non-metastatic) colorectal tumours received ColoAd1 by either intratumoural (IT) delivery or intravenous (IV) delivery. In the IT group, the virus was administered via a colonoscope at a dose of up to 1e8 VP as multiple injections (actual dose was dependent upon the tumour size). In the IV group the dose was 1e12 VP administered as an infusion over 5 min on days 1, 3 and 5. Then, 7 to 14 days after the first dose of ColoAd1, the primary tumour was resected and was sent for pathological examination including immunohistochemical (IHC) staining for ColoAd1 hexon.

Sections of formalin-fixed, paraffin-embedded human tumour samples were analyzed for the presence of virus using an anti-hexon antibody (ab8251).

Staining was carried out under using a validated assay with a Ventana Benchmark Ultra. Strong nuclear staining indicates the presence of hexon undergoing capsid assembly.

Isotypes controls were processed at the same time and under the same conditions.

FIG. 13 shows a transmission EM image of a colorectal cancer cell line infected in vitro with ColoAd1.

FIG. 14A shows cell staining images of a tumour sample which has been infected with ColoAd1 after intratumoural injection (IT), and then stained for Hexon. As can be seen, there is substantial nuclear staining in carcinoma cells whereas there is no nuclear staining in stroma cells. FIG. 14B shows the corresponding isotype control. Together these slides show that ColoAd1 infects tumour cells selectively, without infecting normal cells following direct intratumoural delivery.

FIG. 14C shows a cell staining image of a tumour sample which has been infected with ColoAd1 after intravenous (IV) administration, and then stained for Hexon. As can be seen, there is substantial nuclear staining in carcinoma cells whereas there is no nuclear staining in stroma cells. FIG. 14D is the corresponding isotype control.

Therefore, these images provide clear evidence that ColoAd1 can be selectively delivered to tumour cells in a manner that is equivalent to intratumoural delivery when using the claimed intravenous dosing regimen.

Example 2 Drug Combination

ColoAd1 virus replication in the presence of 320 clinically approved compounds or compounds in development was assessed in the colon carcinoma cell line, HT-29. HT-29 cell were seeded at a density of 3.0e4 cells per well in 96 well plates and incubated at 37° C., 5% $CO_2$. After 4-6 hrs incubation virus and drug compound mixtures prepared in cell media were diluted onto the cells to give final doses of 10 ColoAd1 virus particles per cell (ppc) and 0.1 μM of drug compound. The cells were incubated for 18 hrs and then the total virus genomes in the cells were assessed by qPCR. The relative fold change in ColoAd1 replication, compared to ColoAd1 virus alone, is plotted for all compounds in FIG. 15. The inset shows an increase in virus replication after 18 hrs in the presence of microtubule inhibitors and a decrease in virus replication in the presence of topoisomerase inhibitors.

The effect of paclitaxel or cisplatin treatment on ColoAd1 efficacy in a tumour model was assessed in an IP model of ovarian cancer. SCID mice were implanted with 2.5e6 luciferase-expressing SKOV-3 human ovarian carcinoma cells. Tumour burden was assessed by luciferase expression. Mice were imaged on day 5, on the day before each set of treatments and at least every 5-7 days for the duration of the study. All ColoAd1 treatments were carried out using 5e9 virus particles delivered by intra-peritoneal injection and in the combined treatment groups, paclitaxel (0.4 mg) or cisplatin (0.04 mg) was delivered the day after virus treatment. Disease progression was assessed by luciferase imaging using an IVIS imaging system. Images of the relative luminescence in mice dosed via IP injection with either PBS (A), paclitaxel (B), ColoAd1 (C) or paclitaxel and ColoAd1 (D) is shown in FIG. 16 and the relative luminescence tracked over time for each dosing group is shown in FIG. 17. The relative luminescence in mice dosed via IP injection with either PBS (Group 1), ColoAd1 then cisplatin (Group 2), cisplatin then ColoAd1 (Group 3) or Paclitaxel and ColoAd1 (Group 4) are shown in FIG. 18. Dosing schedules are detailed in the FIGS. 17 and 18.

We claim:

1. A method of treating cancer in a human patient, comprising intravenously administering to the patient multiple doses of a formulation of a replication competent oncolytic adenovirus of subgroup B in a single treatment cycle,
wherein a total dose given in each administration is in the range of $1\times10^{12}$ to $1\times10^{13}$ viral particles, and
wherein the rate of viral particle delivery for each administered dose of adenoviruses is in the range of $2\times10^{10}$ to $6\times10^{11}$ particles per minute, and
wherein the adenovirus has a fibre and hexon of wild-type Ad11.

2. The method of claim 1, wherein the period between each dose administration is in the range of 6 hours to 72 hours.

3. The method of claim 1, wherein the multiple doses are 2, 3, 4, 5, 6 or 7 doses in a single treatment cycle.

4. The method of claim 1, wherein the treatment cycle is a period of 14 days or less.

5. The method of claim 1, wherein each dose of adenovirus is administered such that the rate of viral particle delivery is in the range of $1\times10^{11}$ to $3\times10^{11}$ viral particles per minute.

6. The method of claim 1, wherein $1\times10^{13}$ viral particles are administered over a 60 minute period per dose or wherein $6\times10^{12}$ viral particles are administered over a 40 minute period per dose.

7. The method of claim 1, wherein a blood level of the adenovirus after administration of a second and optionally subsequent doses reaches a blood level of at least $2\times10^{6}$ viral particles per mL.

8. The method of claim 7, wherein the blood level of viral particles is maintained for 15 minutes or greater.

9. The method of claim 1, wherein the volume of the formulation administered is 100 mL or less.

10. The method of claim 1, wherein the multiple doses comprise a first dose that is administered on day 1, a second dose that is administered on day 3, and a third dose that is administered on day 5, and further wherein no dose is administered on day 2 or on day 4.

11. The method of claim 1, wherein the adenovirus is a chimeric adenovirus.

12. The method of claim 1, wherein the adenovirus is administered in combination with the administration of an anti-cancer therapy, wherein the anti-cancer therapy is an immunotherapeutic agent, a small molecule inhibitor, radiotherapy, radio-isotope therapy or any combination thereof.

13. The method of claim 1, wherein the adenovirus is administered in combination with the administration of one or more prophylactic agents.

14. The method of claim 1 for the treatment of a tumour.

15. The method of claim 1, wherein the first dose in the treatment of a given cycle is a lower dose than the dose administered in subsequent treatments in the cycle.

16. The method of claim 1, wherein the same total dose is given in the first and the second administrations.

17. The method of claim 1, wherein the same total dose is given for all of the administered doses in the cycle.

18. The method of claim 1, wherein the administration of the multiple doses of replication competent oncolytic adenovirus seeds viral infection in the cancer cells.

19. The method of claim 10, wherein the adenovirus is unconjugated.

* * * * *